(12) United States Patent
Ji et al.

(10) Patent No.: US 8,399,488 B2
(45) Date of Patent: *Mar. 19, 2013

(54) BIPHENYL COMPOUNDS USEFUL AS MUSCARINIC RECEPTOR ANTAGONISTS

(75) Inventors: YuHua Ji, Redwood City, CA (US); Mathai Mammen, Menlo Park, CA (US); Craig Husfeld, Redwood City, CA (US); Li Li, Sunnyvale, CA (US); YongQi Mu, Los Altos, CA (US); Aaron Kushner, Irvine, CA (US); Eric Stangeland, Pacifica, CA (US); Trevor Mischki, Ottawa (CA); Adam Hughes, Belmont, CA (US); Sarah Dunham, San Anselmo, CA (US)

(73) Assignee: Theravance, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/348,085

(22) Filed: Jan. 11, 2012

(65) Prior Publication Data

US 2012/0122850 A1 May 17, 2012

Related U.S. Application Data

(62) Division of application No. 13/193,874, filed on Jul. 29, 2011, now Pat. No. 8,119,796, which is a division of application No. 12/759,887, filed on Apr. 14, 2010, now Pat. No. 8,013,152, which is a division of application No. 11/451,179, filed on Jun. 12, 2006, now Pat. No. 7,728,144.

(60) Provisional application No. 60/690,008, filed on Jun. 13, 2005.

(51) Int. Cl.
*A61K 31/4525* (2006.01)
*A61K 31/454* (2006.01)
*A61K 31/4545* (2006.01)
*C07D 401/12* (2006.01)

(52) U.S. Cl. ........ 514/318; 514/326; 514/333; 514/342; 546/208; 546/209; 546/212

(58) Field of Classification Search ................ 546/208, 546/209, 212; 514/318, 326, 333, 342
See application file for complete search history.

(56) References Cited

U.S. PATENT DOCUMENTS

| | | |
|---|---|---|
| 6,617,325 B1 | 9/2003 | Lehman-Lintz et al. |
| 6,635,764 B2 | 10/2003 | Mammen et al. |
| 6,656,694 B2 | 12/2003 | Mammen |
| 6,693,202 B1 | 2/2004 | Aggen et al. |
| 7,141,671 B2 | 11/2006 | Mammen et al. |
| 7,238,709 B2 | 7/2007 | Mammen et al. |
| 7,262,205 B2 | 8/2007 | Mammen et al. |
| 7,265,133 B2 | 9/2007 | Mammen et al. |
| 7,288,657 B2 | 10/2007 | Mammen et al. |
| 7,345,060 B2 | 3/2008 | Mammen et al. |
| 7,456,199 B2 | 11/2008 | Mammen et al. |
| 7,479,562 B2 | 1/2009 | Ji et al. |
| 7,501,442 B2 | 3/2009 | Mammen et al. |
| 7,524,962 B2 | 4/2009 | Mammen et al. |
| 7,550,595 B2 | 6/2009 | Mammen et al. |
| 7,560,469 B2 | 7/2009 | Mammen et al. |
| 7,569,588 B2 | 8/2009 | Mammen et al. |
| 7,629,336 B2 | 12/2009 | Ji et al. |
| 7,632,847 B2 | 12/2009 | Mu et al. |
| 7,642,355 B2 | 1/2010 | Mu et al. |
| 7,659,403 B2 | 2/2010 | Mu et al. |
| 7,687,519 B2 | 3/2010 | Mu et al. |
| 7,816,532 B2 | 10/2010 | Mammen et al. |
| 7,851,632 B2 | 12/2010 | Mammen et al. |
| 7,858,795 B2 | 12/2010 | Mammen et al. |
| 7,868,175 B2 | 1/2011 | Ji et al. |
| 2003/0018019 A1 | 1/2003 | Meade et al. |
| 2004/0167167 A1* | 8/2004 | Mammen et al. ............. 514/317 |
| 2004/0209860 A1 | 10/2004 | Mammen et al. |
| 2004/0209915 A1 | 10/2004 | Mammen et al. |
| 2005/0113417 A1* | 5/2005 | Mammen et al. ............. 514/320 |
| 2010/0063096 A1 | 3/2010 | Mu et al. |
| 2010/0093753 A1 | 4/2010 | Mu et al. |

FOREIGN PATENT DOCUMENTS

| | | |
|---|---|---|
| EP | 0 747 355 A1 | 12/1996 |
| WO | WO 95/06635 A1 | 3/1995 |
| WO | WO 99/64043 A1 | 12/1999 |
| WO | WO 02/051841 A1 | 7/2002 |
| WO | WO 2004/012684 A2 | 2/2004 |

OTHER PUBLICATIONS

Dorwald F. A. Side Reactions in Organic Synthesis, 2005, Wiley: VCH, Weinheim p. IX of Preface.*
Broadley et al., "Muscarinic Receptor Agonists and Antagonists", Molecules, 6, pp. 142-193 (2001).
Eglen et al., "Muscarinic Receptor Subtypes:Pharmacology and Therapeutic Potential", DN&P, 10(8), pp. 462-469 (1997).

(Continued)

*Primary Examiner* — Rita Desai
(74) *Attorney, Agent, or Firm* — Jeffrey A. Hagenah; Shelley Eberle

(57) ABSTRACT

The invention provides compounds of formula I:

wherein a, b, c, m, s, t, W, Z, Ar, $R^1$, $R^2$, $R^3$, $R^6$, and $R^7$ are as defined in the specification. The compounds of formula I are muscarinic receptor antagonists. The invention also provides pharmaceutical compositions containing such compounds, processes and intermediates for preparing such compounds and methods of using such compounds to treat pulmonary disorders.

14 Claims, No Drawings

OTHER PUBLICATIONS

Zlotos et al., "Muscarinic receptor agonists and antagonists", Exp. Opin. Ther. Patents, 9(8), pp. 1029-1053 (1999).

Naito et al., "Selective Muscarinic Antagonist. II.[1]) Synthesis and Antimuscarinic Properties of Biphenylylcarbamate Derivatives", Chem. Pharm. Bull., vol. 46, No. 8, pp. 1286-1294 (1998).

* cited by examiner

BIPHENYL COMPOUNDS USEFUL AS MUSCARINIC RECEPTOR ANTAGONISTS

CROSS-REFERENCE TO RELATED APPLICATIONS

This application is a divisional application of U.S. Ser. No. 13/193,874, filed Jul. 29, 2011, now allowed, which is a divisional application of U.S. Ser. No. 12/759,887, filed Apr. 14, 2010, now issued as U.S. Pat. No. 8,013,152, which is a divisional application of U.S. Ser. No. 11/451,179, filed Jun. 12, 2006, now issued as U.S. Pat. No. 7,728,144, which claims the benefit of U.S. Provisional Application No. 60/690,008, filed on Jun. 13, 2005; the disclosures of which are incorporated herein by reference in their entirety.

BACKGROUND OF THE INVENTION

1. Field of the Invention

The present invention relates to novel biphenyl compounds having muscarinic receptor antagonist or anticholinergic activity. The invention also relates to pharmaceutical compositions comprising these compounds, processes and intermediates for preparing these compounds and methods of using these compounds to treat pulmonary disorders.

2. State of the Art

Pulmonary or respiratory disorders, such as chronic obstructive pulmonary disease (COPD) and asthma, afflict many millions of people worldwide and are a leading cause of morbidity and mortality. Muscarinic receptor antagonists are known to provide bronchoprotective effects and therefore are useful for treating respiratory disorders, such as COPD and asthma. Muscarinic receptor antagonists are typically administered by inhalation to treat these disorders. However, even when administered by inhalation, a significant amount of the antagonist is often absorbed into the systemic circulation resulting in systemic side effects, such as dry mouth, mydriasis and cardiovascular side effects. In addition, many inhaled muscarinic receptor antagonists have a relatively short duration of action requiring that they be administered several times per day. This multiple-daily dosing regime is inconvenient and creates a significant risk of inadequate treatment due to patient non-compliance with the required frequent dosing schedule.

Accordingly, a need exists for new muscarinic receptor antagonists, in particular, those having high potency and reduced systemic side effects when administered by inhalation. Additionally, a need exists for inhaled muscarinic receptor antagonists having a long duration of action thereby allowing for once-daily or even once-weekly dosing. Such compounds are expected to be particularly effective for treating pulmonary disorders, such as COPD and asthma, while reducing or eliminating side effects, such as dry-mouth and constipation.

SUMMARY OF THE INVENTION

The present invention provides novel biphenyl compounds having muscarinic receptor antagonist or anticholinergic activity. Among other properties, compounds of the invention are expected to possess high potency and reduced systemic side effects when administered by inhalation and are also expected to possess a long duration of action.

One aspect of the invention relates to a compound of formula I:

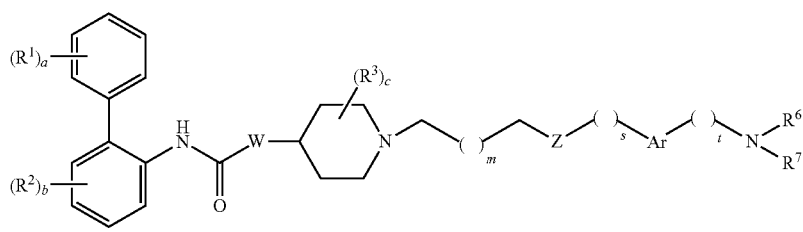

wherein:

a is 0 or an integer of from 1 to 5;

each $R^1$ is independently selected from —$C_{1-5}$alkyl, —$C_{2-5}$alkenyl, —$C_{2-5}$alkynyl, —$C_{3-6}$cycloalkyl, -cyano, -halo, —OR", —C(O)O$R^{1b}$, —S$R^{1c}$, —S(O)$R^{1d}$, —S(O)$_2$$R^{1e}$, —N$R^{1f}R^{1g}$, —N$R^{1h}$S(O)$_2$$R^{2i}$, and —N$R^{2j}$C(O)$R^{2k}$, where each of $R^{2a-2k}$ is independently —H, —$C_{1-5}$alkyl or -phenyl-$C_{1-5}$alkyl;

b is 0 or an integer of from 1 to 4;

each $R^2$ is independently selected from —$C_{1-5}$alkyl, —$C_{2-5}$alkenyl, —$C_{2-5}$alkynyl, —$C_{3-6}$cycloalkyl, -cyano, -halo, —O$R^{2a}$, —C(O)O$R^{2b}$, —S$R^2$, —S(O)$R^{2d}$, —S(O)$_2$$R^{2e}$, —N$R^{2f}R^{2g}$, —N$R^{2h}$S(O)$_2$$R^{2i}$, and —N$R^{2j}$C(O)$R^{2k}$; where each of $R^{2a-2k}$ is independently —H, —$C_{1-5}$alkyl or -phenyl-$C_{1-5}$alkyl;

W is —O— or —N$W^a$—, where $W^a$ is —H or —$C_{1-5}$alkyl;

c is 0 or an integer from 1 to 5;

each $R^3$ independently is —$C_{1-5}$alkyl or two $R^3$ groups are joined to form $C_{1-3}$alkylene, $C_{2-3}$alkenylene or oxiran-2,3-diyl;

m is 0 or 1;

Z is selected from —C(O)N($R^4$)— and —N($R^4$)C(O)—, where $R^4$ is selected from —H, —$C_{1-5}$alkyl, and —$C_{3-5}$cycloalkyl;

s is 0, 1 or 2;

Ar is a phenylene group or a $C_{3-5}$heteroarylene group containing 1 or 2 heteroatoms independently selected from oxygen, nitrogen or sulfur; wherein the phenylene or $C_{3-5}$heteroarylene group is substituted with $(R^5)_q$ where q is 0 or an integer from 1 to 4 and each $R^5$ is independently selected from - halo, —OH, —$C_{1-5}$alkyl or —$C_{1-5}$alkoxy;

t is 0, 1 or 2;

$R^6$ is selected from —H, —$C_{1-5}$alkyl, and $X^6R^{6a}$; where $X^6$ is —$C_{1-5}$alkylene and $R^{6a}$ is selected from —OH, —$C_{1-5}$alkoxy and -heteroaryl; and $R^7$ is selected from —H, —$C_{1-5}$alkyl, —$C_{3-6}$cycloalkyl, and —$X^7R^{7a}$; where $X^7$ is selected from —$C_{1-5}$alkylene, —C(O)—, —$C_{1-5}$alkylene-C(O)—, —S(O)$_2$—, —$C_{1-5}$alkylene-S(O)$_2$—, and —S(O)$_2$—$C_{1-5}$alkylene; and $R^{7a}$ is selected from —OH, —$C_{1-5}$alkyl, —$C_{3-6}$cycloalkyl, —$C_{1-5}$alkoxy, heteroaryl, —N$R^{7b}R^{7c}$, where $R^{7b}$ and $R^{7c}$ are independently —H or —$C_{1-5}$alkyl, and aryl optionally substituted with 1-2-$C_{1-5}$alkyl or halo groups;

or $R^6$ and $R^7$ are taken together to form:

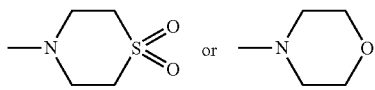

optionally substituted with one to three —$C_{1-5}$alkyl groups, or

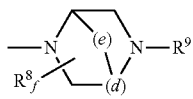

where: d is 1 or 2; e is 0, 1 or 2; f is 0, 1, 2 or 3; $R^8$ is selected from —$C_{1-5}$alkyl and =O; $R^9$ is selected from —H, —$C_{1-5}$ alkyl, hydroxyphenyl, heteroaryl, and —$X^9R^{9a}$; where $X^9$ is selected from —$C_{1-5}$ alkylene, —C(O)—, —$C_{1-5}$alkylene-C(O)—, —C(O)—$C_{1-5}$alkylene, —S(O$_2$)—, —$C_{1-5}$alkylene-S(O$_2$)—, and —S(O$_2$)—$C_{1-5}$alkylene; and $R^{9a}$ is selected from —H, —OH, —$C_{1-5}$alkyl, —$C_{1-5}$alkoxy, aryl, heteroaryl, heterocyclyl, and —$NR^{9b}R^{9c}$, where $R^{9b}$ and $R^{9c}$ are independently —H or —$C_{1-5}$alkyl;

wherein each alkyl and alkoxy group in $R^1$, $R^{1a-1k}$, $R^2$, $R^{2a-2k}$, $R^3$, $R^5$, $R^6$, $R^{6a}$, $R^7$, $R^{7a-c}$, $R^8$, $R^9$, and $R^{9a-c}$ is optionally substituted with 1 to 5 fluoro substituents;

or a pharmaceutically acceptable salt, solvate, or stereoisomer thereof.

Another aspect of the invention pertains to pharmaceutical compositions comprising a pharmaceutically acceptable carrier and a therapeutically effective amount of a compound of formula I or a pharmaceutically acceptable salt, solvate, or stereoisomer thereof. Yet another aspect of the invention pertains to compositions comprising a compound of formula I in combination with one or more other therapeutic agents. Accordingly, in one embodiment, the invention is directed to compositions comprising (a) a pharmaceutically acceptable carrier and a therapeutically effective amount of a compound of formula I or a pharmaceutically acceptable salt or solvate or stereoisomer thereof; and (b) a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of formula I and the agent are formulated together or separately. When the agent is formulated separately, a pharmaceutically acceptable carrier may be included.

Compounds of the invention possess muscarinic receptor antagonist activity. Accordingly, compounds of formula I are expected to be useful for treating pulmonary disorders, such as chronic obstructive pulmonary disease and asthma.

Yet another aspect of the invention is directed to methods for treating a pulmonary disorders comprising administering to a patient a therapeutically effective amount of a compound of formula I or a pharmaceutically acceptable salt or solvate or stereoisomer thereof. Still another aspect of the invention pertains to methods of producing bronchodilation in a patient comprising administering to a patient a bronchodilation-producing amount of a compound of formula I or a pharmaceutically acceptable salt or solvate or stereoisomer thereof. The invention is also directed to methods of treating chronic obstructive pulmonary disease or asthma comprising administering to a patient a therapeutically effective amount of a compound of formula I or a pharmaceutically acceptable salt or solvate or stereoisomer thereof. In another aspect, the invention is directed to methods for antagonizing a muscarinic receptor in a mammal comprising administering to the mammal a therapeutically effective amount of the compound of formula I.

Since compounds of the invention possess muscarinic receptor antagonist activity, such compounds are also useful as research tools. Accordingly, in yet another embodiment, the invention is directed to methods for using a compound of formula I or a pharmaceutically acceptable salt or solvate or stereoisomer thereof as a research tool for studying a biological system or sample, or for discovering new chemical compounds having muscarinic receptor antagonist activity.

The invention is also directed to processes and intermediates useful for preparing compounds of formula I and pharmaceutically acceptable salts or solvates or stereoisomers thereof. Accordingly, in another embodiment, the invention is directed to a process of preparing a compound of formula I, the process comprising: (a) reacting a compound of formula II with a compound of formula III; or (b) coupling a compound of formula IVa with a compound of formula Va or coupling a compound of formula IVb with a compound of formula Vb; or (c) reacting a compound of formula VI with a compound of formula VII; or (d) reacting a compound of formula II with a compound of formula VIII in the presence of a reducing agent; or (e) reacting a compound of formula IX with a compound of formula VII in the presence of a reducing agent; and then removing any protecting groups that may be present to provide a compound of formula I, and optionally, forming a pharmaceutically acceptable salt thereof, wherein compounds of formula I-IX, are as defined herein.

In one embodiment, the above process further comprises the step of forming a pharmaceutically acceptable salt of a compound of formula I. In other embodiments, the invention is directed to the other processes described herein; and to the products prepared by any of the processes described herein.

The invention is also directed to a compound of formula I or a pharmaceutically acceptable salt or solvate or stereoisomer thereof, for use in therapy or as a medicament. Additionally, the invention is directed to the use of a compound of formula I or a pharmaceutically acceptable salt or solvate or stereoisomer thereof, for the manufacture of a medicament; especially for the manufacture of a medicament for the treatment of a pulmonary disorder or for antagonizing a muscarinic receptor in a mammal.

DETAILED DESCRIPTION OF THE INVENTION

In one embodiment, the invention is directed to novel biphenyl compounds of formula I, and pharmaceutically acceptable salts or solvates or stereoisomers thereof. The compounds may contain one or more chiral centers and therefore, the invention is also directed to racemic mixtures, pure stereoisomers (i.e., enantiomers or diastereomers), stereoisomer-enriched mixtures, and the like unless otherwise indicated. When a particular stereoisomer is shown or named herein, it will be understood by those skilled in the art that minor amounts of other stereoisomers may be present in the compositions of the invention unless otherwise indicated, provided that the desired utility of the composition as a whole is not eliminated by the presence of such other isomers.

The compounds of formula I also contain several basic groups (e.g., amino groups) and therefore, the compounds of formula I can exist as the free base or in various salt forms. All such salt forms are included within the scope of the invention.

Furthermore, solvates of compounds of formula I or salts thereof are included within the scope of the invention. Additionally, where applicable, all cis-trans or E/Z isomers (geometric isomers), tautomeric forms and topoisomeric forms of the compounds of formula I are included within the scope of the invention unless otherwise specified.

The compounds of formula I, as well as those compounds used in its synthesis, may also include isotopically-labeled compounds, i.e., where one or more atoms have been enriched with atoms having an atomic mass different from the atomic mass predominately found in nature. Examples of isotopes that may be incorporated into the compounds of formula I include, but are not limited to, $^2H$, $^{13}H$, $^{13}C$, $^{14}C$, $^{15}N$, $^{18}O$ and $^{17}O$.

The nomenclature used herein to name the compounds of the invention is illustrated in the Examples. This nomenclature has been derived using the commercially-available AutoNom software (MDL, San Leandro, Calif.). For example, compounds of formula I wherein W is O have typically been named as ester derivatives of biphenyl-2-ylcarbamic acid.

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

The values for a and b are independently 0, 1, 2, 3, 4 or 5; particularly independently 0, 1 or 2, and even more particularly 0 or 1. In one embodiment, both a and b are 0. When present, each $R^1$ may be at the 2, 3, 4, 5 or 6-position of the phenyl ring to which it is attached. Each $R^1$ is independently selected from —$C_{1-5}$alkyl, —$C_{2-5}$alkenyl, —$C_{2-5}$alkynyl, —$C_{3-6}$cycloalkyl, -cyano, -halo, —$OR^{1a}$, —$C(O)OR^{1b}$, —$SR^{1c}$, —$S(O)R^{1d}$, —$S(O)_2R^{1e}$, —$NR^{1f}R^{1g}$, —$NR^{1h}S(O)_2R^{1i}$, and —$NR^{1j}C(O)R^{1k}$, examples of which include methyl, fluoro, chloro, bromo, hydroxy, methoxy, amino, methylamino, dimethylamino and the like. Particular values for $R^1$ are fluoro or chloro. When present, each $R^2$ may be at the 3, 4, 5 or 6-position on the phenylene ring to which it is attached (where the carbon atom on the phenylene ring attached to the nitrogen atom is position 1). Each $R^2$ is independently selected from —$C_{1-5}$alkyl, —$C_{2-5}$alkenyl, —$C_{2-5}$alkynyl, —$C_{3-6}$cycloalkyl, -cyano, -halo, —$OR^{2a}$, —$C(O)OR^{2b}$, —$SR^{2c}$, —$S(O)R^{2d}$, —$S(O)_2R^{2e}$, —$NR^{2f}R^{2g}$, —$NR^{2h}S(O)_2R^{2i}$, and —$NR^{2j}C(O)R^{2k}$, examples of which include methyl, fluoro, chloro, bromo, hydroxy, methoxy, amino, methylamino, dimethylamino and the like. Particular values for $R^2$ are fluoro or chloro.

Each $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$ and $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$ as used in $R^1$ and $R^2$, respectively, is independently —H, —$C_{1-5}$alkyl or -phenyl-$C_{1-5}$alkyl, examples of which include hydrogen, methyl, ethyl, n-propyl, isopropyl, n-butyl, sec-butyl, isobutyl, tert-butyl or benzyl. In one embodiment, these groups are independently hydrogen or —$C_{1-3}$alkyl. In another embodiment, these groups are independently hydrogen, methyl or ethyl. In addition, each alkyl and alkoxy group in $R^1$, $R^{1a-1k}$, $R^2$, and $R^{2a-2k}$ is optionally substituted with 1 to 5 fluoro substituents.

In one embodiment of the invention, W is —O—. Generally, it has been found that compounds in which W represents —O— exhibit particularly high affinity for muscarinic receptors. In another embodiment W is —$NW^a$—, where $W^a$ is —H or —$C_{1-4}$alkyl, examples of which include hydrogen, methyl, ethyl, n-propyl, isopropyl, n-butyl, sec-butyl, isobutyl and tert-butyl. In one embodiment, $W^a$ is hydrogen or —$C_{1-3}$alkyl. In another embodiment, $W^a$ is hydrogen, methyl or ethyl, particularly hydrogen or methyl. In yet another embodiment, $W^a$ is hydrogen and —$NW^a$— is —NH—.

The value for c is 0, 1, 2, 3, 4, or 5; particularly 0, 1, or 2; and more particularly 0 or 1. In one particular embodiment, c is 0. Each $R^3$ independently represents —$C_{1-5}$alkyl or two $R^3$ groups that are joined to form $C_{1-3}$alkylene, $C_{2-3}$alkenylene or oxiran-2,3-diyl. In one embodiment, each $R^3$ is independently —$C_{1-5}$alkyl, such as methyl, ethyl, n-propyl, isopropyl, n-butyl, sec-butyl, isobutyl and tert-butyl. In addition, each alkyl group in $R^3$ is optionally substituted with 1 to 5 fluoro substituents. In one embodiment, each $R^3$ is independently —$C_{1-3}$alkyl, and in another embodiment, each $R^3$ is independently methyl or ethyl.

In one embodiment, each $R^3$ is at the 3, 4 or 5-position on the piperidine ring (where the nitrogen atom of the piperidine ring is position 1). In a particular embodiment, $R^3$ is at the 4-position on the piperidine ring. In another embodiment, $R^3$ is at the 1-position of the piperidine ring, i.e., on the nitrogen atom of the piperidine ring thus forming a quaternary amine salt.

In yet another embodiment, two $R^3$ groups are joined to form a $C_{1-3}$alkylene or $C_{2-3}$alkenylene group. For example, two $R^3$ groups at the 2 and 6-positions on the piperidine ring can be joined to form an ethylene bridge (i.e., the piperidine ring and the $R^3$ groups form an 8-azabicyclo[3.2.1]octane ring); or two $R^3$ groups at the 1 and 4-positions on the piperidine ring can be joined to form an ethylene bridge (i.e., the piperidine ring and the $R^3$ groups form an 1-azabicyclo[2.2.2]octane ring). In this embodiment, other $R^3$ groups as defined herein may also be present.

In still another embodiment, two $R^3$ groups are joined to form a oxiran-2,3-diyl group. For example, two $R^3$ groups at the 2 and 6-positions on the piperidine ring can be joined to form a 3-oxatricyclo[3.3.1.0$^{2,4}$]nonane ring). In this embodiment, other $R^3$ groups as defined herein may also be present.

The value for m is 0 or 1. In one embodiment, m is 0.

Z is selected from —$C(O)N(R^4)$— and —$N(R^4)C(O)$—. $R^4$ is —H, —$C_{1-5}$alkyl, or —$C_{3-5}$cycloalkyl. Examples of —$C_{1-5}$alkyl groups include methyl, ethyl, n-propyl, isopropyl, n-butyl, sec-butyl, isobutyl, tert-butyl, and pentyl. Examples of —$C_{3-5}$cycloalkyl groups include cyclopropyl, cyclobutyl, and cyclopentyl. In one embodiment $R^4$ is hydrogen or —$C_{1-3}$alkyl, in particular hydrogen or methyl. Exemplary embodiments of Z include —NHC(O)—, —N(CH$_3$)C(O)—, and —C(O)NH—.

The value for s is 0, 1 or 2. One particular value for s is 0; in another embodiment, is 1; and in yet another embodiment, the value for s is 2.

Ar is a phenylene group or a $C_{3-5}$heteroarylene group containing 1 or 2 heteroatoms independently selected from oxygen, nitrogen or sulfur. The phenylene or heteroarylene group may be unsubstituted (q is 0) or substituted with 1, 2, 3, or 4 (q is 1, 2, 3, or 4) $R^5$ substituents, which are independently selected from -halo, —OH, —$C_{1-5}$alkyl or —$C_{1-5}$alkoxy. In addition, each alkyl and alkoxy group in $R^5$ is optionally substituted with 1 to 5 fluoro substituents. In one embodiment, q is 0, 1, 2 or 3; in another embodiment, q is 0, 1 or 2. In another embodiment, q is 1 and $R^5$ is methoxy. The point of attachment for Ar is at any available carbon or heteroatom ring atom. In certain embodiments, Ar is a phenylene group attached at the meta or para position.

In one embodiment Ar is phen-1,3-ylene or phen-1,4-ylene wherein the phenylene group is unsubstituted or substituted with 1, 2 or 3 $R^5$ substituents. Representative $R^5$ substituents include fluoro, chloro, bromo, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of $Ar^1$ groups in this embodiment include 2-fluorophen-1,4-ylene, 3-fluorophen-1,4-ylene, 2-chlorophen-1,4-ylene, 3-chlorophen-1,4-ylene, 2-methylphen-1,4-ylene, 3-methylphen-1,4-ylene, 2-methoxyphen-1,4-ylene, 3-methoxyphen-1,4-ylene, 2-trifluoromethoxyphen-1,4-ylene, 3-trifluoromethoxyphen-1,4-ylene, 2,3-difluorophen-1,4-ylene, 2,5-difluorophen-1,4-ylene, 2,6-difluorophen-1,4-ylene, 2,3-dichlorophen-1,4-ylene, 2,5-dichlorophen-1,4-ylene, 2,6-dichlorophen-1,4-ylene, 2-chloro-5-methoxyphen-1,4-ylene, 2-chloro-6-methoxyphen-1,4-ylene, 2-chloro-5-trifluoromethoxyphen-1,4-ylene, 2-chloro-6-trifluoromethoxyphen-1,4-ylene, and 2,5-dibromophen-1,4-ylene.

In another embodiment, Ar is a $C_{3-5}$heteroarylene group containing 1 or 2 heteroatoms, and is unsubstituted or substituted with 1 or 2 $R^5$ substituents. Representative $C_{3-5}$heteroarylene groups include divalent species of pyrrole, imidazole, thiazole, oxazole, furan, thiophene, pyrazole, isoxazole, isothiazole, pyridine, pyrazine, pyridazine and pyrimidine, where the point of attachment is at any available carbon or nitrogen ring atom. More specific examples of such Ar groups include: pyridylene such as 2,5-pyridylene and 2,6-pyridylene; thienylene such as 2,4-thienylene and 2,5-thienylene; pyrrolylene such as 2,4-pyrrolylene and 2,5-pyrrolylene; and furylene such as 2,5-furylene. Representative $R^5$ substituents include fluoro, chloro, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of substituted Ar groups include 3-fluoro-2,5-thienylene, 3-chloro-2,5-thienylene, 3-methyl-2,5-thienylene, 3-methoxy-2,5-thienylene, and 3-methoxy-6-chloro-2,5-pyridylene.

In one particular embodiment, Ar represents phen-1,3-ylene, phen-1,4-ylene, 2-methoxyphen-1,4-ylene, 2,5-pyridylene, 2,5-thienylene, 2,4-pyrrolylene, 2,5-pyrrolylene, or 2,5-furylene.

The value for t is 0, 1 or 2. A particular value for t is 1.

$R^6$ is selected from —H, —$C_{1-5}$alkyl, and —$X^6R^{6a}$, where $X^6$ is —$C_{1-5}$alkylene and $R^{6a}$ is selected from —OH, —$C_{1-5}$alkoxy and -heteroaryl. In one embodiment, $R^6$ is —H. In another embodiment, $R^6$ is —$C_{1-5}$alkyl such as methyl or ethyl. In another embodiment, $R^6$ is —$X^6R^{6a}$, where $X^6$ is —$C_{1-5}$alkylene such as —$(CH_2)_2$—, and $R^{ha}$ is —OH. In yet another embodiment, $R^6$ is —$X^6R^{6a}$, where $X^6$ is —$C_{1-5}$alkylene such as —$(CH_2)_2$—, and $R^{6a}$ is —$C_{1-5}$alkoxy such as —$OCH_3$ or —$OCH_2CH_3$. In addition, each alkyl and alkoxy group in $R^6$ and $R^{6a}$ is optionally substituted with 1 to 5 fluoro substituents.

$R^7$ is selected from —H, —$C_{1-5}$alkyl, —$C_{3-6}$cycloalkyl, and —$X^7R^{7a}$. $X^7$ is selected from —$C_{1-5}$alkylene, —C(O)—, —$C_{1-5}$alkylene-C(O)—, —$S(O_2)$—, —$C_{1-5}$allylene-S($O_2$)—, and —$S(O_2)$—$C_{1-5}$alkylene. $R^{1a}$ is selected from —OH, —$C_{1-5}$alkyl, —$C_{3-6}$cycloalkyl, —$C_{1-5}$alkoxy, heteroaryl, —$NR^{7b}R^{7c}$ ($R^{7b}$ and $R^{7C}$ are independently —H or —$C_{1-5}$alkyl), and aryl (which may be substituted with 1 or 2-$C_{1-5}$alkyl or halo groups). In addition, each alkyl and alkoxy group in $R^7$ and $R^{7a-c}$ is optionally substituted with 1 to 5 fluoro substituents. For example, $R^7$ can be —$CH_2CH_2CF_3$ or —$S(O_2)CF_3$. In one embodiment, $R^7$ is —H. In one embodiment, $R^7$ is —$C_{1-5}$alkyl such as methyl, ethyl, isopropyl, isobutyl, and tert-butyl. In another embodiment, $R^7$ is —$C_{3-6}$cycloalkyl such as cyclopropyl, cyclobutyl, or cyclopentyl. In yet another embodiment, $R^7$ is —$X^7R^{7a}$, where $X^7$ is —$C_{1-5}$alkylene such as —$CH_2$—, and $R^{7a}$ is: —$C_{3-6}$cycloalkyl such as cyclopropyl; heteroaryl such as 2-thienyl, 2-pyridyl, 3-pyridyl, 4-pyridyl, 2-furyl, 5-benzo[1,3]dioxole, or 7-1H-indole. $X^7$ can also be —$C_{1-5}$alkylene such as —$(CH_2)_2$—, and $R^{7a}$ can be —OH, or —$C_{1-5}$alkoxy such as —$OCH_3$ and —$OCH_2CH_3$. $R^7$ can also be —$X^7R^{7a}$, where $X^7$ is —C(O)—, and $R^{7a}$ is —$C_{1-5}$alkyl such as methyl, —$C_{3-6}$cycloalkyl such as cyclopropyl or cyclobutyl, heteroaryl such as 2-furyl, 2-thienyl, or 4-pyridyl. In another embodiment, $R^7$ is —$X^7R^{7a}$, where $X^7$ is —$C_{1-5}$alkylene-C(O)— such as —$CH_2C(O)$—, and $R^{7a}$ is: —OH; or —$NR^{7b}R^{7c}$ such as —$NH_2$. $R^7$ can also be —$X^7R^{7a}$, where $X^7$ is —$S(O_2)$—, and $R^{7a}$ is: —$C_{1-5}$alkyl such as methyl, ethyl, n-propyl, isopropyl, and n-butyl; heteroaryl such as 2-thienyl and 8-quinolinyl; or aryl such as 4-trifluoromethylphenyl, 2-fluorophenyl, 2,6-dichlorophenyl, 4-methylphenyl, and phenyl. In another embodiment, $R^7$ is —$X^7R^{7a}$, where $X^7$ is —$C_{1-5}$alkylene-$S(O_2)$— such as —$(CH_2)_2S(O_2)$—, and $R^{7a}$ is —$C_{1-5}$alkyl such as methyl. In yet another embodiment, $R^7$ is —$X^7R^{7a}$, where $X^7$ is —$S(O_2)$—$C_{1-5}$alkylene such as —$S(O_2)(CH_2)_2$—, and $R^{7a}$ is —$NR^{7b}R^{7c}$ such as —$NHCH_3$.

One particular $R^6/R^7$ combination is where $R^6$ is —H and $R^7$ is —H, —$C_{1-5}$alkyl (e.g., methyl, ethyl, isopropyl, isobutyl, or tert-butyl), or —$C_{3-6}$cycloalkyl (e.g., cyclopropyl, cyclobutyl, or cyclopentyl). In another combination, $R^6$ is —H and $R^7$ is —$X^7R^{7a}$, where $X^7$ is —$C_{1-5}$alkylene (e.g., —$CH_2$—), and $R^{7a}$ is —$C_{3-6}$cycloalkyl (e.g., cyclopropyl) or heteroaryl (e.g., 2-thienyl, 2-pyridyl, 3-pyridyl, 4-pyridyl, 2-furyl, 5-benzo[1,3]dioxole, or 7-1H-indole). $X^7$ may also be —$C_{1-5}$alkylene such as —$(CH_2)_2$—, and $R^{7a}$ is —OH or —$C_{1-5}$alkoxy such as —$OCH_3$. Another particular $R^6/R^7$ combination is where $R^6$ is —H, and $R^7$ is —$X^7R^{7a}$, where $X^7$ is —C(O)—, and $R^{7a}$ is: —$C_{1-5}$alkyl such as methyl; —$C_{3-6}$cycloalkyl such as cyclopropyl or cyclobutyl; or heteroaryl such as 2-furyl, 2-thienyl, or 4-pyridyl.

Another particular $R^6/R^7$ combination is where $R^6$ is —H, and $R^7$ is —$X^7R^{7a}$, where $X^7$ is —$C_{1-5}$alkylene-C(O)— such as —$CH_2C(O)$—, and $R^{7a}$ is —$NR^{7b}R^{7c}$ such as —$NH_2$. Another particular $R^6/R^7$ combination is where $R^6$ is —H, and $R^7$ is —$X^7R^{7a}$, where $X^7$ is —$S(O_2)$—, and $R^{7a}$ is —$C_{1-5}$alkyl (e.g., methyl, ethyl, n-propyl, isopropyl, or n-butyl), heteroaryl (e.g., thiophen-2-yl or 8-quinolinyl), or aryl (e.g., 4-trifluoromethylphenyl, 2-fluorophenyl, 2,6-dichlorophenyl, 4-methylphenyl, or phenyl). Another particular $R^6/R^7$ combination is where $R^6$ is —H, and $R^7$ is —$X^7R^{7a}$, where $X^7$ is —$S(O_2)$—$C_{1-5}$alkylene such as —$S(O_2)(CH_2)_2$—, and $R^{7a}$ is —$NR^{7b}R^{7c}$ such as —$NHCH_3$.

Another particular $R^6/R^7$ combination is where $R^6$ is —$C_{1-5}$ alkyl such as methyl, and $R^7$ is: —$X^7R^{7a}$, where $X^7$ is —$C_{1-5}$alkylene such as —$(CH_2)_2$—, and $R^{7a}$ is —OH; —$X^7R^{7a}$, where $X^7$ is —$C_{1-5}$alkylene such as —$CH_2$—, and $R^{7a}$ is heteroaryl such as 3-pyridyl, 4-pyridyl, or 2-furyl; $X^7R^{7a}$, where $X^7$ is —$C_{1-5}$alkylene-C(O)— such as —$CH_2C(O)$—, and $R^{7a}$ is —OH; or $X^7R^{7a}$, where $X^7$ is —$C_{1-5}$alkylene-$S(O_2)$— such as —$(CH_2)_2S(O_2)$—, and $R^{7a}$ is —$C_{1-5}$alkyl such as methyl. Another particular $R^6/R^7$ combination is where $R^6$ and $R^7$ are different —$C_{1-5}$alkyl groups. For example, $R^6$ can be ethyl, and $R^7$ can be methyl or isopropyl.

Another particular $R^6/R^7$ combination is where $R^6$ and $R^7$ are the same. $R^6$ and $R^7$ can both be a —$C_{1-5}$alkyl group such as methyl and ethyl. $R^6$ and $R^7$ can also both be a —$C_{1-5}$alkylene-$C_{1-5}$alkoxy group ($X^6$ and $X^7$ are —$C_{1-5}$alkylene, $R^{6a}$ and $R^{7a}$ are —$C_{1-5}$alkoxy), examples of which include —$(CH_2)_2OCH_3$ and —$(CH_2)_2OCH_2CH_3$. $R^6$ and $R^7$ can also both be a —$C_{1-5}$alkylene-OH group ($X^6$ and $X^7$ are —$C_{1-5}$alkylene, $R^{6a}$ and $R^{7a}$ are —OH), an example of which includes —$(CH_2)_2OH$.

Alternately, $R^6$ and $R^7$ may be taken together to form a thiomorpholine 1,1-dioxide ring:

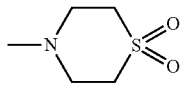

$R^6$ and $R^7$ may also be taken together to form morpholin-4-yl:

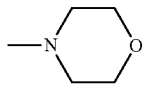

which may be substituted with one, two or three —$C_{1-5}$alkyl groups. In one embodiment, the morpholine ring is substituted with two —$C_{1-5}$alkyl groups such as methyl, for example 2,6-dimethylmorpholin-4-yl. In addition, $R^6$ and $R^7$ may also be taken together to form:

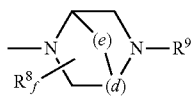

The value for d is 1 or 2. In one embodiment, d is 1. The value for e is 0, 1 or 2. In one embodiment, e is 0 and in another embodiment e is 1. In one embodiment, d is 1 and e is 0 or 1. The value for f is 0, 1, 2 or 3. In one embodiment, f is 0. $R^8$ is selected from —$C_{1-5}$alkyl and =O. In one embodiment, $R^8$ is =O. In addition, each alkyl group in $R^8$ is optionally substituted with 1 to 5 fluoro substituents.

$R^9$ is selected from —H, —$C_{1-5}$alkyl, hydroxyphenyl, heteroaryl, and —$X^9R^{9a}$. $X^9$ is selected from —$C_{1-5}$alkylene, —C(O)—, —$C_{1-5}$alkylene-C(O)—, —C(O)—$C_{1-5}$alkylene, —S(O$_2$)—, —$C_{1-5}$alkylene-S(O$_2$)—, and —S(O$_2$)—$C_{1-5}$alkylene. $R^{9a}$ is selected from —H, —OH, —$C_{1-5}$alkyl, —$C_{1-5}$alkoxy, aryl, heteroaryl, heterocyclyl, and —$NR^{9b}R^{9c}$ ($R^{9b}$ and $R^{9c}$ are independently —H or —$C_{1-5}$alkyl). In addition, each alkyl and alkoxy group in $R^9$ and $R^{9a-c}$ is optionally substituted with 1 to 5 fluoro substituents.

In one embodiment, $R^9$ is —H or hydroxyphenyl. $R^9$ can also be —$C_{1-5}$alkyl such as ethyl and isopropyl. In another embodiment, $R^9$ is heteroaryl such as 4-pyridyl. In another embodiment, $R^9$ is —$X^9R^{9a}$, where $X^9$ is —$C_{1-5}$alkylene such as —$CH_2$—, and $R^{9a}$ is heteroaryl such as 4-pyridyl, or where $X^9$ is —$C_{1-5}$alkylene such as —$(CH_2)_2$—, and $R^{9a}$ is —$C_{1-5}$alkoxy such as —$OCH_3$. $R^9$ can also be —$X^9R^{9a}$, where $X^9$ is —C(O)—, and $R^{9a}$ is: —H; —$C_{1-5}$alkyl such as methyl; —$C_{1-5}$alkoxy such as —$OCH_3$; heterocyclyl such as 1-pyrrolidinyl, 1-piperidyl, and 4-morpholinyl; or —$NR^{9b}R^{9c}$ such as —$N(CH_3)_2$. In another embodiment, $R^9$ is —$X^9R^{9a}$, where $X^9$ is —$C_{1-5}$alkylene-C(O)— such as —$CH_2C(O)$—, and $R^{9a}$ is heterocyclyl such as 1-pyrrolidinyl, or —$NR^{9b}R^{9c}$ such as —$N(CH_3)_2$. $R^9$ can also be —$X^9R^{9a}$, where $X^9$ is —S(O$_2$)—, and $R^{9a}$ is —$C_{1-5}$alkyl such as methyl and ethyl.

In one embodiment, d is 1, e is 0, and f is 1, i.e., $R^6$ and $R^7$ are taken together to form a piperidine ring. Particular embodiments of the piperidine ring include those where $R^8$ is =O and $R^9$ is —H, for example, a piperazin-2-one ring.

In one embodiment, d is 1, and e and f are 0, i.e., $R^6$ and $R^7$ are taken together to form a piperidine ring. Particular embodiments of the piperidine ring include those where $R^9$ is: —$C_{1-5}$alkyl such as ethyl and isopropyl; hydroxyphenyl; heteroaryl such as 4-pyridyl; —$X^9R^{9a}$, where $X^9$ is —$C_{1-5}$alkylene such as —$CH_2$—, and $R^{9a}$ is heteroaryl such as 4-pyridyl; —$X^9R^{9a}$, where $X^9$ is —$C_{1-5}$alkylene such as —$(CH_2)_2$—, and $R^{9a}$ is —$C_{1-5}$alkoxy such as —$OCH_3$; —$X^9R^{9a}$, where $X^9$ is —C(O)—, and $R^{9a}$ is —H, —$C_{1-5}$alkyl such as methyl, —$C_{1-5}$alkoxy such as —$OCH_3$, heterocyclyl such as 1-pyrrolidinyl, 1-piperidyl, and 4-morpholinyl, or —$NR^{9b}R^{9c}$ such as —$N(CH_3)_2$; —$X^9R^{9a}$, where $X^9$ is —$C_{1-5}$alkylene-C(O)— such as —$CH_2C(O)$—, and $R^{9a}$ is heterocyclyl such as 1-pyrrolidinyl, or —$NR^{9b}R^{9c}$ such as —$N(CH_3)_2$; and —$X^9R^{9a}$, where $X^9$ is —S(O$_2$)—, and $R^{9a}$ is —$C_{1-5}$alkyl such as methyl and ethyl.

In one embodiment, d is 2, and e and f are 0, i.e., $R^6$ and $R^7$ are taken together to form a [1,4]diazepane ring. Particular embodiments of the [1,4]diazepane ring include those where $R^9$ is —$X^9R^{9a}$, where $X^9$ is —C(O)—, and $R^{9a}$ is —$C_{1-5}$alkyl such as methyl. In another embodiment, d and e are 1, and f is 0, i.e., $R^6$ and $R^7$ are taken together to form a 2,5-diaza-bicyclo[2.2.1]heptane ring. Particular embodiments of the 2,5-diaza-bicyclo[2.2.1]heptane ring include those where $R^9$ is: —H; or —$X^9R^{9a}$, where $X^9$ is —$C_{1-5}$alkylene such as —$CH_2$—, and $R^{9a}$ is aryl such as phenyl.

A particular group of compounds of interest are compounds of formula I wherein a, b, and c are 0. Another group of compounds of interest are compounds of formula I wherein W is —O—. A particular group of compounds of interest are compounds of formula I where m is 0 and t is 1. A particular group of compounds of interest are compounds of formula I where Z is —NHC(O)—, —N(CH$_3$)C(O)—, or —C(O)NH—. Other compounds of interest include those where Ar is phenylene, phenylene substituted with methoxy, pyridylene, thienylene, pyrrolylene, or furylene, and in particular where Ar is phen-1,3-ylene, phen-1,4-ylene, 2-methoxyphen-1,4-ylene, 2,5-pyridylene, 2,5-thienylene, 2,4-pyrrolylene, 2,5-pyrrolylene, or 2,5-furylene.

Combinations of the foregoing are also of interest. For example, one group of compounds of interest are compounds of formula I wherein m is 0, t is 1, and W is —O—. These compounds can also be depicted by formula Ia:

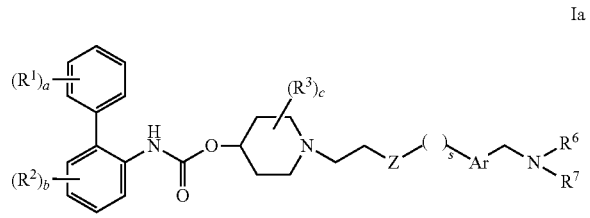

where a, b, c, s, R", $R^{6-7}$, Z, and Ar, are as defined for formula I. Another example of a group of compounds of interest are compounds of formula Ia wherein a, b, and c are 0; Z is selected from —NHC(O)—, —N(CH$_3$)C(O)—, and —C(O)NH—; and Ar is selected from phenylene, phenylene substituted with methoxy, pyridylene, thienylene, pyrrolylene, and furylene.

In addition, particular compounds of formula I that are of interest include:

biphenyl-2-yl-carbamic acid 1-(2-{[4-(4-acetylpiperazin-1-ylmethyl)benzoyl]methylamino}ethyl)piperidin-4-yl ester;

biphenyl-2-ylcarbamic acid 1-{2-[(4-aminomethylbenzoyl)methylamino]ethyl}piperidin-4-yl ester;

biphenyl-2-ylcarbamic acid 1-{2-[(4-{[(furan-2-carbonyl)amino]methyl}benzoyl)methylamino]ethyl}piperidin-4-yl ester;

biphenyl-2-ylcarbamic acid 1-(2-{[4-(acetylaminomethyl)benzoyl]methylamino}ethyl)piperidin-4-yl ester;

biphenyl-2-ylcarbamic acid 1-{2-[methyl-(4-{[(pyridine-4-carbonyl)amino]methyl}benzoyl)amino]ethyl}piperidin-4-yl ester;

biphenyl-2-ylcarbamic acid 1-[2-({-4-[(cyclopropanecarbonylamino)methyl]benzoyl}methylamino)ethyl]piperidin-4-yl ester;

biphenyl-2-ylcarbamic acid 1-{2-[methyl-(4-{[(thiophene-2-carbonyl)amino]methyl}benzoyl)amino]ethyl}piperidin-4-yl ester;

biphenyl-2-ylcarbamic acid 1-[2-({4-[(cyclobutanecarbonylamino)methyl]benzoyl}methylamino)ethyl]piperidin-4-yl ester;

biphenyl-2-ylcarbamic acid 1-(2-{[4-(isopropylaminomethyl)benzoyl]methylamino}ethyl)piperidin-4-yl ester;

biphenyl-2-ylcarbamic acid 1-[2-({4-[(cyclopropylmethylamino)methyl]benzoyl}methylamino)ethyl]piperidin-4-yl ester;

biphenyl-2-ylcarbamic acid 1-{2-[methyl-(4-morpholin-4-ylmethylbenzoyl)amino]ethyl}piperidin-4-yl ester;

biphenyl-2-ylcarbamic acid 1-{2-[(4-{[(2-methanesulfonylethyl)methylamino]methyl}benzoyl)methylamino]ethyl}piperidin-4-yl ester;

biphenyl-2-ylcarbamic acid 1-(2-{[4-(4-ethylpiperazin-1-ylmethyl)benzoyl]methylamino}ethyl)piperidin-4-yl ester;

biphenyl-2-ylcarbamic acid 1-(2-{[4-(4-isopropylpiperazin-1-ylmethyl)benzoyl]methylamino}ethyl)piperidin-4-yl ester;

biphenyl-2-ylcarbamic acid 1-[2-({4-[(ethylisopropylamino)methyl]benzoyl}methylamino)ethyl]piperidin-4-yl ester;

biphenyl-2-ylcarbamic acid 1-(2-{[4-(2,6-dimethylmorpholin-4-ylmethyl)benzoyl]methylamino}ethyl)piperidin-4-yl ester;

biphenyl-2-ylcarbamic acid 1-{2-[(4-{[bis-(2-hydroxyethyl)amino]methyl}benzoyl)methylamino]ethyl}piperidin-4-yl ester;

biphenyl-2-ylcarbamic acid 1-(2-{[4-(tert-butylaminomethyl)benzoyl]methylamino}ethyl)piperidin-4-yl ester;

biphenyl-2-ylcarbamic acid 1-[2-({4-[(ethylmethylamino)methyl]benzoyl}methylamino)ethyl]piperidin-4-yl ester;

biphenyl-2-ylcarbamic acid 1-{2-[(4-{[bis-(2-ethoxyethyl)amino]methyl}benzoyl) methylamino]ethyl}piperidin-4-yl ester;

biphenyl-2-ylcarbamic acid 1-[2-(methyl-{4-[(methylpyridin-3-ylmethylamino) methyl]benzoyl}amino)ethyl]piperidin-4-yl ester;

biphenyl-2-ylcarbamic acid 1-{2-[(4-{[bis(2-methoxyethyl)amino]methyl}benzoyl)methylamino]ethyl}piperidin-4-yl ester;

biphenyl-2-ylcarbamic acid 1-{2-[(4-{[(2-hydroxyethyl)methylamino]methyl}benzoyl)methylamino]ethyl}piperidin-4-yl ester;

biphenyl-2-ylcarbamic acid 1-[2-(methyl-{4-[(methyl-pyridin-4-ylmethylamino) methyl]benzoyl}amino)ethyl]piperidin-4-yl ester;

biphenyl-2-ylcarbamic acid 1-[2-({4-[4-(2-methoxyethyl)piperazin-1-ylmethyl]benzoyl}methylamino)ethyl]piperidin-4-yl ester;

biphenyl-2-ylcarbamic acid 1-(2-{[4-(4-ethanesulfonylpiperazin-1-ylmethyl)benzoyl]methylamino}ethyl)piperidin-4-yl ester;

biphenyl-2-ylcarbamic acid 1-(2-{[4-(2,5-diaza-bicyclo[2.2.1]hept-2-ylmethyl)benzoyl]methylamino}ethyl)piperidin-4-yl ester;

biphenyl-2-ylcarbamic acid 1-[2-({4-[(2-hydroxyethylamino)methyl]benzoyl}methylamino)ethyl]piperidin-4-yl ester;

biphenyl-2-ylcarbamic acid 1-(2-{methyl-[4-(4-pyridin-4-ylpiperazin-1-ylmethyl)benzoyl]amino}ethyl)piperidin-4-yl ester;

biphenyl-2-ylcarbamic acid 1-(2-{[4-(4-dimethylcarbamoylmethylpiperazin-1-ylmethyl)benzoyl]methylamino}ethyl)piperidin-4-yl ester;

biphenyl-2-ylcarbamic acid 1-(2-{methyl-[4-(4-pyridin-4-ylmethylpiperazin-1-ylmethyl)benzoyl]amino}ethyl)piperidin-4-yl ester;

biphenyl-2-ylcarbamic acid 1-[2-(methyl-{4-[4-(2-oxo-2-pyrrolidin-1-ylethyl)piperazin-1-ylmethyl]benzoyl}amino)ethyl]piperidin-4-yl ester;

biphenyl-2-ylcarbamic acid 1-[2-({4-[(2-hydroxyethylamino)methyl]benzoyl}methylamino)ethyl]piperidin-4-yl ester;

biphenyl-2-ylcarbamic acid 1-{2-[(4-ethylaminomethylbenzoyl)methylamino]ethyl}piperidin-4-yl ester;

biphenyl-2-ylcarbamic acid 1-{2-[(4-cyclopropylaminomethylbenzoyl)methylamino]ethyl}piperidin-4-yl ester;

biphenyl-2-ylcarbamic acid 1-[2-({4-[(2-methoxyethylamino)methyl]benzoyl}methylamino)ethyl]piperidin-4-yl ester;

biphenyl-2-ylcarbamic acid 1-(2-{methyl-[4-(3-oxopiperazin-1-ylmethyl)benzoyl]amino}ethyl)piperidin-4-yl ester;

biphenyl-2-ylcarbamic acid 1-(2-{[4-(4-acetyl[1,4]diazepan-1-ylmethyl)benzoyl]methylamino}ethyl)piperidin-4-yl ester;

biphenyl-2-ylcarbamic acid 1-[2-({4-[4-(4-hydroxyphenyl)piperazin-1-ylmethyl]benzoyl}methylamino)ethyl]piperidin-4-yl ester;

biphenyl-2-ylcarbamic acid 1-[2-({4-[(carbamoylmethylamino)methyl]benzoyl}methylamino)ethyl]piperidin-4-yl ester;

biphenyl-2-ylcarbamic acid 1-(2-{[4-(4-dimethylcarbamoylpiperazin-1-ylmethyl)benzoyl]methylamino}ethyl)piperidin-4-yl ester;

biphenyl-2-ylcarbamic acid 1-[2-(methyl-{4-[4-(pyrrolidine-1-carbonyl)piperazin-1-ylmethyl]benzoyl}amino)ethyl]piperidin-4-yl ester;

biphenyl-2-ylcarbamic acid 1-[2-(methyl-{4-[4-(piperidine-1-carbonyl)piperazin-1-ylmethyl]benzoyl}amino)ethyl]piperidin-4-yl ester;

biphenyl-2-ylcarbamic acid 1-[2-(methyl-{4-[4-(morpholine-4-carbonyl)piperazin-1-ylmethyl]benzoyl}amino)ethyl]piperidin-4-yl ester;

biphenyl-2-ylcarbamic acid 1-[2-(4-aminomethylbenzoylamino)ethyl]piperidin-4-yl ester;

biphenyl-2-ylcarbamic acid 1-{2-[3-((1R,4R)-5-benzyl-2,5-diaza-bicyclo[2.2.1]hept-2-ylmethyl)benzylcarbamoyl]ethyl}piperidin-4-yl ester;

biphenyl-2-ylcarbamic acid 1-[2-(3-aminomethylbenzylcarbamoyl)ethyl]piperidin-4-yl ester;

biphenyl-2-ylcarbamic acid 1-[2-(3-{[(pyridin-4-ylmethyl)amino]methyl}benzylcarbamoyl)ethyl]piperidin-4-yl ester;
biphenyl-2-ylcarbamic acid 1-(2-{3-[(furan-2-ylmethylmethylamino)methyl]benzylcarbamoyl}ethyl)piperidin-4-yl ester;
{[3-({3-[4-(biphenyl-2-ylcarbamoyloxy)piperidin-1-yl]propionylamino}methyl)benzyl]methylamino}acetic acid;
biphenyl-2-ylcarbamic acid 1-[2-(3-cyclobutylaminomethylbenzylcarbamoyl)ethyl]piperidin-4-yl ester;
biphenyl-2-ylcarbamic acid 1-[2-(3-cyclopropylaminomethylbenzylcarbamoyl)ethyl]piperidin-4-yl ester;
biphenyl-2-ylcarbamic acid 1-[2-(3-morpholin-4-ylmethylbenzylcarbamoyl)ethyl]piperidin-4-yl ester;
biphenyl-2-ylcarbamic acid 1-[2-(3-methylaminomethylbenzylcarbamoyl)ethyl]piperidin-4-yl ester;
biphenyl-2-ylcarbamic acid 1-[2-(3-dimethylaminomethylbenzylcarbamoyl)ethyl]piperidin-4-yl ester;
biphenyl-2-ylcarbamic acid 1-(2-{methyl-[3-(4-methylaminomethylphenyl) propionyl]amino}ethyl)piperidin-4-yl ester;
biphenyl-2-ylcarbamic acid 1-(2-{[3-(4-ethylaminomethylphenyl)propionyl]methylamino}ethyl)piperidin-4-yl ester;
biphenyl-2-ylcarbamic acid 1-[2-(4-aminomethylphenylcarbamoyl)ethyl]piperidin-4-yl ester;
biphenyl-2-ylcarbamic acid 1-(2-{4-[(4-trifluoromethylbenzenesulfonylamino) methyl]phenylcarbamoyl}ethyl)piperidin-4-yl ester;
biphenyl-2-ylcarbamic acid 1-(2-{4-[(butane-1-sulfonylamino)methyl]phenylcarbamoyl}ethyl)piperidin-4-yl ester;
biphenyl-2-ylcarbamic acid 1-(2-{4-[(2-fluorobenzenesulfonylamino)methyl]phenylcarbamoyl}ethyl)piperidin-4-yl ester;
biphenyl-2-ylcarbamic acid 1-(2-{4-[(quinoline-8-sulfonylamino)methyl]phenylcarbamoyl}ethyl)piperidin-4-yl ester;
biphenyl-2-ylcarbamic acid 1-{2-[4-(ethanesulfonylaminomethyl)phenylcarbamoyl]ethyl}piperidin-4-yl ester;
biphenyl-2-ylcarbamic acid 1-(2-{-4-[(2,6-dichlorobenzenesulfonylamino)methyl]phenylcarbamoyl}ethyl)piperidin-4-yl ester;
biphenyl-2-ylcarbamic acid 1-(2-{4-[(toluene-4-sulfonylamino)methyl]phenylcarbamoyl}ethyl)piperidin-4-yl ester;
biphenyl-2-ylcarbamic acid 1-(2-{4-[(thiophene-2-sulfonylamino)methyl]phenylcarbamoyl}ethyl)piperidin-4-yl ester;
biphenyl-2-ylcarbamic acid 1-{2-[4-(benzenesulfonylaminomethyl)phenylcarbamoyl]ethyl}piperidin-4-yl ester;
biphenyl-2-ylcarbamic acid 1-{2-[4-(methanesulfonylaminomethyl)phenylcarbamoyl]ethyl}piperidin-4-yl ester;
biphenyl-2-ylcarbamic acid 1-{2-[4-(trifluoromethanesulfonylaminomethyl)phenylcarbamoyl]ethyl}piperidin-4-yl ester;
biphenyl-2-ylcarbamic acid 1-(2-{4-[(propane-1-sulfonylamino)methyl]phenylcarbamoyl}ethyl)piperidin-4-yl ester;
biphenyl-2-ylcarbamic acid 1-(2-{4-[(propane-2-sulfonylamino)methyl]phenylcarbamoyl}ethyl)piperidin-4-yl ester;
biphenyl-2-ylcarbamic acid 1-[2-(4-{[(pyridin-2-ylmethyl)amino]methyl}phenylcarbamoyl)ethyl]piperidin-4-yl ester;
biphenyl-2-ylcarbamic acid 1-[2-(4-{[(pyridin-3-ylmethyl)amino]methyl}phenylcarbamoyl)ethyl]piperidin-4-yl ester;
biphenyl-2-ylcarbamic acid 1-[2-(4-{[(pyridin-4-ylmethyl)amino]methyl}phenylcarbamoyl)ethyl]piperidin-4-yl ester;
biphenyl-2-ylcarbamic acid 1-[2-(4-{[(benzo[1,3]dioxol-5-ylmethyl)amino]methyl}phenylcarbamoyl)ethyl]piperidin-4-yl ester;
biphenyl-2-ylcarbamic acid 1-[2-(4-{[(1H-indol-7-ylmethyl)amino]methyl}phenylcarbamoyl)ethyl]piperidin-4-yl ester;
biphenyl-2-ylcarbamic acid 1-{2-[4-(isobutylaminomethyl)phenylcarbamoyl]ethyl}piperidin-4-yl ester;
biphenyl-2-ylcarbamic acid 1-[2-(4-{[(thiophen-2-ylmethyl)amino]methyl}phenylcarbamoyl)ethyl]piperidin-4-yl ester;
biphenyl-2-ylcarbamic acid 1-(2-{4-[(3,3,3-trifluoropropylamino)methyl]phenylcarbamoyl}ethyl)piperidin-4-yl ester;
biphenyl-2-ylcarbamic acid 1-(2-{4-[(2-methylaminoethanesulfonylamino)methyl]phenylcarbamoyl}ethyl)piperidin-4-yl ester;
biphenyl-2-ylcarbamic acid 1-{2-[3-(4-methylaminomethylphenyl)propionylamino]ethyl}piperidin-4-yl ester;
biphenyl-2-ylcarbamic acid 1-{2-[3-(4-ethylaminomethylphenyl)propionylamino]ethyl}piperidin-4-yl ester;
biphenyl-2-ylcarbamic acid 1-(2-{3-[4-(isopropylaminomethyl)phenyl]propionylamino}ethyl)piperidin-4-yl ester;
biphenyl-2-ylcarbamic acid 1-{2-[3-(4-cyclopropylaminomethylphenyl) propionylamino]ethyl}piperidin-4-yl ester;
biphenyl-2-ylcarbamic acid 1-[2-(3-{4-[(cyclopropylmethylamino)methyl]phenyl}propionylamino)ethyl]piperidin-4-yl ester;
biphenyl-2-ylcarbamic acid 1-{2-[3-(4-cyclopentylaminomethylphenyl) propionylamino]ethyl}piperidin-4-yl ester;
biphenyl-2-ylcarbamic acid 1-[2-(3-{4-[(2-hydroxyethylamino)methyl]phenyl}propionylamino)ethyl]piperidin-4-yl ester;
biphenyl-2-ylcarbamic acid 1-[2-(3-{4-[(2-methoxyethylamino)methyl]phenyl}propionylamino)ethyl]piperidin-4-yl ester;
biphenyl-2-ylcarbamic acid 1-(2-{3-[4-(4-acetyl-[1,4]diazepan-1-ylmethyl)phenyl]propionylamino}ethyl)piperidin-4-yl ester;
biphenyl-2-ylcarbamic acid 1-(2-{3-[4-(4-acetylpiperazin-1-ylmethyl)phenyl]propionylamino}ethyl)piperidin-4-yl ester;
biphenyl-2-ylcarbamic acid 1-[2-(3-{4-[(carbamoylmethylamino)methyl]phenyl}propionylamino)ethyl]piperidin-4-yl ester;
biphenyl-2-ylcarbamic acid 1-(2-{3-[4-(4-dimethylcarbamoylmethylpiperazin-1-ylmethyl)phenyl]propionylamino}ethyl)piperidin-4-yl ester;
4-[4-(2-{2-[4-(biphenyl-2-ylcarbamoyloxy)piperidin-1-yl]ethylcarbamoyl}ethyl)benzyl]piperazine-1-carboxylic acid methyl ester;
biphenyl-2-ylcarbamic acid 1-(2-{3-[4-(1,1-dioxo-1$\lambda^6$-thiomorpholin-4-ylmethyl)phenyl]propionylamino}ethyl)piperidin-4-yl ester;
biphenyl-2-ylcarbamic acid 1-{2-[3-(4-{[bis-(2-hydroxyethyl)amino]methyl}phenyl)propionylamino]ethyl}piperidin-4-yl ester;
biphenyl-2-ylcarbamic acid 1-(2-{3-[4-(4-dimethylcarbamoylpiperazin-1-ylmethyl)phenyl]propionylamino}ethyl)piperidin-4-yl ester;

biphenyl-2-ylcarbamic acid 1-[2-(3-{4-[4-(pyrrolidine-1-carbonyl)piperazin-1-ylmethyl]phenyl}propionylamino)ethyl]piperidin-4-yl ester;

biphenyl-2-ylcarbamic acid 1-[2-(3-{4-[4-(piperidine-1-carbonyl)piperazin-1-ylmethyl]phenyl}propionylamino)ethyl]piperidin-4-yl ester;

biphenyl-2-ylcarbamic acid 1-[2-(3-{4-[4-(morpholine-4-carbonyl)piperazin-1-ylmethyl]phenyl}propionylamino)ethyl]piperidin-4-yl ester;

biphenyl-2-ylcarbamic acid 1-{2-[2-(4-methylaminomethylphenyl)acetylamino]ethyl}piperidin-4-yl ester;

biphenyl-2-ylcarbamic acid 1-{2-[2-(4-ethylaminomethylphenyl)acetylamino]ethyl}piperidin-4-yl ester;

biphenyl-2-ylcarbamic acid 1-[2-(2-{-4-[(2-hydroxyethylamino)methyl]phenyl}acetylamino)ethyl]piperidin-4-yl ester;

biphenyl-2-ylcarbamic acid 1-[2-(2-{4-[(2-methoxyethylamino)methyl]phenyl}acetylamino)ethyl]piperidin-4-yl ester;

biphenyl-2-ylcarbamic acid 1-[2-(2-{4-[(carbamoylmethylamino)methyl]phenyl}acetylamino)ethyl]piperidin-4-yl ester;

biphenyl-2-ylcarbamic acid 1-(2-{2-[4-(4-dimethylcarbamoylpiperazin-1-ylmethyl)phenyl]acetylamino}ethyl)piperidin-4-yl ester;

biphenyl-2-ylcarbamic acid 1-{2-[(2-methoxy-4-methylaminomethylbenzoyl)methylamino]ethyl}piperidin-4-yl ester;

biphenyl-2-ylcarbamic acid 1-(2-{[2-methoxy-4-(3-oxopiperazin-1-ylmethyl)benzoyl]methylamino}ethyl)piperidin-4-yl ester;

biphenyl-2-ylcarbamic acid 1-[2-({4-[(2-hydroxyethylamino)methyl]-2-methoxybenzoyl}methylamino)ethyl]piperidin-4-yl ester;

biphenyl-2-ylcarbamic acid 1-[2-(2-methoxy-4-methylaminomethylbenzoylamino) ethyl]piperidin-4-yl ester;

biphenyl-2-ylcarbamic acid 1-{2-[2-methoxy-4-(3-oxopiperazin-1-ylmethyl)benzoylamino]ethyl}piperidin-4-yl ester;

biphenyl-2-ylcarbamic acid 1-(2-{4-[(2-hydroxyethylamino)methyl]-2-methoxybenzoylamino}ethyl)piperidin-4-yl ester;

biphenyl-2-ylcarbamic acid 1-{2-[methyl(5-methylaminomethylpyridine-2-carbonyl)amino]ethyl}piperidin-4-yl ester;

biphenyl-2-ylcarbamic acid 1-{2-[(5-diethylaminomethylpyridine-2-carbonyl)methylamino]ethyl}piperidin-4-yl ester;

biphenyl-2-ylcarbamic acid 1-[2-({5-[(2-hydroxyethylamino)methyl]pyridine-2-carbonyl}methylamino)ethyl]piperidin-4-yl ester;

biphenyl-2-ylcarbamic acid 1-{2-[methyl(5-morpholin-4-ylmethylpyridine-2-carbonyl)amino]ethyl}piperidin-4-yl ester;

biphenyl-2-ylcarbamic acid 1-{2-[(5-{[(furan-2-ylmethyl)amino]methyl}pyridine-2-carbonyl)methylamino]ethyl}piperidin-4-yl ester;

biphenyl-2-ylcarbamic acid 1-{2-[5-(4-formylpiperazin-1-ylmethyl)pyridine-2-carbonyl]methylamino}ethyl)piperidin-4-yl ester;

biphenyl-2-ylcarbamic acid 1-{2-[(5-{[bis-(2-hydroxyethyl)amino]methyl}pyridine-2-carbonyl)methylamino]ethyl}piperidin-4-yl ester;

biphenyl-2-ylcarbamic acid 1-(2-{methyl-[5-(3-oxo-piperazin-1-ylmethyl)pyridine-2-carbonyl]amino}ethyl)piperidin-4-yl ester;

biphenyl-2-ylcarbamic acid 1-(2-{[5-(4-acetyl-[1,4]diazepan-1-ylmethyl)pyridine-2-carbonyl]methylamino}ethyl)piperidin-4-yl ester;

biphenyl-2-ylcarbamic acid 1-(2-{[5-(4-acetylpiperazin-1-ylmethyl)pyridine-2-carbonyl]methylamino}ethyl)piperidin-4-yl ester;

biphenyl-2-ylcarbamic acid 1-(2-{[5-(4-methanesulfonylpiperazin-1-ylmethyl)pyridine-2-carbonyl]methylamino}ethyl)piperidin-4-yl ester;

4-[6-({2-[4-(biphenyl-2-ylcarbamoyloxy)piperidin-1-yl]ethyl}methylcarbamoyl)pyridin-3-ylmethyl]piperazine-1-carboxylic acid methyl ester;

biphenyl-2-ylcarbamic acid 1-{2-[methyl-(5-methylaminomethylthiophene-2-carbonyl)amino]ethyl}piperidin-4-yl ester;

biphenyl-2-ylcarbamic acid 1-{2-[(5-diethylaminomethylthiophene-2-carbonyl)methylamino]ethyl}piperidin-4-yl ester;

biphenyl-2-ylcarbamic acid 1-[2-({5-[(2-hydroxyethylamino)methyl]thiophene-2-carbonyl}methylamino)ethyl]piperidin-4-yl ester;

biphenyl-2-ylcarbamic acid 1-{2-[methyl-(5-morpholin-4-ylmethylthiophene-2-carbonyl)amino]ethyl}piperidin-4-yl ester;

biphenyl-2-ylcarbamic acid 1-{2-[(5-{[(furan-2-ylmethyl)amino]methyl}thiophene-2-carbonyl)methylamino]ethyl}piperidin-4-yl ester;

biphenyl-2-ylcarbamic acid 1-(2-{[5-(4-formylpiperazin-1-ylmethyl)thiophene-2-carbonyl]methylamino}ethyl)piperidin-4-yl ester;

biphenyl-2-ylcarbamic acid 1-{2-[(5-{[bis-(2-hydroxyethyl)amino]methyl}thiophene-2-carbonyl)methylamino]ethyl}piperidin-4-yl ester;

biphenyl-2-yl-carbamic acid 1-(2-{methyl-[5-(3-oxopiperazin-1-ylmethyl)thiophene-2-carbonyl]amino}ethyl)piperidin-4-yl ester;

biphenyl-2-ylcarbamic acid 1-(2-{[5-(4-acetyl-[1,4]diazepan-1-ylmethyl)thiophene-2-carbonyl]methylamino}ethyl)piperidin-4-yl ester;

4-[5-({2-[4-(biphenyl-2-ylcarbamoyloxy)piperidin-1-yl]ethyl}methylcarbamoyl)thiophen-2-ylmethyl]piperazine-1-carboxylic acid methyl ester;

biphenyl-2-ylcarbamic acid 1-(2-{[5-(1,1-dioxo-1$\lambda^6$-thiomorpholin-4-ylmethyl)thiophene-2-carbonyl]methylamino}ethyl)piperidin-4-yl ester;

biphenyl-2-ylcarbamic acid 1-(2-{[5-(4-acetylpiperazin-1-ylmethyl)thiophene-2-carbonyl]methylamino}ethyl)piperidin-4-yl ester;

biphenyl-2-ylcarbamic acid 1-(2-{[5-(4-methanesulfonylpiperazin-1-ylmethyl)thiophene-2-carbonyl]methylamino}ethyl)piperidin-4-yl ester;

biphenyl-2-ylcarbamic acid 1-{2-[(5-methylaminomethylthiophene-2-carbonyl)amino]ethyl}piperidin-4-yl ester;

biphenyl-2-ylcarbamic acid 1-[2-({5-[(2-hydroxyethylamino)methyl]thiophene-2-carbonyl}amino)ethyl]piperidin-4-yl ester;

biphenyl-2-ylcarbamic acid 1-{2-[methyl(4-methylaminomethyl-1H-pyrrole-2-carbonyl)amino]ethyl}piperidin-4-yl ester;

biphenyl-2-ylcarbamic acid 1-{2-[methyl-(5-methylaminomethyl-1H-pyrrole-2-carbonyl)amino]ethyl}piperidin-4-yl ester;

biphenyl-2-ylcarbamic acid 1-(2-{[5-(4-acetylpiperazin-1-ylmethyl)-1H-pyrrole-2-carbonyl]methylamino}ethyl)piperidin-4-yl ester;

biphenyl-2-ylcarbamic acid 1-[2-({5-[(2-hydroxyethylamino)methyl]-1H-pyrrole-2-carbonyl]methylamino)ethyl}piperidin-4-yl ester;
biphenyl-2-ylcarbamic acid 1-{2-[methyl(5-methylaminomethylfuran-2-carbonyl)amino]ethyl}piperidin-4-yl ester;
biphenyl-2-ylcarbamic acid 1-{2-[(5-diethylaminomethylfuran-2-carbonyl)methylamino]ethyl}piperidin-4-yl ester;
biphenyl-2-ylcarbamic acid 1-[2-({5-[(2-hydroxyethylamino)methyl]furan-2-carbonyl}methylamino)ethyl]piperidin-4-yl ester;
biphenyl-2-ylcarbamic acid 1-{2-[methyl(5-morpholin-4-ylmethylfuran-2-carbonyl)amino]ethyl}piperidin-4-yl ester;
biphenyl-2-ylcarbamic acid 1-{2-[(5-{[(furan-2-ylmethyl)amino]methyl}furan-2-carbonyl)methylamino]ethyl}piperidin-4-yl ester;
biphenyl-2-ylcarbamic acid 1-(2-{[5-(4-formylpiperazin-1-ylmethyl)furan-2-carbonyl]methylamino}ethyl)piperidin-4-yl ester;
biphenyl-2-ylcarbamic acid 1-{2-[(5-{[bis-(2-hydroxyethyl)amino]methyl}furan-2-carbonyl)methylamino]ethyl}piperidin-4-yl ester;
biphenyl-2-yl-carbamic acid 1-(2-{methyl-[5-(3-oxopiperazin-1-ylmethyl)furan-2-carbonyl]amino}ethyl)piperidin-4-yl ester;
biphenyl-2-ylcarbamic acid 1-(2-{[5-(4-acetyl[1,4]diazepan-1-ylmethyl)furan-2-carbonyl]ethylamino}ethyl)piperidin-4-yl ester;
4-[5-({2-[4-(biphenyl-2-ylcarbamoyloxy)piperidin-1-yl]ethyl}methylcarbamoyl) furan-2-ylmethyl]piperazine-1-carboxylic acid methyl ester;
biphenyl-2-ylcarbamic acid 1-(2-{[5-(1,1-dioxo-1$\lambda^6$-thiomorpholin-4-ylmethyl) furan-2-carbonyl] methylamino}ethyl)piperidin-4-yl ester;
biphenyl-2-ylcarbamic acid 1-(2-{[5-(4-acetylpiperazin-1-ylmethyl)furan-2-carbonyl]methylamino}ethyl)piperidin-4-yl ester;
biphenyl-2-ylcarbamic acid 1-(2-{[5-(4-methanesulfonylpiperazin-1-ylmethyl) furan-2-carbonyl] methylamino}ethyl)piperidin-4-yl ester;
biphenyl-2-yl-carbamic acid 1-{2-[(5-aminomethylfuran-2-carbonyl)amino]ethyl}piperidin-4-yl ester;
biphenyl-2-yl-carbamic acid 1-{2-[(5-methylaminomethylfuran-2-carbonyl)amino]ethyl}piperidin-4-yl ester; and
biphenyl-2-ylcarbamic acid 1-[2-({5-[(2-hydroxyethylamino)methyl]furan-2-carbonyl}amino)ethyl]piperidin-4-yl ester;
or a pharmaceutically acceptable salt or solvate thereof.

DEFINITIONS

When describing the compounds, compositions, methods and processes of the invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group.

When a specific number of carbon atoms is intended for a particular term used herein, the number of carbon atoms is shown preceding the term. For example, the term "(1-5C) alkyl" or "$C_{1-5}$alkyl" means an alkyl group having from 1 to 5 carbon atoms.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers, such as a solvate of a pharmaceutically acceptable salt of a stereoisomer of a compound of formula I.

The term "therapeutically effective amount" means an amount sufficient to effect treatment when administered to a patient in need of treatment. For example, a therapeutically effective amount for antagonizing a muscarinic receptor is that amount which will achieve the desired antagonizing effect. Similarly, a therapeutically effective amount for treating a pulmonary disorder is the amount that will achieve the desired therapeutic result, which may be disease prevention, amelioration, suppression or alleviation, as described below.

The term "treating" or "treatment" as used herein means the treating or treatment of a disease or medical condition (such as COPD) in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

General Synthetic Procedures

The biphenyl compounds of the invention can be prepared from readily available starting materials using the following general methods, the procedures set forth in the Examples, or by using other methods, reagents, and starting materials that are readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Functional groups which may be protected include, by way of example, carboxylic acid groups, amino groups, hydroxyl groups, thiol groups, carbonyl groups and the like. Protecting groups other than those illustrated in the procedures described herein may be used, if desired. Representative protecting groups for carboxylic acids include esters, amides and hydrazides; for amino groups, carbamates and amides; for hydroxyl groups, ethers and esters; for thiol groups, thioethers and thioesters; for carbonyl groups, acetals and ketals; and the like. Exemplary protecting groups are listed below, and other groups as well as details of their introduction and removal, are described in T. W. Greene and G. M. Wuts, *Protecting Groups in Organic Synthesis*, Third Edition, Wiley, New York, 1999, and references cited therein.

Amino-protecting groups are suitable for preventing undesired reactions at an amino group, and include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like. Carboxy-protecting groups are suitable for preventing undesired reactions at a carboxy group, and include, but are not limited to, esters, such as methyl, ethyl, tert-butyl, benzyl (Bn), p-methoxybenzyl (PMB), 9-fluoroenylmethyl (Fm), trimethylsilyl (TMS), tert-butyldimethylsilyl (TBS), diphenylmethyl (benzhydryl, DPM) and the like. Hydroxyl-protecting groups are suitable for preventing undesirable reactions at a hydroxyl group, and include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C) alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

By way of illustration, the compounds of formula I can be prepared by a process comprising:

(a) reacting a compound of formula II:

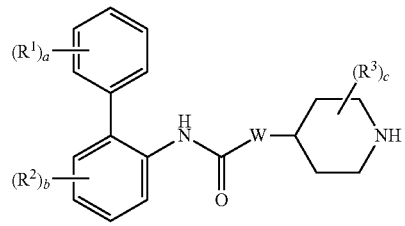

II or a salt thereof, with a compound of formula III:

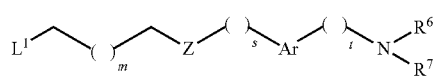

III wherein L¹ represents a leaving group; or (b) coupling a compound of formula IVa:

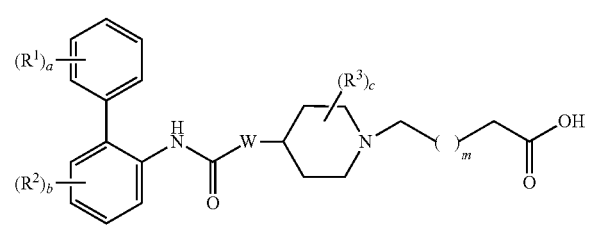

IVa or a reactive derivative thereof, with a compound of formula Va:

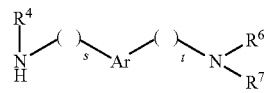

Va or coupling a compound of formula IVb:

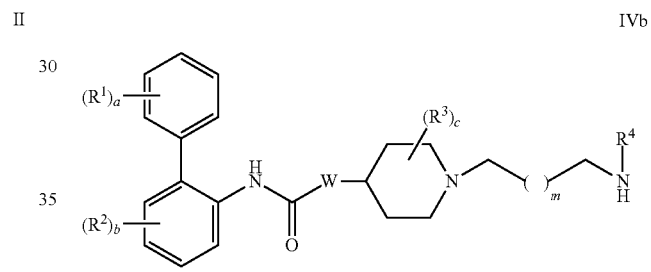

IVb with a compound of formula Vb:

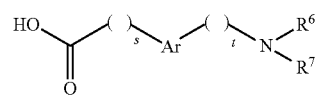

Vb or a reactive derivative thereof; or (c) reacting a compound of formula VI:

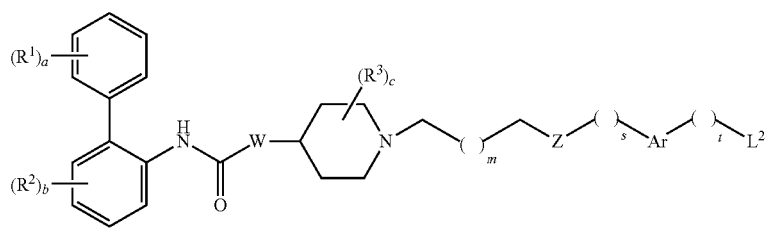

VI wherein $L^2$ represents a leaving group, with a compound of formula VII:

VII or (d) reacting a compound of formula II with a compound of formula VIII:

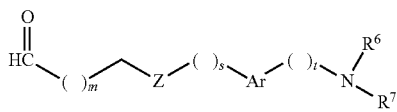

VIII in the presence of a reducing agent; or (e) reacting a compound of formula IX:

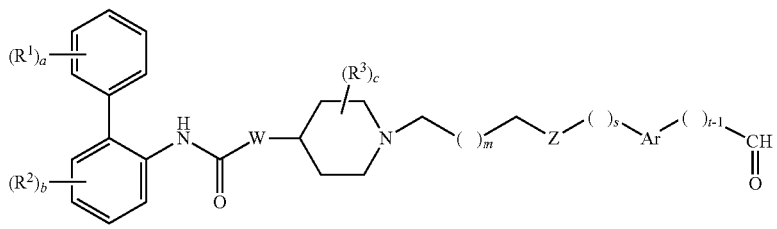

IX with a compound of formula VII in the presence of a reducing agent; and then (f) removing any protecting groups that may be present to provide a compound of formula I; and optionally, forming a pharmaceutically acceptable salt thereof.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

In process (a), the reaction between the compounds of formula II and III, the leaving represented by $L^1$ can be, for example, halo, such as chloro, bromo or iodo, or a sulfonic ester group, such as mesylate or tosylate. The reaction is conveniently performed in the presence of a base, for example, a tertiary amine such as diisopropylethylamine. Convenient solvents include nitriles, such as acetonitrile. The reaction is conveniently conducted at a temperature in the range of from 0° C. to 100° C.

Compounds of formula II are generally known in the art, or can be prepared by deprotecting a compound of formula X:

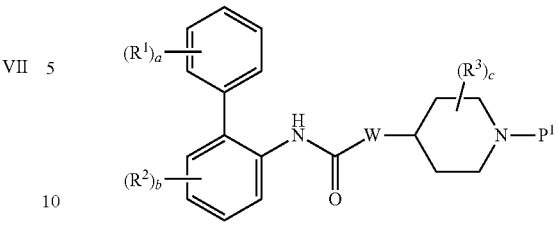

X wherein $P^1$ represents an amino-protecting group, such as a benzyl group. Benzyl groups are conveniently removed by reduction, using a hydrogen or ammonium formate and a Group VIII metal catalyst, such as palladium. When W represents $NW^a$, the hydrogenation is conveniently performed using Pearlman's catalyst ($Pd(OH)_2$).

Compounds of formula X can be prepared by reacting an isocyanate compound of formula XI with a compound of formula XII:

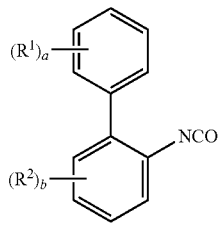

XI

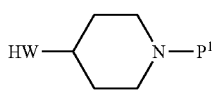

XII

Compounds of formula III can be prepared starting from a corresponding compound in which $L^1$ represents a hydroxyl group, for example, by reaction of a halogenating agent, such as thionyl chloride, to afford a compound of formula III in which $L^1$ represents halo, such as chloro. Compounds in which $L^1$ represents a hydroxyl group may be prepared, for example, by reacting a compound of formula Vb with an appropriate amino-substituted alcohol, such as 2-aminoethanol or 3-aminopropan-1-ol.

In process (b), the term "reactive derivative" of compound IVa or Vb is intended to mean that the carboxylic acid is activated, for example, by forming an anhydride or carboxylic acid halide, such as a carboxylic acid chloride. Alternatively, the carboxylic acid can be activated using conventional carboxylic acid/amine coupling reagents, such carbodiimides, O-(7-azabenzotriazol-1-yl-N,N,N',N' tetramethyluronium hexafluorophosphate (HATU) and the like. This reaction is conveniently performed under conventional amide bond-forming conditions. The process is conveniently conducted at a temperature in the range of from −10° C. to 100° C.

Compounds of formula IVa can be prepared by reacting a compound of formula II with a compound of formula XIII:

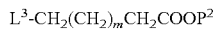

XIII wherein $L^3$ represents a leaving group including, for example, halo, such as chloro, bromo or iodo, or a sulfonic ester group, such as mesylate or tosylate; and $P^2$ represents a hydrogen atom or a carboxyl-protecting group, such as a (1-4C)alkyl group. If necessary, the carboxyl-protecting group $P^2$, is then removed, for example, by hydrolysis under conventional conditions, such as by using lithium hydroxide.

Compounds of formula Va can be prepared by reacting a compound of formula VII with a compound of formula XIV:

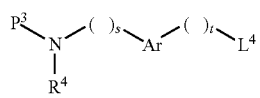

XIV wherein $P^3$ represents hydrogen or an amino-protecting group, such as tert-butoxycarbonyl, and $L^4$ represents a leaving group including, for example, halo, such as chloro, bromo or iodo, or a sulfonic ester group, such as mesylate or tosylate; followed if necessary, by removing an amino-protecting group $P^3$. Alternatively, such compounds can be prepared by reductive amination of a compound of formula XV:

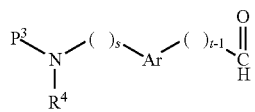

XV using a compound of formula VII. The reducing agent may be, for example, hydrogen in the presence of a Group VIII metal catalyst, such as palladium, or a metal hydride reducing agent, such as a borohydride, including sodium triacetoxyborohydride. Convenient solvents include alcohols, such as methanol. The reaction is conveniently performed at a temperature in the range of from 0° C. to 100° C.

Compounds of formula IVb can be prepared by reacting a compound of formula II with a compound of formula XVI:

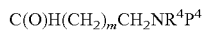

(XVI)

wherein $P^4$ represents hydrogen or an amino-protecting group, such as benzyl, in the presence of a reducing agent, such as sodium triacetoxyborohydride, followed if necessary by removing the amino-protecting group $P^4$ by, for example, hydrogenation in the presence of palladium.

Compounds of formula Vb can be prepared by reacting a compound of formula VII with a compound of formula XVII:

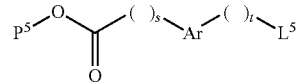

XVII wherein $P^5$ represents hydrogen or a carboxyl-protecting group, such as methyl or ethyl, and $L^5$ represents a leaving group, followed if necessary by removing the carboxyl protecting group $P^5$. Alternatively, such compounds can be prepared by reductive amination of a compound of formula XVIII with a compound of formula VII:

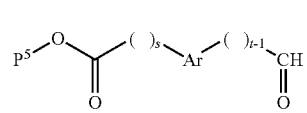

XVIII

The reducing agent may be, for example, hydrogen in the presence of a Group VIII metal catalyst, such as palladium, or a metal hydride reducing agent, such as a borohydride, including sodium triacetoxyborohydride. Convenient solvents include alcohols, such as methanol. The reaction is conveniently performed at a temperature in the range of from 0° C. to 100° C.

Referring to process (c), the leaving group represented by $L^2$ can be, for example, halo, such as chloro, bromo or iodo, or a sulfonic ester group, such as mesylate or tosylate. This reaction is conveniently performed in the presence of a base, for example, a tertiary amine such as diisopropylethylamine. Convenient solvents include nitriles, such as acetonitrile. The reaction is conveniently conducted at a temperature in the range of from 0° C. to 100° C. The compounds of formula VI can be prepared by reacting a compound of formula IVa with a compound of formula XIX:

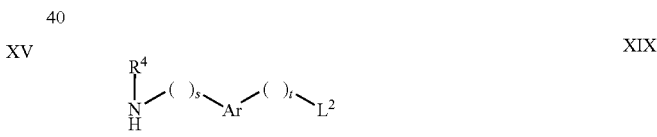

XIX or by reacting a compound of formula IVb with a compound of formula XX:

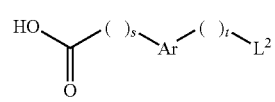

XX

The reaction is conveniently performed following, for example, the method of process (b) described herein. Compounds of formula VII are generally known or can be prepared from readily available starting materials using well-known synthetic methods.

In process (d), the reducing agent may be, for example, hydrogen in the presence of a Group VIII metal catalyst, such as palladium, or a metal hydride reducing agent, such as a borohydride, including sodium triacetoxyborohydride, optionally used in combination with a titanium tetraalkoxide, such as titanium tetraisopropoxide. Convenient solvents include alcohols, such as methanol and halogenated hydrocarbons, such as dichloromethane. The reaction is conveniently performed at a temperature in the range of from 0° C. to 100° C.

The compound of formula VIII may be prepared by oxidizing a compound corresponding to formula III in which $L^1$ represents a hydroxyl group. Such oxidation reactions can be conducted, for example, using sulfur dioxide pyridine complex in dimethylsulfoxide in the presence of a tertiary amine, such as diisopropylethylamine.

In process (e), the reduction is preformed as described for process (d).

Compounds of formula IX may be prepared by reacting a compound of formula IVb with a compound of formula XXI:

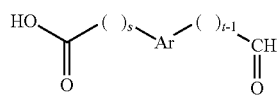

XXI in the presence of a carboxylic acid/amine coupling agent, such as 1-(3-dimethylaminopropyl)-3-ethylcarbodiimide (EDC) and 1-hydroxybenzotriazole hydrate (HOBT) and the like.

As will be apparent to those skilled in the art, compounds of formula I prepared by any of steps (a) to (f) herein may be further derivatized to form other compounds of formula I using methods and reagents well-known in the art. By way of illustration, a compound of formula I may be reacted with bromine to afford a corresponding compound of formula I in which $R^2$, for example, represents a bromo group. Additionally, a compound of formula I in which $R^4$ represents a hydrogen atom may be alkylated to afford a corresponding compound of formula I in which $R^4$ represents a (1-4C) alkyl group.

Further details regarding specific reaction conditions and other procedures for preparing representative compounds of the invention or intermediates thereof are described in the Examples set forth below.

Pharmaceutical Compositions and Formulations

The compounds of the invention are typically administered to a patient in the form of a pharmaceutical composition or formulation. Such compositions may be administered by any acceptable route of administration including, but not limited to, inhaled, oral, nasal, topical (including transdermal) and parenteral modes of administration. It will be understood that any form of the compound, i.e., free base, pharmaceutically acceptable salt, solvate, etc., that is suitable for the particular mode of administration can be used in the compositions described herein.

Accordingly, in one embodiment, the invention is directed to a pharmaceutical composition comprising a pharmaceutically acceptable carrier or excipient and a therapeutically effective amount of a compound of formula I, or a pharmaceutically acceptable salt or solvate or stereoisomer thereof. The pharmaceutical composition may contain other therapeutic and/or formulating agents if desired.

The compositions of the invention typically contain a therapeutically effective amount of a compound of formula I or a pharmaceutically acceptable salt or solvate or stereoisomer thereof, as the active agent. Typically, the composition will contain from about 0.01-95% by weight of the active agent; including, from about 0.01-30% by weight; such as from about 0.01-10% by weight of the active agent.

Any conventional carrier or excipient may be used in the compositions of the invention. The choice of a particular carrier or excipient, or combination of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar) buffering agents, such as magnesium hydroxide and aluminum hydroxide; (alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

The compositions of the invention are typically prepared by thoroughly and intimately mixing or blending a compound of formula I with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of the invention are suitable for inhaled administration. Suitable compositions for inhaled administration will typically be in the form of an aerosol or a powder, and are generally administered using well-known delivery devices, such as a nebulizer inhaler, a dry powder inhaler (DPI), a metered-dose inhaler (MDI) or similar delivery device.

In a specific embodiment of the invention, a pharmaceutical composition comprising the active agent is administered by inhalation using a nebulizer inhaler. Such nebulizer devices typically produce a stream of high velocity air that causes the composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are commercially available, for example, by PARI GmbH (Starnberg, German). Other nebulizer devices include Respimat (Boehringer Ingelheim) and those described, for example, in U.S. Pat. No. 6,123,068 to Lloyd et al. and WO 97/12687 (Eicher et al.), the disclosures of which are incorporated herein by reference in their entirety. A representative pharmaceutical composition for use in a nebulizer inhaler comprises an isotonic aqueous solution comprising from about 0.05 µg/mL to about 10 mg/mL of a compound of formula I or a pharmaceutically acceptable salt or solvate or stereoisomer thereof.

In another specific embodiment of the invention, a pharmaceutical composition comprising the active agent is administered by inhalation using a DPI. Such DPIs typically administer the active agent as a free-flowing powder that is dispersed in a patient's air-stream during inspiration. In order to achieve a free flowing powder, the active agent is typically formulated with a suitable excipient such as lactose or starch. Micronization is a common method of reducing crystal size to that suitable for pulmonary delivery. Typically, the active agent is micronized and combined with a suitable carrier to form a suspension of micronized particles of respirable size, where "micronized particles" or "micronized form" means at least about 90% of the particles have a diameter of less than about 10 µm. Other methods of reducing particle size may also be used such as fine milling, chopping, crushing, grinding, milling, screening, trituration, pulverization, and so forth, as long as the desired particle size can be obtained. A representative pharmaceutical composition for use in a DPI comprises dry lactose having a particle size between about 1 µm and about 100 µm and micronized particles of a compound of formula I, or a pharmaceutically acceptable salt or solvate or stereoisomer thereof. Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device. Examples of DPI delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.); Handihaler (Boehringer Ingelheim); and those described in U.S. Pat. Nos. 5,415,162 to Casper et al., 5,239,993 to Evans, and 5,715,810 to Armstrong et al., and references cited therein; the disclosures of which are incorporated herein by reference in their entirety.

In yet another specific embodiment of the invention, the pharmaceutical composition comprising the active agent is administered by inhalation using an MDI, which typically discharges a measured amount of the active agent or a pharmaceutically acceptable salt or solvate or stereoisomer thereof using compressed propellant gas. Accordingly, pharmaceutical compositions administered using an MDI typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Formulations containing HFAs are generally preferred due to concerns about chlorofluorocarbons affecting the ozone layer. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company), the disclosures of which are incorporated herein by reference in their entirety. A representative pharmaceutical composition for use in an MDI comprises from about 0.01-5% by weight of a compound of formula I, or a pharmaceutically acceptable salt or solvate or stereoisomer thereof; from about 0-20% by weight ethanol; and from about 0-5% by weight surfactant; with the remainder being an HFA propellant. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of MDI devices developed specifically for use with HFA propellants are described in U.S. Pat. Nos. 6,006,745 to Marecki and 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.). The disclosures of the aforementioned patents and publications are incorporated herein by reference in their entirety.

For additional examples of processes of preparing respirable particles, and formulations and devices suitable for inhalation dosing see U.S. Pat. Nos. 6,268,533 to Gao et al., 5,983,956 to Trofast, 5,874,063 to Briggner et al., and 6,221,398 to Jakupovic et al.; and WO 99/55319 (Glaxo Group Ltd.) and WO 00/30614 (AstraZeneca AB); the disclosures of which are incorporated herein by reference in their entirety.

In another embodiment, the pharmaceutical compositions of the invention are suitable for oral administration. Suitable compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, i.e., as capsules, tablets, pills and the like, the composition will typically comprise a compound of the invention as the active ingredient and one or more pharmaceutically acceptable carriers, such as sodium citrate or dicalcium phosphate. The solid dosage forms may also comprise one or more of the following: fillers or extenders, such as starches, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the compositions of the invention. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the compositions of the invention may also be formulated to provide slow or controlled release of the active ingredient using, by way of example, hydroxypropyl methyl cellulose in varying proportions; or other polymer matrices, liposomes and/or microspheres.

In addition, the compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the compositions of the invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The compounds of the invention can also be co-administered with other therapeutic agents. This combination therapy involves using a compound of the invention combined with one or more of these secondary agents, either formulated together (e.g., packaged together in a single formulation) or formulated separately (e.g., packaged as separate unit dosage forms). Methods of formulating multiple agents together in the same formulation or in separate unit dosage forms, are well known in the art. The secondary agents can be used in the form of pharmaceutically acceptable salts or solvates, and if appropriate, as optically pure stereoisomers.

The secondary therapeutic agent(s) can be selected from other bronchodilators (e.g., $PDE_3$ inhibitors, adenosine 2b modulators and $\beta_2$ adrenergic receptor agonists); anti-inflammatory agents (e.g., steroidal anti-inflammatory agents, such as corticosteroids; non-steroidal anti-inflammatory agents (NSAIDs), and $PDE_4$ inhibitors); other muscarinic receptor antagonists (i.e., anticholinergic agents); antiinfective agents (e.g., Gram positive and Gram negative antibiotics or antivirals); antihistamines; protease inhibitors; and afferent blockers (e.g., $D_2$ agonists and neurokinin modulators). One particular embodiment of the invention is directed to a composition comprising (a) a pharmaceutically acceptable carrier and a therapeutically effective amount of a compound of formula I or a pharmaceutically acceptable salt or solvate or stereoisomer thereof; and (b) a pharmaceutically acceptable carrier and a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of formula I and the agent are formulated together or separately. In another embodiment, (b) is a pharmaceutically acceptable carrier and a therapeutically effective amount of a $\beta_2$ adrenergic receptor agonist and a steroidal anti-inflammatory agent.

Representative $\beta_2$ adrenergic receptor agonists include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of the invention include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds disclosed in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds disclosed in WO 02/070490 (Glaxo Group Ltd.); 3-(4-{[6-({(2R)-2-[3-(formylamino)-4-hydroxyphenyl]-2-hydroxyethyl}amino)hexyl]oxy}butyl)-benzenesulfonamide, 3-(4-{[64 {(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl)benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[64 {(2R/S)-2-[3-(formylamino)-4-hydroxyphenyl]-2-hydroxyethyl}amino) hexyl]-oxy}butyl) benzenesulfonamide and related compounds disclosed in WO 02/076933 (Glaxo Group Ltd.); 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439 (Glaxo Group Ltd.); N-{2-[4-(R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-(R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05-500 μg per dose. The disclosures of the aforementioned patents and publications are incorporated herein by reference in their entirety.

Representative steroidal anti-inflammatory agents include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05-500 μg per dose.

An exemplary combination is a compound of formula I, or pharmaceutically acceptable salt or solvate or stereoisomer thereof, co-administered with salmeterol as the $\beta_2$ adrenergic receptor agonist, and fluticasone propionate as the steroidal anti-inflammatory agent. Another exemplary combination is a compound of formula I, or pharmaceutically acceptable salt or solvate or stereoisomer thereof, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent.

Other suitable combinations include, for example, other anti-inflammatory agents, e.g., NSAIDs (such as sodium cromoglycate; nedocromil sodium; phosphodiesterase (PDE) inhibitors (e.g., theophylline, PDE4 inhibitors or mixed PDE3/PDE4 inhibitors); leukotriene antagonists (e.g., monteleukast); inhibitors of leukotriene synthesis; iNOS inhibitors; protease inhibitors, such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

Representative phosphodiesterase-4 (PDE4) inhibitors or mixed PDE3/PDE4 inhibitors include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of the invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Unless otherwise indicated, exemplary suitable doses for the other therapeutic agents administered in combination with a compound of the invention are in the range of about 0.05 μg/day to about 100 mg/day.

The following formulations illustrate representative compositions of the invention, as well as exemplary methods of preparation. One or more secondary agents can optionally be formulated with the compound of the invention (primary active agent). Alternately, the secondary agents(s) can be formulated separately and co-administered with the primary active agent, either simultaneously or sequentially. For example, in one embodiment, a single dry powder formulation can be manufactured to include both the compound of the invention and one or more secondary agents. In another embodiment, one formulation is manufactured to contain the compound of the invention and separate formulation(s) are manufactured to contain the secondary agent(s). Such dry powder formulations can then be packaged in separate blister packs and administered with a single DPI device.

Exemplary Dry Powder Formulation for Administration by Inhalation 0.2 mg of a compound of the invention is micronized and then blended with 25 mg of lactose. The blended mixture is then loaded into a gelatin inhalation cartridge. The contents of the cartridge are administered using a powder inhaler.

Exemplary Dry Powder Formulation for Administration by a Dry Powder Inhaler

A dry powder is prepared having a bulk formulation ratio of micronized compound of the invention (active agent) to lactose of 1:200. The powder is packed into a dry powder inhalation device capable of delivering between about 10 µg and 100 µg of active agent per dose.

Exemplary Formulations for Administration by a Metered Dose Inhaler

A suspension containing 5 wt % of a compound of the invention (active agent) and 0.1 wt % lecithin is prepared by dispersing 10 g of the active agent as micronized particles with a mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

Alternately, a suspension containing 5 wt % of the active agent, 0.5 wt % lecithin, and 0.5 wt % trehalose is prepared by dispersing 5 g of the active agent as micronized particles with a mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

Exemplary Aqueous Aerosol Formulation for Administration by Nebulizer

A pharmaceutical composition is prepared by dissolving 0.5 mg of a compound of the invention (active agent) in 1 mL of a 0.9% sodium chloride solution acidified with citric acid. The mixture is stirred and sonicated until the active agent is dissolved. The pH of the solution is adjusted to a value in the range of from 3 to 8 (typically about 5) by the slow addition of NaOH.

Exemplary Hard Gelatin Capsule Formulation for Oral Administration

The following ingredients are thoroughly blended and then loaded into a hard gelatin capsule: 250 mg of a compound of the invention, 200 mg of lactose (spray-dried), and 10 mg of magnesium stearate, for a total of 460 mg of composition per capsule.

Exemplary Suspension Formulation for Oral Administration

The following ingredients are mixed to form a suspension containing 100 mg of active ingredient per 10 mL of suspension.

| Ingredients | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Exemplary Injectable Formulation

The following ingredients are blended and the pH is adjusted to 4±0.5 using 0.5 N HCl or 0.5 N NaOH.

| Ingredients | Amount |
|---|---|
| Compound of the invention | 0.2 g |
| Sodium acetate buffer solution (0.4M) | 2.0 mL |
| HCl (0.5N) or NaOH (0.5N) | q.s. to pH 4 |
| Water (distilled, sterile) | q.s. to 20 mL |

Utility

The compounds of the invention are expected to be useful as muscarinic receptor antagonists and therefore, are expected to be useful for treating medical conditions mediated by muscarinic receptors, i.e., medical conditions which are ameliorated by treatment with a muscarinic receptor antagonist. These medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; cardiac arrhythmias, such as sinus bradycardia; Parkinson's disease; cognitive disorders, such as Alzheimer's disease; dismenorrhea; and the like.

In one embodiment, the compounds of the invention are useful for treating smooth muscle disorders in mammals, including humans and their companion animals (e.g., dogs, cats etc.). Smooth muscle disorders include, by way of illustration, overactive bladder, chronic obstructive pulmonary disease and irritable bowel syndrome. When used to treat smooth muscle disorders or other conditions mediated by muscarinic receptors, the compounds of the invention will typically be administered orally, rectally, parenterally or by inhalation in a single daily dose or in multiple doses per day. The amount of active agent administered per dose or the total amount administered per day will typically be determined by the patient's physician and will depend on factors such as the nature and severity of the patients condition, the condition being treated, age and general health of the patient, tolerance of the patient to the active agent, route of administration and the like.

Typically, suitable doses for treating smooth muscle disorders or other disorders mediated by muscarinic receptors will range from about 0.14 μg/kg/day to about 7 mg/kg/day of active agent; including from about 0.15 μg/kg/day to about 5 mg/kg/day. For an average 70 kg human, this would amount to about 10 μg per day to about 500 mg per day of active agent.

In a specific embodiment, the compounds of the invention are useful for treating pulmonary or respiratory disorders, such as COPD or asthma, in mammals including humans. When used to treat such disorders, the compounds of the invention will typically be administered by inhalation in multiple doses per day, in a single daily dose or a single weekly dose. Generally, the dose for treating a pulmonary disorder will range from about 10-200 mg/day. As used herein, COPD includes chronic obstructive bronchitis and emphysema (see, for example, Barnes, Chronic Obstructive Pulmonary Disease, *N Engl J Med* 343:269-78 (2000)). When used to treat a pulmonary disorder, the compounds of the invention are optionally administered in combination with other therapeutic agents such as a β$_2$-adrenoreceptor agonist; a corticosteroid, a non-steroidal anti-inflammatory agent, or combinations thereof.

When administered by inhalation, the compounds of the invention typically have the effect of producing bronchodilation. Accordingly, in another embodiment, the invention is directed to a method of producing bronchodilation in a patient, the method comprising administering to a patient a bronchodilation-producing amount of a compound of the invention. Generally, the therapeutically effective dose for producing bronchodilation will range from about 10-200 μg/day.

In another embodiment, the compounds of the invention are used to treat overactive bladder. When used to treat overactive bladder, the compounds of the invention will typically be administered orally in a single daily dose or in multiple doses per day; preferably in a single daily dose. Preferably, the dose for treating overactive bladder will range from about 1.0-500 mg/day.

In yet another embodiment, the compounds of the invention are used to treat irritable bowel syndrome. When used to treat irritable bowel syndrome, the compounds of the invention will typically be administered orally or rectally in a single daily dose or in multiple doses per day. Preferably, the dose for treating irritable bowel syndrome will range from about 1.0-500 mg/day.

Since compounds of the invention are muscarinic receptor antagonists, such compounds are also useful as research tools for investigating or studying biological systems or samples having muscarinic receptors. Such biological systems or samples may comprise $M_1$, $M_2$, $M_3$, $M_4$ and/or $M_5$ muscarinic receptors. Any suitable biological system or sample having muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like. In one embodiment, a biological assay is conducted by contacting a biological system or sample (comprising a muscarinic receptor) with a muscarinic receptor-antagonizing amount of a compound of the invention. The effects of antagonizing the muscarinic receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio)triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.). A compound of the invention will antagonize or decrease the activation of muscarinic receptors in any of the functional assays listed above, or assays of a similar nature. A muscarinic receptor-antagonizing amount of a compound of the invention will typically range from about 0.1-100 nanomolar.

Additionally, the compounds of the invention can be used as research tools for discovering and evaluating new compounds that have muscarinic receptor antagonist activity. In one embodiment, a method of evaluating a test compound in a biological assay, comprises: (a) conducting a biological assay with a test compound to provide a first assay value; (b) conducting the biological assay with a compound of formula I to provide a second assay value; wherein step (a) is conducted either before, after or concurrently with step (b); and (c) comparing the first assay value from step (a) with the second assay value from step (b). Exemplary biological assays include, by way of illustration and not limitation, a muscarinic receptor binding assay or a bronchoprotection assay in a mammal. For example, muscarinic receptor binding data (e.g., as determined by in vitro radioligand displacement assays) for a test compound or a group of test compounds can be compared to the muscarinic receptor binding data for a compound of the invention to identify those test compounds that have about equal or superior muscarinic receptor binding, if any. This aspect of the invention includes, as separate embodiments, both the generation of comparison data (using the appropriate assays) and the analysis of the test data to identify test compounds of interest.

In another embodiment, the compounds of the invention are used to antagonize a muscarinic receptor in a biological system, and a mammal in particular, such as mice, rats, guinea pigs, rabbits, dogs, pigs, humans and so forth. A therapeutically effective amount of a compound of formula I is administered to the mammal, and the effects of antagonizing the muscarinic receptor can then determined using conventional procedures and equipment, examples of which are described above.

Among other properties, compounds of formula I have been found to be potent inhibitors of $M_3$ muscarinic receptor activity. Accordingly, in a specific embodiment, the invention is directed to those compounds having an inhibition dissociation constant ($K_i$) for the $M_3$ receptor subtype of less than or equal to 10 nM; preferably, less than or equal to 5 nM; (as determined, for example, by an in vitro radioligand displacement assay). Additionally, compounds of formula I are expected to possess a desirable duration of action. Accordingly, in another specific embodiment, the invention is directed to those compounds having a duration of action greater than or equal to about 24 hours. Moreover, compounds of the invention are also expected to possess reduced side effects, such as dry mouth, at efficacious doses when administered by inhalation compared to other known muscarinic receptor antagonists administered by inhalation (such as tiotropium).

These properties, as well as the utility of the compounds of the invention, can be demonstrated using various in vitro and in vivo assays well-known to those skilled in the art. For example, representative assays are described in further detail in the following Examples.

EXAMPLES

The following Preparations and Examples illustrate specific embodiments of the invention. In these examples, the following abbreviations have the following meanings:

| | |
|---|---|
| AC | adenylyl cyclase |
| ACh | acetylcholine |
| ACN | acetonitrile |
| BOC | tert-butoxycarbonyl |
| BSA | bovine serum albumin |
| cAMP | 3'-5' cyclic adenosine monophosphate |
| CHO | Chinese hamster ovary |
| cM$_5$ | cloned chimpanzee M$_5$ receptor |
| DCM | dichloromethane (i.e., methylene chloride) |
| DIPEA | N,N-diisopropylethylamine |
| DMSO | dimethyl sulfoxide |
| dPBS | Dulbecco's phosphate buffered saline |

-continued

| | |
|---|---|
| DMAP | 4-dimethylaminopyridine |
| DMF | dimethylformamide |
| DMSO | dimethyl sulfoxide |
| EDC | 1-ethyl-3-(3-dimethylaminopropyl)carbodiimide |
| EDCI | 1-ethyl-3-(3-dimethylaminopropyl)carbodiimide hydrochloride |
| EtOAc | ethyl acetate |
| EtOH | ethanol |
| FBS | fetal bovine serum |
| FLIPR | fluorometric imaging plate reader |
| HATU | O-(7-azabenzotriazol-1-yl-N,N,N',N'-tetramethyluronium hexafluorophosphate |
| HBSS | Hank's buffered salt solution |
| HEPES | 4-(2-hydroxyethyl)-1-piperazineethanesulfonic acid |
| HOAt | 1-hydroxy-7-azabenzotriazole |
| hM$_1$ | cloned human M$_1$ receptor |
| hM$_2$ | cloned human M$_2$ receptor |
| hM$_3$ | cloned human M$_3$ receptor |
| hM$_4$ | cloned human M$_4$ receptor |
| hM$_5$ | cloned human M$_5$ receptor |
| HOAc | acetic acid |
| HOAt | 1-hydroxy-7-azabenzotriazole |
| HOBT | 1-hydroxybenzotriazole hydrate |
| HPLC | high-performance liquid chromatography |
| IPA | isopropanol |
| MCh | methylcholine |
| MeCN | methylcyanide |
| MeOH | methanol |
| NaBH(OAc)$_3$ | sodium triacetoxyborohydride |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with a Zorbax Bonus RP 2.1×50 mm column (Agilent) having a 3.5 micron particle size. Detection was by UV absorbance at 214 nm. The mobile phases employed were as follows (by volume): A is ACN (2%), water (98%) and TFA (0.1%); and B is ACN (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

Liquid chromatography mass spectrometry (LCMS) data were obtained with an Applied Biosystems (Foster City, Calif.) Model API-150EX instrument. LCMS 10-90 data was obtained using 10 to 90% Mobile Phase B over a 5 minute gradient. Small-scale purification was conducted using an API-150EX Prep Workstation system from Applied Biosystems. The mobile phases employed were as follows (by volume): A is water and 0.05% TFA; and B is ACN and 0.05% TFA. For arrays (typically about 3 to 50 mg recovered sample size) the following conditions were used: 20 mL/min flow rate; 15 minute gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 minute gradients and a 41.4 mm×250 mm Microsorb BDS column with 10 micron particles (Varian, Palo Alto, Calif.).

Preparation 1

Biphenyl-2-ylcarbamic Acid Piperidin-4-yl Ester

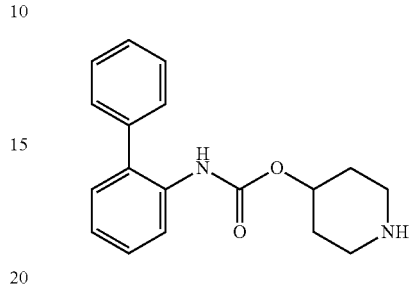

Biphenyl-2-isocyanate (97.5 g, 521 mmol) and 4-hydroxy-N-benzylpiperidine (105 g, 549 mmol) were heated together at 70° C. for 12 hours. The reaction mixture was then cooled to 50° C. and EtOH (1 L) was added and then 6M HCl (191 mL) was added slowly. The resulting mixture was then cooled to ambient temperature and ammonium formate (98.5 g, 1.56 mol) was added and then nitrogen gas was bubbled through the solution vigorously for 20 minutes. Palladium on activated carbon (20 g, 10 wt % dry basis) was then added and the reaction mixture was heated at 40° C. for 12 hours, and then filtered through a pad of Celite. The solvent was then removed under reduced pressure and 1M HCl (40 mL) was added to the crude residue. The pH of the mixture was then adjusted with 10 N NaOH to pH 12. The aqueous layer was extracted with EtOAc (2×150 mL) and the organic layer was dried over MgSO$_4$, filtered and the solvent removed under reduced pressure to give 155 g of the title intermediate (100% yield). HPLC (10-70) R$_f$=2.52; m/z: [M+H$^+$] calcd for C$_{18}$H$_{20}$N$_2$O$_2$, 297.15; found, 297.3.

Preparation 2

N-Benzyl-N-methylaminoacetaldehyde

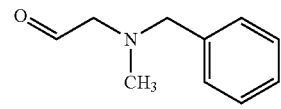

To a 3-necked 2-L flask was added N-benzyl-N-methylethanolamine (30.5 g, 0.182 mol), DCM (0.5 L), DIPEA (95 mL, 0.546 mol) and DMSO (41 mL, 0.728 mol). Using an ice bath, the mixture was cooled to about −10° C. and sulfur trioxide pyridine-complex (87 g, 0.546 mol) was added in 4 portions over 5 minute intervals. The reaction was stirred at −10° C. for 2 hours. Before removing the ice-bath, the reaction was quenched by adding water (0.5 L). The aqueous layer was separated and the organic layer was washed with water (0.5 L) and brine (0.5 L) and then dried over MgSO$_4$ and filtered to provide the title compound which was used without further purification.

Preparation 3

Biphenyl-2-ylcarbamic Acid
1-[2-(Benzylmethylamino)ethyl]piperidin-4-yl Ester

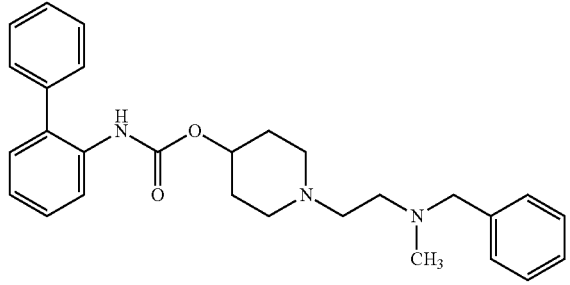 [SMILES: CN(CCN1CCC(OC(=O)Nc2ccccc2-c2ccccc2)CC1)Cc1ccccc1]

To a 2-L flask, containing N-benzyl-N-methylaminoacetaldehyde (19.8 g, 0.121 mol; prepared as described in Preparation 2) in DCM (0.5 L) was added biphenyl-2-ylcarbamic acid piperidin-4-yl ester (30 g, 0.101 mol; prepared as described in Preparation 1) followed by NaBH(OAc)$_3$ (45 g, 0.202 mol). The reaction mixture was stirred overnight and then quenched by the addition of 1N HCl (0.5 L) with vigorous stirring. Three layers were observed and the aqueous layer was removed. After washing with 1N NaOH (0.5 L), a homogenous organic layer was obtained which was then washed with a saturated solution of aqueous NaCl (0.5 L), dried over MgSO$_4$, filtered and the solvent removed under reduced pressure. The residue was purified by dissolving it in a minimal amount of IPA and cooling this solution to 0° C. to form a solid which was collected and washed with cool IPA to provide 42.6 g of the title intermediate (95% yield). MS m/z: [M+H$^+$] calcd f for $C_{28}H_{33}N_3O_2$, 444.3; found, 444.6. $R_f$=3.51 min (10-70 ACN: H$_2$O, reverse phase HPLC).

Preparation 3A

Biphenyl-2-ylcarbamic Acid
1-[2-(Benzylmethylamino)ethyl]piperidin-4-yl Ester

The title compound was prepared by mesylation of N-benzyl-N-methyl ethanolamine, which was then reacted with biphenyl-2-ylcarbamic acid piperidin-4-yl ester in an alkylation reaction.

A 500 mL flask (reactor flask) was charged with N-benzyl-N-methylethanolamine (24.5 mL), DCM (120 mL), NaOH (80 mL; 30 wt %) and tetrabutylammonium chloride. Mixing at low speed throughout the reaction, the mixture was cooled to −10° C. (cooling bath), and the addition funnel charged with DCM (30 mL) and mesyl chloride (15.85 mL), which was added drop wise at a constant rate over 30 minutes. The addition was exothermic, and stirring was continued for 15 minutes while the temperature equilibrated back to −10° C. The reaction was held for at least 10 minutes to ensure full hydrolysis of the excess mesyl chloride.

A 250 mL flask was charged with biphenyl-2-ylcarbamic acid piperidin-4-yl ester (26 g; prepared as described in Preparation 1) and DCM (125 mL), stirred for 15 minutes at room temperature, and the mixture chilled briefly to 10° C. to form a slurry. The slurry was then charged into the reactor flask via the addition funnel. The cooling bath was removed and the reaction mixture was warmed to 5° C. The mixture was transferred to a separatory funnel, the layers allowed to settle, and the aqueous layer removed. The organic layer was transferred back to the reactor flask, stirring resumed, the mixture held to room temperature, and the reaction monitored by HPLC for a total of 3.5 hours.

The reactor flask was charged with NaOH (1M solution; 100 mL), stirred, and the layers allowed to settle. The organic layer was separated, washed (NaCl satd. solution), its volume partially reduced under vacuum, and subjected to repeated IPA washings. The solids were collected and allowed to air-dry (25.85 g, 98% purity). Additional solids were obtained from further processing of the mother liquor (volume reduction, IPA, cooling).

Preparation 4

Biphenyl-2-ylcarbamic Acid
1-(2-Methylaminoethyl)piperidin-4-yl Ester

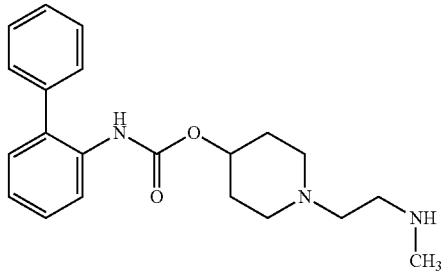 [SMILES: CNCCN1CCC(OC(=O)Nc2ccccc2-c2ccccc2)CC1]

To a Parr hydrogenation flask was added biphenyl-2-ylcarbamic acid 1-[2-(benzylmethylamino)ethyl]piperidin-4-yl ester (40 g, 0.09 mol; prepared as described in Preparation 3) and EtOH (0.5 L). The flask was flushed with nitrogen gas and palladium on activated carbon (15 g, 10 wt. % (dry basis), 37% wt/wt) was added along with HOAc (20 mL). The mixture was kept on the Parr hydrogenator under a hydrogen atmosphere (~50 psi) for 3 hours. The mixture was then filtered and washed with EtOH. The filtrate was condensed and the residue was dissolved in a minimal amount of DCM. Isopropyl acetate (10 volumes) was added slowly to form a solid which was collected to provide 22.0 g of the title intermediate (70% yield). MS m/z: [M+H$^+$] calcd for $C_{21}H_{27}N_3O_2$, 354.2; found, 354.3. $R_f$=2.96 min (10-70 ACN: H$_2$O, reverse phase HPLC).

Preparation 5

Biphenyl-2-ylcarbamic Acid 1-{2-[(4-Formylbenzoyl)methylamino]ethyl}piperidin-4-yl Ester

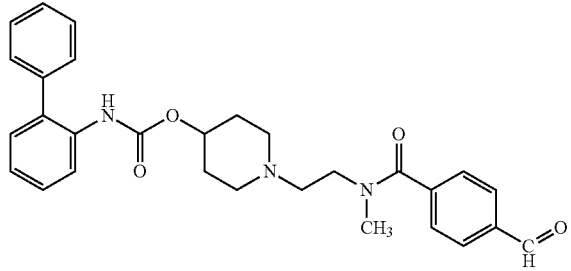 [SMILES: CN(CCN1CCC(OC(=O)Nc2ccccc2-c2ccccc2)CC1)C(=O)c1ccc(C=O)cc1]

To a three-necked 1-L flask was added 4-carboxybenzaldehyde (4.77 g, 31.8 mmol), EDC (6.64 g, 34.7 mmol), HOBT (1.91 g, 31.8 mmol), and DCM (200 mL). When the mixture was homogenous, a solution of biphenyl-2-ylcarbamic acid 142-methylaminoethyl)piperidin-4-yl ester (10 g, 31.8 mmol; prepared as described in Preparation 4) in DCM (100 mL) was added slowly. The reaction mixture was stirred at room temperature for 16 hours and then washed with water (1×100 mL), 1N HCl (5×60 mL), 1N NaOH (1×100 mL), brine (1×50 mL), dried over sodium sulfate, filtered and concentrated to afford 12.6 g of the title intermediate (92% yield; 85% purity based on HPLC). MS m/z: [M+H$^+$] calcd for $C_{29}H_{31}N_3O_4$, 486.2; found, 486.4. $R_f$ 3.12 min (10-70 ACN: H$_2$O, reverse phase HPLC).

Example 1

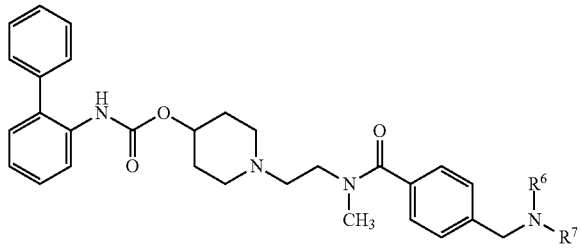

To a stirred solution of biphenyl-2-ylcarbamic acid 1-{2-[(4-formylbenzoyl)methylamino]ethyl}piperidin-4-yl ester (50 mg, 0.1 mmol; prepared as described in Preparation 5) in MeOH (1 mL) was added 1-acetylpiperazine (26 mg, 0.2 mmol). The mixture was shake for an hour and NaBH(OAc)$_3$ (67 mg, 0.3 mmol) was added. This was allowed to stir for 14 hours. The solvent was then removed under reduced pressure. To the mixture was added 1:1 HOAc:H$_2$O (1.0 mL) and then purified by reverse phase HPLC (gradient elution, ACN/H$_2$O) to provide 37.8 mg of Compound 1-1 with 99% purity.

Compounds 1-2 to 1-44 were made in a similar manner by substituting the appropriate amine in the reductive amination step.

| # | Name | —NR$^6$R$^7$ |
|---|------|--------------|
| 1-1 | biphenyl-2-yl-carbamic acid 1-(2-{[4-(4-acetylpiperazin-1-ylmethyl)benzoyl]methylamino}ethyl)piperidin-4-yl ester. MS m/z: [M + H$^+$] calcd for C$_{35}$H$_{43}$N$_5$O$_4$, 598.33; found, 598.4. | |
| 1-2 | biphenyl-2-ylcarbamic acid 1-{2-[(4-aminomethyl-benzoyl)methylamino]ethyl}piperidin-4-yl ester. MS m/z: [M + H$^+$] calcd for C$_{29}$H$_{34}$N$_4$O$_3$, 487.26; found, 487.3, 509.3. | —NH$_2$ |
| 1-3 | biphenyl-2-ylcarbamic acid 1-{2-[(4-{[(furan-2-carbonyl)amino]methyl}benzoyl)methylamino]ethyl}piperidin-4-yl ester. MS m/z: [M + H$^+$] calcd for C$_{34}$H$_{36}$N$_4$O$_5$, 581.27; found, 581.2. | |
| 1-4 | biphenyl-2-ylcarbamic acid 1-(2-{[4-(acetylamino-methyl)benzoyl]methylamino}ethyl)piperidin-4-yl ester. MS m/z: [M + H$^+$] calcd for C$_{31}$H$_{36}$N$_4$O$_4$, 529.27; found, 529.2. | |
| 1-5 | biphenyl-2-ylcarbamic acid 1-{2-[methyl-(4-{[(pyridine-4-carbonyl)amino]methyl}benzoyl)amino]ethyl}piperidin-4-yl ester. MS m/z: [M + H$^+$] calcd for C$_{35}$H$_{37}$N$_5$O$_4$, 592.28; found, 592.2. | |
| 1-6 | biphenyl-2-ylcarbamic acid 1-[2-({4-[(cyclopropane-carbonylamino)methyl]benzoyl}methylamino)ethyl] piperidin-4-yl ester. MS m/z: [M + H$^+$] calcd for C$_{33}$H$_{38}$N$_4$O$_4$, 555.29; found, 555.3. | |
| 1-7 | biphenyl-2-ylcarbamic acid 1-{2-[methyl-(4-{[(thiophene-2-carbonyl)amino]methyl}benzoyl)amino]ethyl}piperidin-4-yl ester. MS m/z: [M + H$^+$] calcd for C$_{34}$H$_{36}$N$_4$O$_4$S, 597.25; found, 597.2. | |
| 1-8 | biphenyl-2-ylcarbamic acid 1-[2-({4-[(cyclobutane-carbonylamino)methyl]benzoyl}methylamino)ethyl] piperidin-4-yl ester. MS m/z: [M + H$^+$] calcd for C$_{34}$H$_{40}$N$_4$O$_4$, 569.31; found, 569.3. | |
| 1-9 | biphenyl-2-ylcarbamic acid 1-(2-{[4-(isopropylamino-methyl)benzoyl]methylamino}ethyl)piperidin-4-yl ester. MS m/z: [M + H$^+$] calcd for C$_{32}$H$_{40}$N$_4$O$_3$, 529.31; found, 529.3. | |

-continued

| # | Name | —NR⁶R⁷ |
|---|------|--------|

| # | Name | $-NR^6R^7$ |
|---|------|-----------|
| 1-10 | biphenyl-2-ylcarbamic acid 1-[2-({4-[(cyclopropyl-methylamino)methyl]benzoyl}methylamino)ethyl]piperidin-4-yl ester. MS m/z: [M + H⁺] calcd for $C_{33}H_{40}N_4O_3$, 541.31; found, 541.3. | methyl-NH-CH₂-cyclopropyl |
| 1-11 | biphenyl-2-ylcarbamic acid 1-{2-[methyl-(4-morpholin-4-ylmethylbenzoyl)amino]ethyl}piperidin-4-yl ester. MS m/z: [M + H⁺] calcd for $C_{33}H_{40}N_4O_4$, 557.31; found, 557.2. | morpholinyl |
| 1-12 | biphenyl-2-ylcarbamic acid 1-{2-[(4-{[(2-methanesulfonylethyl)methylamino]methyl}benzoyl)methylamino]ethyl}piperidin-4-yl ester. MS m/z: [M + H⁺] calcd for $C_{33}H_{42}N_4O_5S$, 607.29; found, 607.2. | —N(CH₃)CH₂CH₂S(O)₂CH₃ |
| 1-13 | biphenyl-2-ylcarbamic acid 1-(2-{[4-(4-ethylpiperazin-1-ylmethyl)benzoyl]methylamino}ethyl)piperidin-4-yl ester. MS m/z: [M + H⁺] calcd for $C_{35}H_{45}N_5O_3$, 584.35; found, 584.3. | 4-ethylpiperazin-1-yl (shown with N-methyl) |
| 1-14 | biphenyl-2-ylcarbamic acid 1-(2-{[4-(4-isopropylpiperazin-1-ylmethyl)benzoyl]methylamino}ethyl)piperidin-4-yl ester. MS m/z: [M + H⁺] calcd for $C_{36}H_{47}N_5O_3$, 598.37; found, 598.3. | 4-isopropylpiperazin-1-yl |
| 1-15 | biphenyl-2-ylcarbamic acid 1-[2-({4-[(ethylisopropyl-amino)methyl]benzoyl}methylamino)ethyl]piperidin-4-yl ester. MS m/z: [M + H⁺] calcd for $C_{34}H_{44}N_4O_3$, 557.34; found, 557.3. | —N(CH₂CH₃)(CH(CH₃)₂) |
| 1-16 | biphenyl-2-ylcarbamic acid 1-(2-{[4-(2,6-dimethyl-morpholin-4-ylmethyl)benzoyl]methylamino}ethyl)piperidin-4-yl ester. MS m/z: [M + H⁺] calcd for $C_{35}H_{44}N_4O_4$, 585.34; found, 585.3. | 2,6-dimethylmorpholin-4-yl |
| 1-17 | biphenyl-2-ylcarbamic acid 1-{2-[(4-{[bis-(2-hydroxyethyl)amino]methyl}benzoyl)methylamino]ethyl}piperidin-4-yl ester. MS m/z: [M + H⁺] calcd for $C_{33}H_{42}N_4O_5$, 575.32; found, 575.3. | —N[(CH₂)₂OH]₂ |
| 1-18 | biphenyl-2-ylcarbamic acid 1-(2-{[4-(tert-butylamino-methyl)benzoyl]methylamino}ethyl)piperidin-4-yl ester. MS m/z: [M + H⁺] calcd for $C_{33}H_{42}N_4O_3$, 543.33; found, 543.3. | —NH—C(CH₃)₃ |
| 1-19 | biphenyl-2-ylcarbamic acid 1-[2-({4-[(ethylmethyl-amino)methyl]benzoyl}methylamino)ethyl]piperidin-4-yl ester. MS m/z: [M + H⁺] calcd for $C_{32}H_{40}N_4O_3$, 529.31; found, 529.2. | —N(CH₃)(CH₂CH₃) |
| 1-20 | biphenyl-2-ylcarbamic acid 1-{2-[(4-{[bis-(2-ethoxyethyl)amino]methyl}benzoyl)methylamino]ethyl}piperidin-4-yl ester. MS m/z: [M + H⁺] calcd for $C_{37}H_{50}N_4O_5$, 631.38; found, 631.3. | —N[(CH₂)₂OCH₂CH₃]₂ |
| 1-21 | biphenyl-2-ylcarbamic acid 1-[2-(methyl-{4-[(methyl-pyridin-3-ylmethylamino)methyl]benzoyl}amino)ethyl]piperidin-4-yl ester. MS m/z: [M + H⁺] calcd for $C_{36}H_{41}N_5O_3$, 592.32; found, 592.3. | —N(CH₃)CH₂(pyridin-3-yl) |

| # | Name | —NR⁶R⁷ |
|---|------|--------|
| 1-22 | biphenyl-2-ylcarbamic acid 1-{2-[(4-{[bis(2-methoxy-ethyl)amino]methyl}benzoyl)methylamino]ethyl}piperidin-4-yl ester. MS m/z: [M + H⁺] calcd for $C_{35}H_{46}N_4O_5$, 603.35; found, 603.3. | 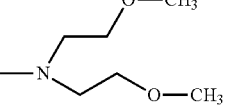 |
| 1-23 | biphenyl-2-ylcarbamic acid 1-{2-[(4-{[(2-hydroxyethyl)methylamino]methyl}benzoyl)methylamino]ethyl}piperidin-4-yl ester. MS m/z: [M + H⁺] calcd for $C_{32}H_{40}N_4O_4$, 545.31; found, 545.2. | 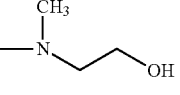 |
| 1-24 | biphenyl-2-ylcarbamic acid 1-[2-(methyl-{4-[(methyl-pyridin-4-ylmethylamino)methyl]benzoyl}amino)ethyl]piperidin-4-yl ester. MS m/z: [M + H⁺] calcd for $C_{36}H_{41}N_5O_3$, 592.32; found, 592.3. | 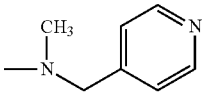 |
| 1-25 | biphenyl-2-ylcarbamic acid 1-[2-({4-[4-(2-methoxyethyl)piperazin-1-ylmethyl]benzoyl}methylamino)ethyl]piperidin-4-yl ester. MS m/z: [M + H⁺] calcd for $C_{36}H_{47}N_5O_4$, 614.36; found, 614.3. | 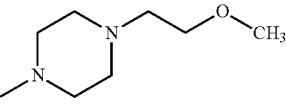 |
| 1-26 | biphenyl-2-ylcarbamic acid 1-(2-{[4-(4-ethanesulfonyl-piperazin-1-ylmethy)benzoyl]methylamino}ethyl)piperidin-4-yl ester. MS m/z: [M + H⁺] calcd for $C_{35}H_{45}N_5O_5S$, 648.31; found, 648.3. | 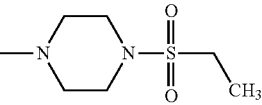 |
| 1-27 | biphenyl-2-ylcarbamic acid 1-(2-{[4-(2,5-diaza-bicyclo[2.2.1]hept-2-ylmethyl)benzoyl]methylamino}ethyl)piperidin-4-yl ester. MS m/z: [M + H⁺] calcd for $C_{34}H_{41}N_5O_3$, 568.33; found, 568.4. | 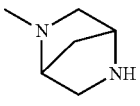 |
| 1-28 | biphenyl-2-ylcarbamic acid 1-[2-({4-[(2-hydroxyethyl-amino)methyl]benzoyl}methylamino)ethyl]piperidin-4-yl ester. MS m/z: [M + H⁺] calcd for $C_{31}H_{38}N_4O_4$, 531.29; found, 531.2. | —NH[(CH₂)₂OH] |
| 1-29 | biphenyl-2-ylcarbamic acid 1-(2-{methyl-[4-(4-pyridin-4-ylpiperazin-1-ylmethyl)benzoyl]amino}ethyl-piperidin-4-yl ester. MS m/z: [M + H⁺] calcd for $C_{38}H_{44}N_6O_3$, 633.35; found, 633.4. |  |
| 1-30 | biphenyl-2-ylcarbamic acid 1-(2-{[4-(4-dimethyl-carbamoylmethylpiperazin-1-ylmethyl)benzoyl]methylamino}ethyl)piperidin-4-yl ester. MS m/z: [M + H⁺] calcd for $C_{37}H_{48}N_6O_4$, 641.37; found, 641.4. | 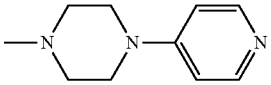 |
| 1-31 | biphenyl-2-ylcarbamic acid 1-(2-{methyl-[4-(4-pyridin-4-ylmethylpiperazin-1-ylmethyl)benzoyl]amino}ethyl)piperidin-4-yl ester. MS m/z: [M + H⁺] calcd for $C_{39}H_{46}N_6O_3$, 647.36; found, 647.4. | 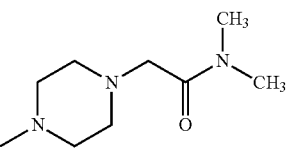 |
| 1-32 | biphenyl-2-ylcarbamic acid 1-[2-(methyl-{4-[4-(2-oxo-2-pyrrolidin-1-ylethyl)piperazin-1-ylmethyl]benzoyl}amino)ethyl]piperidin-4-yl ester. MS m/z: [M + H⁺] calcd for $C_{39}H_{50}N_6O_4$, 667.39; found, 667.4. | 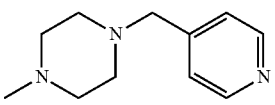 |
| 1-33 | biphenyl-2-ylcarbamic acid 1-[2-({4-[(2-hydroxyethyl-amino)methyl]benzoyl}methylamino)ethyl]piperidin-4-yl ester. MS m/z: [M + H⁺] calcd for $C_{30}H_{36}N_4O_3$, 501.29; found, 501.2. | —NH(CH₃) |
| 1-34 | biphenyl-2-ylcarbamic acid 1-{2-[(4-ethylaminomethyl-benzoyl)methylamino]ethyl}piperidin-4-yl ester. MS m/z: [M + H⁺] calcd for $C_{31}H_{38}N_4O_3$, 515.29; found, 515.2. | —NH(CH₂CH₃) |

| # | Name | —NR⁶R⁷ |
|---|---|---|
| 1-35 | biphenyl-2-ylcarbamic acid 1-{2-[(4-cyclopropylamino-methylbenzoyl)methylamino]ethyl}piperidin-4-yl ester. MS m/z: [M + H⁺] calcd for $C_{32}H_{38}N_4O_3$, 527.29; found, 527.2. | |
| 1-36 | biphenyl-2-ylcarbamic acid 1-[2-({4-[(2-methoxyethyl-amino)methyl]benzoyl}methylamino)ethyl]piperidin-4-yl ester. MS m/z: [M + H⁺] calcd for $C_{32}H_{40}N_4O_4$, 545.31; found, 545.2. | |
| 1-37 | biphenyl-2-ylcarbamic acid 1-(2-{methyl-[4-(3-oxopiperazin-1-ylmethyl)benzoyl]amino}ethyl)piperidin-4-yl ester. MS m/z: [M + H⁺] calcd for $C_{33}H_{39}N_5O_4$, 570.30; found, 570.2. | |
| 1-38 | biphenyl-2-ylcarbamic acid 1-(2-{[4-(4-acetyl-[1,4]diazepan-1-ylmethyl)benzoyl]methylamino}ethyl)piperidin-4-yl ester. MS m/z: [M + H⁺] calcd for $C_{36}H_{45}N_5O_4$, 612.35; found, 612.4. | |
| 1-39 | biphenyl-2-ylcarbamic acid 1-[2-({4-[4-(4-hydroxyphenyl)piperazin-1-ylmethyl]benzoyl}methylamino)ethyl]piperidin-4-yl ester. MS m/z: [M + H⁺] calcd for $C_{39}H_{45}N_5O_4$, 648.35; found, 648.4. | |
| 1-40 | biphenyl-2-ylcarbamic acid 1-[2-({4-[(carbamoylmethyl-amino)methyl]benzoyl}methylamino)ethyl]piperidin-4-yl ester. MS m/z: [M + H⁺] calcd for $C_{31}H_{37}N_5O_4$, 544.28; found, 544.2. | |
| 1-41 | biphenyl-2-ylcarbamic acid 1-(2-{[4-(4-dimethyl-carbamoylpiperazin-1-ylmethyl)benzoyl]methylamino}ethyl)piperidin-4-yl ester. MS m/z: [M + H⁺] calcd for $C_{36}H_{46}N_6O_4$, 627.36; found, 627.4. | |
| 1-42 | biphenyl-2-ylcarbamic acid 1-[2-(methyl-{4-[4-(pyrrolidine-1-carbonyl)piperazin-1-ylmethyl]benzoyl}amino)ethyl]piperidin-4-yl ester. MS m/z: [M + H⁺] calcd for $C_{38}H_{48}N_6O_4$, 653.37; found, 653.4. | |
| 1-43 | biphenyl-2-ylcarbamic acid 1-[2-(methyl-{4-[4-(piperidine-1-carbonyl)piperazin-1-ylmethyl]benzoyl}amino)ethyl]piperidin-4-yl ester. MS m/z: [M + H⁺] calcd for $C_{39}H_{50}N_6O_4$, 667.39; found, 667.4. | |
| 1-44 | biphenyl-2-ylcarbamic acid 1-[2-(methyl-{4-[4-(morpholine-4-carbonyl)piperazin-1-ylmethyl]benzoyl}amino)ethyl]piperidin-4-yl ester. MS m/z: [M + H⁺] calcd for $C_{38}H_{48}N_6O_5$, 669.37; found, 669.4. | |

Preparation 6

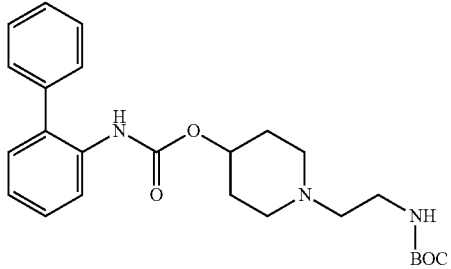 [SMILES: CC(C)(C)OC(=O)NCCN1CCC(OC(=O)Nc2ccccc2-c2ccccc2)CC1]

To a stirred solution of biphenyl-2-ylcarbamic acid piperidin-4-yl ester (2.00 g, 6.76 mmol; prepared as described in Preparation 1) and DIPEA (3.54 mL, 20.3 mmol) in MeCN (67.6 mL) at 50° C., was added 2-BOC-amino ethyl bromide (1.82 g, 8.11 mmol) and the reaction mixture was heated at 50° C. overnight. The solvent was removed under reduced pressure and dissolved in DCM (60 mL) and washed with saturated aqueous sodium bicarbonate solution (30 mL), organics dried (MgSO$_4$) and solvent removed under reduced pressure. The crude residue was purified by column chromatography (5% MeOH/DCM) to give the title intermediate as a white solid (2.32 g, 78%).

Preparation 7

Biphenyl-2-ylcarbamic acid 1-(2-aminoethyl)piperidin-4-yl ester

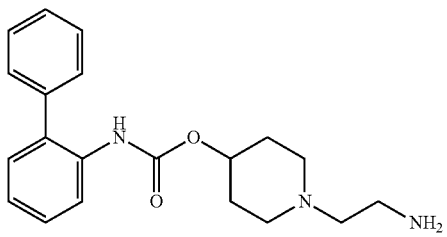 [SMILES: NCCN1CCC(OC(=O)Nc2ccccc2-c2ccccc2)CC1]

The product of Preparation 6 was dissolved in TFA/DCM (25%, 52 mL) and stirred at room temperature for 2 hours. The solvent was removed under reduced pressure and the crude residue dissolved in DCM (30 mL) and washed with 1N NaOH (15 mL). The organics were separated, dried (MgSO$_4$) and solvent removed under reduced pressure to give the title intermediate (1.61 g, 90%).

PREPARATION 8

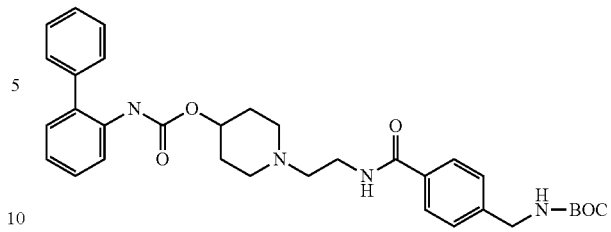

To a stirred solution of the product of Preparation 7 (339 mg, 1 mmol), BOC-(4-aminomethyl)benzoic acid (301 mg, 1.2 mmol) and HATU (456 mg, 1.2 mmol) in DMF (2 mL), was added DIPEA (226 µL, 1.3 mmol). The reaction mixture was stirred at room temperature overnight before removing the solvent under reduced pressure. The resulting residue was dissolved in DCM (20 mL) and washed with saturated aqueous sodium bicarbonate solution (10 mL), organics dried (MgSO$_4$) and solvent removed under reduced pressure to yield the crude title intermediate, which was used directly in the next step.

PREPARATION 9

Biphenyl-2-ylcarbamic Acid 1-[2-(4-Formylbenzoylamino)ethyl]piperidin-4-yl Ester

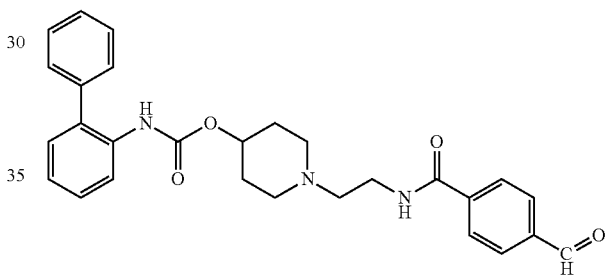

A mixture of 4-carboxybenzaldehyde (0.95 g, 6.35 mmol) and HATU (3.02 g, 7.94 mmol) in 55 mL of DCM was stirred at room temperature for 1 hour and then biphenyl-2-ylcarbamic acid 1-(2-aminoethyl)piperidin-4-yl ester (3 g, 5.29 mmol; prepared as described in Preparation 7) and DIPEA (4.6 mL, 26.45 mmol) were added. The resulting mixture was stirred at room temperature for 2 hours and then diluted with 100 mL of DCM and washed with saturated sodium bicarbonate (150 mL) and brine (150 mL). The organic layer was dried over MgSO$_4$, filtered and concentrated to provide 2.3 g of the title intermediate (92% yield), which was suitable for use without further purification.

Example 2

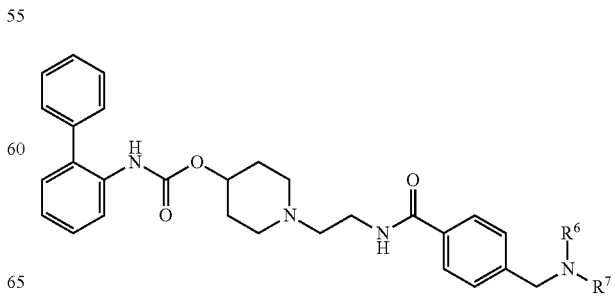

The crude product of Preparation 8 was dissolved in TFA/DCM (25%, 10 mL) and stirred at room temperature for 2 hours. The solvent was removed under reduced pressure and crude residue dissolved in DCM (15 mL) and washed with 1N NaOH (5 mL). The organics were separated, dried (MgSO$_4$) and solvent removed under reduced pressure to give Compound 2-1 ($R^6$ and $R^7$=H) (472 mg, ~100% over 2 steps): biphenyl-2-ylcarbamic acid 1-[2-(4-aminomethylbenzoyl amino)ethyl]piperidin-4-yl ester. MS m/z: [M+H$^+$] calcd for $C_{28}H_{32}N_4O_3$, 473.25; found, 473.2.

Using the procedure of Example 1, but substituting the product of Preparation 9 in place of the product of Preparation 5, and substituting the appropriate amine in the reductive amination step, compounds having other $R^6$ and $R^7$ groups can also be made.

Preparation 10

3-[4-(Biphenyl-2-ylcarbamoyloxy)piperidin-1-yl] propionic Acid Methyl Ester

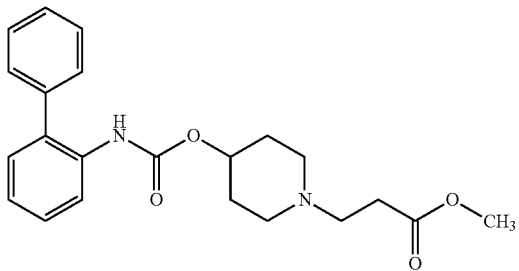 [SMILES: COC(=O)CCN1CCC(OC(=O)Nc2ccccc2-c2ccccc2)CC1]

Methyl 3-bromopropionate (553 µL, 5.07 mmol) was added to a stirred solution of biphenyl-2-ylcarbamic acid piperidin-4-yl ester (1.00 g, 3.38 mmol; prepared as described in Preparation 1) and DIPEA (1.76 mL, 10.1 mmol) in ACN (34 mL) at 50° C. and the reaction mixture was heated at 50° C. overnight. The solvent was then removed under reduced pressure, and the residue was dissolved in DCM (30 mL). The resulting solution was washed with saturated aqueous sodium bicarbonate solution (10 mL), dried over MgSO$_4$, filtered and the solvent was removed under reduced pressure. The crude residue was purified by column chromatography (5-10% MeOH/DCM) to give 905 mg of the title intermediate (70% yield).

Preparation 11

3-[4-(Biphenyl-2-ylcarbamoyloxy)piperidin-1-yl] propionic Acid

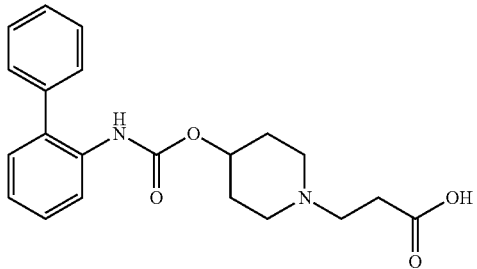 [SMILES: O=C(O)CCN1CCC(OC(=O)Nc2ccccc2-c2ccccc2)CC1]

A stirred solution of 3-[4-(biphenyl-2-ylcarbamoyloxy)piperidin-1-yl]propionic acid methyl ester (902 mg, 2.37 mmol; prepared as described in Preparation 10) and lithium hydroxide (171 mg, 7.11 mmol) in 50% THF:H$_2$O (24 mL) was heated at 30° C. overnight, and then acidified with concentrated HCl and lyophilized to give the title intermediate (~100% yield, also contains LiCl salts).

Preparation 12

Biphenyl-2-ylcarbamic acid 1-[2-(3-hydroxymethyl-benzylcarbamoyl)ethyl]piperidin-4-yl Ester

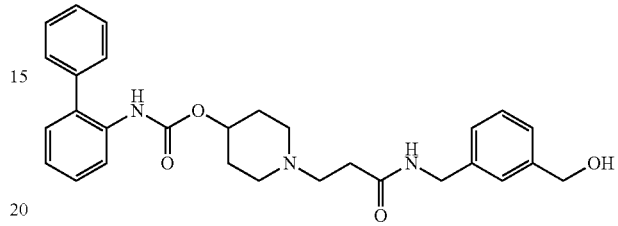

To a stirred solution of 3-[4-(Biphenyl-2-ylcarbamoyloxy) piperidin-1-yl]propionic acid (0.5 g, 1.36 mmol; prepared as described in Preparation 11) in DCM (200 mL) was added DIPEA (10.7 mL, 6.12 mmol), 3-aminomethylbenzyl alcohol (0.33 g, 1.9 mmol), DMAP (0.14 g, 0.14 mmol) and EDCI (0.364 g, 1.9 mmol). The reaction mixture was stirred at room temperature for 2 hours. The mixture was concentrated, taken up in EtOAc (20 mL) and then washed with K$_2$CO$_3$ (3×10 mL), H$_2$O (1×10 mL), brine (1×10 mL), dried over magnesium sulfate, filtered and concentrated. The mixture was purified on silica gel (7% MeOH/CHCl$_3$) to afford 0.38 g of the title intermediate (57% yield).

Preparation 13

Biphenyl-2-ylcarbamic Acid 1-[2-(3-formylbenzylcarbamoyl)ethyl]piperidin-4-yl Ester

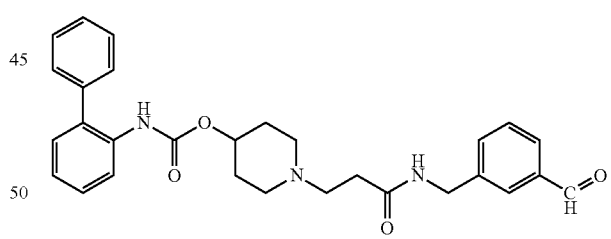

To a flask was added biphenyl-2-ylcarbamic acid 1-[2-(3-hydroxymethylbenzyl carbamoyl)ethyl]piperidin-4-yl ester (0.33 g, 0.68 mmol; prepared as described in Preparation 12), DCM (5 mL), DIPEA (0.47 mL, 2.7 mol) and DMSO (0.2 mL, 2.7 mol). Using an ice bath, the mixture was cooled to about –10° C. and sulfur trioxide pyridine-complex (0.32 g, 2.0 mol) was added. The reaction was stirred at –10° C. for 0.75 hour. Before removing the ice-bath, the reaction was quenched by adding water (5 mL). The aqueous layer was separated and the organic layer was washed with water (2×5 mL), 1.0N NaHSO$_4$(aq) (2×5 mL), 1.0N NaHCO$_3$(aq) (1×5 mL) and brine (0.5 L) and then dried over MgSO$_4$ and filtered to provide the title compound which was used without further purification.

Example 3

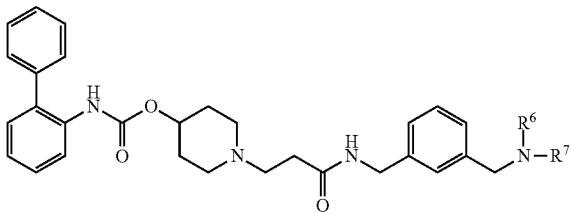

To a stirred solution of biphenyl-2-ylcarbamic acid 1-[2-(3-formylbenzyl carbamoyl)ethyl]piperidin-4-yl ester (39 mg, 0.08 mmol; prepared as described in Preparation 13) in DCM (1 mL) was added 2-benzyl-2,5-diaza-bicyclo[2.2.1]heptane (18.8 mg, 0.1 mmol), and NaBH(OAc)$_3$ (275 mg, 1.24 mmol). The mixture was stirred for 2 days and then the solvent was removed under reduced pressure. A 1:1 solution of HOAc and water (8.0 mL) was added to the reaction mixture. The mixture was chromatographed on reverse-phase HPLC (gradient elution, 10-50% ACN/H$_2$O) to afford 4.0 mg of the title compound (5.6% yield) as a bis(trifluoroacetate) salt.

Compounds 3-2 to 3-10 were made in a similar manner by substituting the appropriate amine in the reductive amination step.

| # | Name | —NR$^6$R$^7$ |
|---|---|---|
| 3-1 | biphenyl-2-ylcarbamic acid 1-{2-[3-((1R,4R)-5-benzyl-2,5-diaza-bicyclo[2.2.1]hept-2-ylmethyl)benzyl-carbamoyl]ethyl}piperidin-4-yl ester. MS m/z: [M + H$^+$] calcd for C$_{41}$H$_{47}$N$_5$O$_3$, 658.37; found, 657.3. | |
| 3-2 | biphenyl-2-ylcarbamic acid 1-[2-(3-aminomethylbenzyl-carbamoyl)ethyl]piperidin-4-yl ester. MS m/z: [M + H$^+$] calcd for C$_{29}$H$_{34}$N$_4$O$_3$, 487.26; found, 487.4. | —NH$_2$ |
| 3-3 | biphenyl-2-ylcarbamic acid 1-[2-(3-{[(pyridin-4-yl-methyl)amino]methyl}benzylcarbamoyl)ethyl]piperidin-4-yl ester. MS m/z: [M + H$^+$] calcd for C$_{35}$H$_{39}$N$_5$O$_3$, 578.31; found, 578.2. | |
| 3-4 | biphenyl-2-ylcarbamic acid 1-(2-{3-[(furan-2-ylmethyl-methylamino)methyl]benzylcarbamoyl}ethyl)piperidin-4-yl ester. MS m/z: [M + H$^+$] calcd for C$_{35}$H$_{40}$N$_4$O$_4$, 581.31; found, 581.2. | |
| 3-5 | {[3-({3-[4-(biphenyl-2-ylcarbamoyloxy)piperidin-1-yl]propionylamino}methyl)benzyl]methylamino}acetic acid. MS m/z: [M + H$^+$] calcd for C$_{32}$H$_{38}$N$_4$O$_5$, 559.28; found, 559.2. | |
| 3-6 | biphenyl-2-ylcarbamic acid 1-[2-(3-cyclobutylamino-methylbenzylcarbamoyl)ethyl]piperidin-4-yl ester. MS m/z: [M + H$^+$] calcd for C$_{33}$H$_{40}$N$_4$O$_3$, 541.31; found, 541.2. | |
| 3-7 | biphenyl-2-ylcarbamic acid 1-[2-(3-cyclopropylamino-methylbenzylcarbamoyl)ethyl]piperidin-4-yl ester. MS m/z: [M + H$^+$] calcd for C$_{32}$H$_{38}$N$_4$O$_3$, 527.29; found, 527.2. | |
| 3-8 | biphenyl-2-ylcarbamic acid 1-[2-(3-morpholin-4-yl-methylbenzylcarbamoyl)ethyl]piperidin-4-yl ester. MS m/z: [M + H$^+$] calcd for C$_{33}$H$_{40}$N$_4$O$_4$, 557.31; found, 557.2. | |
| 3-9 | biphenyl-2-ylcarbamic acid 1-[2-(3-methylaminomethyl-benzylcarbamoyl)ethyl]piperidin-4-yl ester. MS m/z: [M + H$^+$] calcd for C$_{30}$H$_{36}$N$_4$O$_3$, 501.28; found, 501.2. | —NH(CH$_3$) |
| 3-10 | biphenyl-2-ylcarbamic acid 1-[2-(3-dimethylamino-methylbenzylcarbamoyl)ethyl]piperidin-4-yl ester. MS m/z: [M + H$^+$] calcd for C$_{31}$H$_{38}$N$_4$O$_3$, 515.29; found, 515.2. | —N(CH$_3$)$_2$ |

Example 4

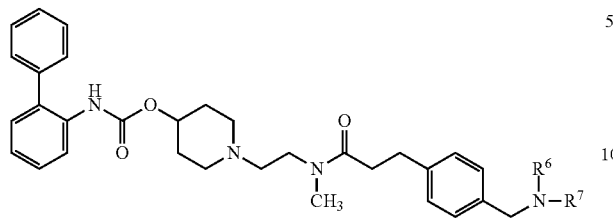

Using the procedure of Example 1, but substituting 3-(4-formylphenyl)propionic acid in place of 4-carboxybenzaldehyde in Preparation 5, and substituting the appropriate amine in the reductive amination step, the following compounds were prepared. The preparation of 3-(4-formylphenyl)propionic acid was done according to *Tetrahedron* 52(20):6913-6930 (2001).

| # | Name | —NR$^6$R$^7$ |
|---|---|---|
| 4-1 | biphenyl-2-ylcarbamic acid 1-(2-{methyl-[3-(4-methyl aminomethylphenyl)propionyl]amino}ethyl)piperidin-4-yl ester. MS m/z: [M + H$^+$] calcd for C$_{32}$H$_{40}$N$_4$O$_3$, 529.31; found, 529.2. | —NH(CH$_3$) |
| 4-2 | biphenyl-2-ylcarbamic acid 1-(2-{[3-(4-ethylamino methylphenyl)propionyl]methylamino}ethyl)piperidin-4-yl ester. MS m/z: [M + H$^+$] calcd for C$_{33}$H$_{42}$N$_4$O$_3$, 543.33; found, 543.2. | —NH(CH$_2$CH$_3$) |

Preparation 14

Biphenyl-2-ylcarbamic Acid 1-[2-(4-Aminomethylphenylcarbamoyl)ethyl]piperidin-4-yl Ester

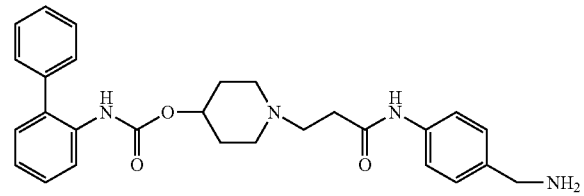 [SMILES: NCc1ccc(NC(=O)CCN2CCC(OC(=O)Nc3ccccc3-c3ccccc3)CC2)cc1]

To a stirred solution of 4-(N-tert-butoxycarbonylaminomethyl)aniline (756 mg, 3.4 mmol), 3-[4-(biphenyl-2-ylcarbamoyloxy)piperidin-1-yl]propionic acid (1.5 g, 4.08 mmol; prepared as described in Preparation 11) and HATU (1.55 g, 4.08 mmol) in DMF (6.8 mL), was added DIPEA (770 μL, 4.42 mmol). The reaction mixture was stirred at 50° C. overnight, and then the solvent was removed under reduced pressure. The resulting residue was dissolved in DCM (20 mL) and washed with saturated aqueous sodium bicarbonate solution (10 mL). The organic phase was then dried over MgSO$_4$ and the solvent was removed under reduced pressure. The crude product was purified by flash chromatography (5-10% MeOH/DCM) to give a solid, which was dissolved in TFA/DCM (25%, 30 mL) and stirred at room temperature for 2 hours. The solvent was then removed under reduced pressure and the crude residue was dissolved in DCM (30 mL) and washed with 1N NaOH (15 mL). The organic phase was separated, dried over MgSO$_4$, filtered and the solvent was removed under reduced pressure to give 1.5 g of the title intermediate (94% yield over 2 steps).

Preparation 15

Biphenyl-2-ylcarbamic Acid 1-[2-(4-Formylphenylcarbamoyl)ethyl]piperidin-4-yl Ester

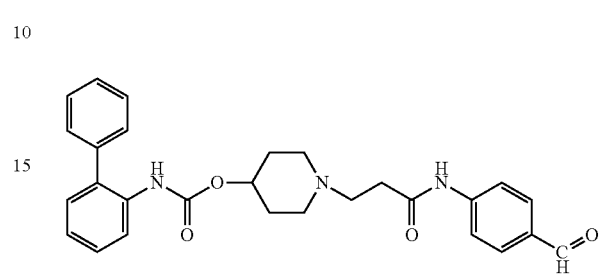

A mixture of biphenyl-2-ylcarbamic acid 1-[2-(4-aminomethylphenylcarbamoyl)ethyl]piperidin-4-yl ester (1 g, 2.7 mmol; prepared as described in Preparation 14), 4-aminobenzyl alcohol (498 mg, 4.05 mmol), HATU (1.54 g, 4.05 mmol) and DIPEA (1.41 mL, 8.1 mmol) in DCM (14 mL) was stirred at room temperature for 2 hours. The reaction mixture was diluted with 100 mL of DCM and washed first with a 1:3 mixture of 1N HCl/water (100 mL), then brine (100 mL). The organic layer was dried over MgSO$_4$, filtered and concentrated. The residue was dissolved in DCM (100 mL) and the solution was cooled to −5° C. DIPEA (1.1 mL, 6.33 mmol) and DMSO (1.5 mL, 21.1 mmol) were added to the solution, followed by sulfur trioxide pyridine complex (1 g, 6.33 mmol). The reaction mixture was stirred at 0° C. for 1 hour then washed with a saturated solution of sodium bicarbonate (100 mL) and brine (100 mL). The organic layer was dried over MgSO$_4$, filtered and concentrated to give 0.84 g of the title intermediate (66% yield) as an oil.

Example 5

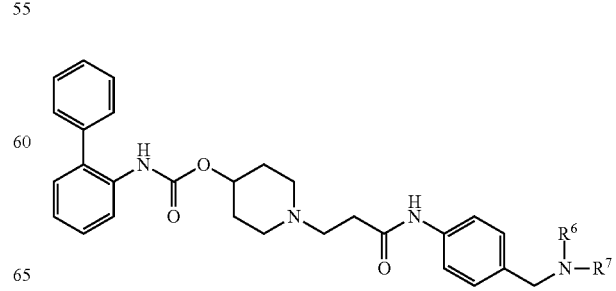

Using the procedure of Example 1, but substituting biphenyl-2-ylcarbamic acid 1-[2-(4-formylphenylcarbamoyl)ethyl]piperidin-4-yl ester (prepared as described in Preparation 15) in place of the product of Preparation 5, and substituting the appropriate amine in the reductive amination step, the following compounds were prepared.

| # | Name | —NR$^6$R$^7$ |
|---|------|--------------|
| 5-1 | biphenyl-2-ylcarbamic acid 1-[2-(4-aminomethylphenylcarbamoyl)ethyl]piperidin-4-yl ester. MS m/z: [M + H$^+$] calcd for C$_{28}$H$_{32}$N$_4$O$_3$, 473.25; found, 473.2. | —NH$_2$ |
| 5-2 | biphenyl-2-ylcarbamic acid 1-(2-{4-[(4-trifluoromethylbenzenesulfonylamino)methyl]phenylcarbamoyl}ethyl)piperidin-4-yl ester. MS m/z: [M + H$^+$] calcd for C$_{35}$H$_{35}$F$_3$N$_4$O$_5$S, 681.23; found, 681.1. | |
| 5-3 | biphenyl-2-ylcarbamic acid 1-(2-{4-[(butane-1-sulfonylamino)methyl]phenylcarbamoyl}ethyl)piperidin-4-yl ester. MS m/z: [M + H$^+$] calcd for C$_{32}$H$_{40}$N$_4$O$_5$S, 593.27; found, 593.2. | |
| 5-4 | biphenyl-2-ylcarbamic acid 1-(2-{4-[(2-fluorobenzenesulfonylamino)methyl]phenylcarbamoyl}ethyl)piperidin-4-yl ester. MS m/z: [M + H$^+$] calcd for C$_{34}$H$_{35}$FN$_4$O$_5$S, 631.23; found, 631.2. | |
| 5-5 | biphenyl-2-ylcarbamic acid 1-(2-{4-[(quinoline-8-sulfonylamino)methyl]phenylcarbamoyl}ethyl)piperidin-4-yl ester. MS m/z: [M + H$^+$] calcd for C$_{37}$H$_{37}$N$_5$O$_5$S, 664.25; found, 664.2. | |
| 5-6 | biphenyl-2-ylcarbamic acid 1-{2-[4-(ethanesulfonylaminomethyl)phenylcarbamoyl]ethyl}piperidin-4-yl ester. MS m/z: [M + H$^+$] calcd for C$_{30}$H$_{36}$N$_4$O$_5$S, 565.24; found, 565.2. | |
| 5-7 | biphenyl-2-ylcarbamic acid 1-(2-{4-[(2,6-dichlorobenzenesulfonylamino)methyl]phenylcarbamoyl}ethyl)piperidin-4-yl ester. MS m/z: [M + H$^+$] calcd for C$_{34}$H$_{34}$Cl$_2$N$_4$O$_5$S, 681.16; found, 681.1. | |
| 5-8 | biphenyl-2-ylcarbamic acid 1-(2-{4-[(toluene-4-sulfonylamino)methyl]phenylcarbamoyl}ethyl)piperidin-4-yl ester. MS m/z: [M + H$^+$] calcd for C$_{35}$H$_{38}$N$_4$O$_5$S, 627.26; found, 627.2. | |
| 5-9 | biphenyl-2-ylcarbamic acid 1-(2-{4-[(thiophene-2-sulfonylamino)methyl]phenylcarbamoyl}ethyl)piperidin-4-yl ester. MS m/z: [M + H$^+$] calcd for C$_{32}$H$_{34}$N$_4$O$_5$S$_2$, 619.20; found, 619.1. | |
| 5-10 | biphenyl-2-ylcarbamic acid 1-{2-[4-(benzenesulfonylaminomethyl)phenylcarbamoyl]ethyl}piperidin-4-yl ester. MS m/z: [M + H$^+$] calcd for C$_{34}$H$_{36}$N$_4$O$_5$S, 613.24; found, 613.2. | |
| 5-11 | biphenyl-2-ylcarbamic acid 1-{2-[4-(methanesulfonylaminomethyl)phenylcarbamoyl]ethyl}piperidin-4-yl ester. MS m/z: [M + H$^+$] calcd for C$_{29}$H$_{34}$N$_4$O$_5$S, 551.23; found, 551.1. | |

| # | Name | —NR⁶R⁷ |
|---|---|---|
| 5-12 | biphenyl-2-ylcarbamic acid 1-{2-[4-(trifluoromethane-sulfonylaminomethyl)phenylcarbamoyl]ethyl}piperidin-4-yl ester. MS m/z: [M + H⁺] calcd for C₂₉H₃₁F₃N₄O₅S, 605.20; found, 605.1. | trifluoromethanesulfonylamino group |
| 5-13 | biphenyl-2-ylcarbamic acid 1-(2-{4-[(propane-1-sulfonyl-amino)methyl]phenylcarbamoyl}ethyl)piperidin-4-yl ester. MS m/z: [M + H⁺] calcd for C₃₁H₃₈N₄O₅S, 579.26; found, 579.2. | propane-1-sulfonylamino group |
| 5-14 | biphenyl-2-ylcarbamic acid 1-(2-{4-[(propane-2-sulfonyl-amino)methyl]phenylcarbamoyl}ethyl)piperidin-4-yl ester. MS m/z: [M + H⁺] calcd for C₃₁H₃₈N₄O₅S, 579.26; found, 579.2. | propane-2-sulfonylamino group |
| 5-15 | biphenyl-2-ylcarbamic acid 1-[2-(4-{[(pyridin-2-yl-methyl)amino]methyl}phenylcarbamoyl)ethyl]piperidin-4-yl ester. MS m/z: [M + H⁺] calcd for C₃₄H₃₇N₅O₃, 564.29; found, 564.2. | (pyridin-2-ylmethyl)amino group |
| 5-16 | biphenyl-2-ylcarbamic acid 1-[2-(4-{[(pyridin-3-yl-methyl)amino]methyl}phenylcarbamoyl)ethyl]piperidin-4-yl ester. MS m/z: [M + H⁺] calcd for C₃₄H₃₇N₅O₃, 564.29; found, 564.2. | (pyridin-3-ylmethyl)amino group |
| 5-17 | biphenyl-2-ylcarbamic acid 1-[2-(4-{[(pyridin-4-yl-methyl)amino]methyl}phenylcarbamoyl)ethyl]piperidin-4-yl ester. MS m/z: [M + H⁺] calcd for C₃₄H₃₇N₅O₃, 564.29; found, 564.2. | (pyridin-4-ylmethyl)amino group |
| 5-18 | biphenyl-2-ylcarbamic acid 1-[2-(4-{[(benzo[1,3]dioxol-5-ylmethyl)amino]methyl}phenylcarbamoyl)ethyl]piperidin-4-yl ester. MS m/z: [M + H⁺] calcd for C₃₆H₃₈N₄O₅, 607.28; found, 607.2. | (benzo[1,3]dioxol-5-ylmethyl)amino group |
| 5-19 | biphenyl-2-ylcarbamic acid 1-[2-(4-{[(1H-indol-7-yl-methyl)amino]methyl}phenylcarbamoyl)ethyl]piperidin-4-yl ester. MS m/z: [M + H⁺] calcd for C₃₇H₃₉N₅O₃, 602.31; found, 602.2. | (1H-indol-7-ylmethyl)amino group |
| 5-20 | biphenyl-2-ylcarbamic acid 1-{2-[4-(isobutylamino-methyl)phenylcarbamoyl]ethyl}piperidin-4-yl ester. MS m/z: [M + H⁺] calcd for C₃₂H₄₀N₄O₃, 529.31; found, 529.2. | isobutylamino group |
| 5-21 | biphenyl-2-ylcarbamic acid 1-[2-(4-{[(thiophen-2-yl-methyl)amino]methyl}phenylcarbamoyl)ethyl]piperidin-4-yl ester. MS m/z: [M + H⁺] calcd for C₃₃H₃₆N₄O₃S, 569.25; found, 569.2. | (thiophen-2-ylmethyl)amino group |
| 5-22 | biphenyl-2-ylcarbamic acid 1-(2-{4-[(3,3,3-trifluoro-propylamino)methyl]phenylcarbamoyl}ethyl)piperidin-4-yl ester. MS m/z: [M + H⁺] calcd for C₃₁H₃₅F₃N₄O₃, 569.27; found, 569.2. | (3,3,3-trifluoropropyl)amino group |
| 5-23 | biphenyl-2-ylcarbamic acid 1-(2-{4-[(2-methylamino-ethanesulfonylamino)methyl]phenylcarbamoyl}ethyl)piperidin-4-yl ester. MS m/z: [M + H⁺] calcd for C₃₁H₃₉N₅O₅S, 594.27; found, 594.2. | (2-methylaminoethanesulfonyl)amino group |

Example 6

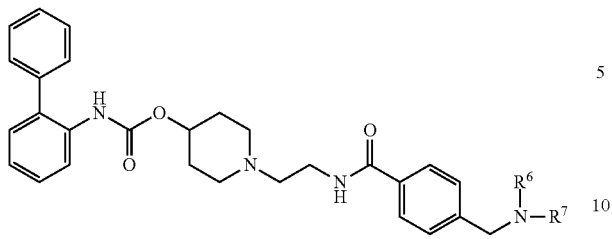

Using the procedure of Example 1, substituting 3-(4-formylphenyl)propionic acid in place of 4-carboxybenzaldehyde in Preparation 9 and using that product in place of the product of Preparation 5, and substituting the appropriate amine in the reductive amination step, the following compounds were prepared.

| # | Name | —NR⁶R⁷ |
|---|------|--------|
| 6-1 | biphenyl-2-ylcarbamic acid 1-{2-[3-(4-methylamino-methylphenyl)propionylamino]ethyl}piperidin-4-yl ester. MS m/z: [M + H⁺] calcd for $C_{31}H_{38}N_4O_3$, 515.29; found, 515.2. | —NH(CH₃) |
| 6-2 | biphenyl-2-ylcarbamic acid 1-{2-[3-(4-ethylaminomethyl-phenyl)propionylamino]ethyl}piperidin-4-yl ester. MS m/z: [M + H⁺] calcd for $C_{32}H_{40}N_4O_3$, 529.31; found, 529.2. | —NH(CH₂CH₃) |
| 6-3 | biphenyl-2-ylcarbamic acid 1-(2-{3-[4-(isopropylamino-methyl)phenyl]propionylamino}ethyl)piperidin-4-yl ester. MS m/z: [M + H⁺] calcd for $C_{33}H_{42}N_4O_3$, 543.33; found, 543.2. | isopropylamino |
| 6-4 | biphenyl-2-ylcarbamic acid 1-{2-[3-(4-cyclopropylamino-methylphenyl)propionylamino]ethyl}piperidin-4-yl ester. MS m/z: [M + H⁺] calcd for $C_{33}H_{40}N_4O_3$, 541.31; found, 541.2. | cyclopropylamino |
| 6-5 | biphenyl-2-ylcarbamic acid 1-[2-(3-{4-[(cyclopropyl-methylamino)methyl]phenyl}propionylamino)ethyl]piperidin-4-yl ester. MS m/z: [M + H⁺] calcd for $C_{34}H_{42}N_4O_3$, 555.33; found, 555.2. | cyclopropylmethylamino |
| 6-6 | biphenyl-2-ylcarbamic acid 1-{2-[3-(4-cyclopentylamino-methylphenyl)propionylamino]ethyl}piperidin-4-yl ester. MS m/z: [M + H⁺] calcd for $C_{35}H_{44}N_4O_3$, 569.34; found, 569.4. | cyclopentylamino |
| 6-7 | biphenyl-2-ylcarbamic acid 1-[2-(3-{4-[(2-hydroxyethyl-amino)methyl]phenyl}propionylamino)ethyl]piperidin-4-yl ester. MS m/z: [M + H⁺] calcd for $C_{32}H_{40}N_4O_4$, 545.31; found, 545.2. | —NH[(CH₂)₂OH] |
| 6-8 | biphenyl-2-ylcarbamic acid 1-[2-(3-{4-[(2-methoxyethyl-amino)methyl]phenyl}propionylamino)ethyl]piperidin-4-yl ester. MS m/z: [M + H⁺] calcd for $C_{33}H_{42}N_4O_4$, 559.32; found, 559.2. | 2-methoxyethylamino |
| 6-9 | biphenyl-2-ylcarbamic acid 1-(2-{3-[4-(4-acetyl-[1,4]diazepan-1-ylmethyl)phenyl]propionylamino}ethyl)piperidin-4-yl ester. MS m/z: [M + H⁺] calcd for $C_{37}H_{47}N_5O_4$, 626.36; found, 626.4. | 4-acetyldiazepanyl |
| 6-10 | biphenyl-2-ylcarbamic acid 1-(2-{3-[4-(4-acetyl-piperazin-1-ylmethyl)phenyl]propionylamino}ethyl)piperidin-4-yl ester. MS m/z: [M + H⁺] calcd for $C_{36}H_{45}N_5O_4$, 612.35; found, 612.4. | 4-acetylpiperazinyl |
| 6-11 | biphenyl-2-ylcarbamic acid 1-[2-(3-{4-[(carbamoyl-methylamino)methyl]phenyl}propionylamino)ethyl]piperidin-4-yl ester. MS m/z: [M + H⁺] calcd for $C_{32}H_{39}N_5O_4$, 558.30; found, 558.2. | carbamoylmethylamino |

-continued

| # | Name | —NR⁶R⁷ |
|---|------|--------|
| 6-12 | biphenyl-2-ylcarbamic acid 1-(2-{3-[4-(4-dimethyl-carbamoylmethylpiperazin-1-ylmethyl)phenyl]propionyl-amino}ethyl)piperidin-4-yl ester. MS m/z: [M + H⁺] calcd for C₃₈H₅₀N₆O₄, 655.39; found, 655.4. | 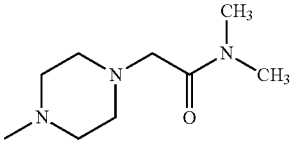 |
| 6-13 | 4-[4-(2-{2-[4-(biphenyl-2-ylcarbamoyloxy)piperidin-1-yl]ethylcarbamoyl}ethyl)benzyl]piperazine-1-carboxylic acid methyl ester. MS m/z: [M + H⁺] calcd for C₃₆H₄₅N₅O₅, 628.34; found, 628.2. | 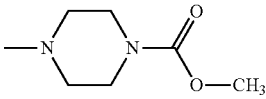 |
| 6-14 | biphenyl-2-ylcarbamic acid 1-(2-{3-[4-(1,1-dioxo-1λ⁶-thiomorpholin-4-ylmethyl)phenyl]propionylamino}ethyl)piperidin-4-yl ester. MS m/z: [M + H⁺] calcd for C₃₄H₄₂N₄O₅S, 619.29; found, 619.2. | 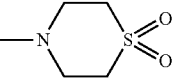 |
| 6-15 | biphenyl-2-ylcarbamic acid 1-{2-[3-(4-{[bis-(2-hydroxy-ethyl)amino]methyl}phenyl)propionylamino]ethyl}piperidin-4-yl ester. MS m/z: [M + H⁺] calcd for C₃₄H₄₄N₄O₅, 589.33; found, 589.2. | —N[(CH₂)₂OH]₂ |
| 6-16 | biphenyl-2-ylcarbamic acid 1-(2-{3-[4-(4-dimethyl-carbamoylpiperazin-1-ylmethyl)phenyl]propionylamino}ethyl)piperidin-4-yl ester. MS m/z: [M + H⁺] calcd for C₃₇H₄₈N₆O₄, 641.37; found, 641.4. | 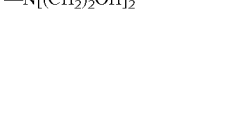 |
| 6-17 | biphenyl-2-ylcarbamic acid 1-[2-(3-{4-[4-(pyrrolidine-1-carbonyl)piperazin-1-ylmethyl]phenyl}propionylamino)ethyl]piperidin-4-yl ester. MS m/z: [M + H⁺] calcd for C₃₉H₅₀N₆O₄, 667.39; found, 667.4. | 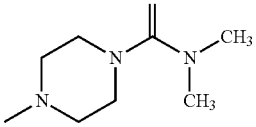 |
| 6-18 | biphenyl-2-ylcarbamic acid 1-[2-(3-{4-[4-(piperidine-1-carbonyl)piperazin-1-ylmethyl]phenyl}propionylamino)ethyl]piperidin-4-yl ester. MS m/z: [M + H⁺] calcd for C₄₀H₅₂N₆O₄, 681.41; found, 681.4. | 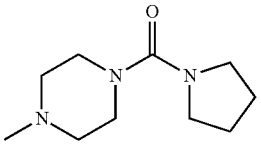 |
| 6-19 | biphenyl-2-ylcarbamic acid 1-[2-(3-{4-[4-(morpholine-4-carbonyl)piperazin-1-ylmethyl]phenyl}propionylamino)ethyl]piperidin-4-yl ester. MS m/z: [M + H⁺] calcd for C₃₉H₅₀N₆O₅, 683.38; found, 683.4. | 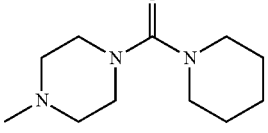 |

Preparation 16

4-(Formylphenyl)acetic Acid

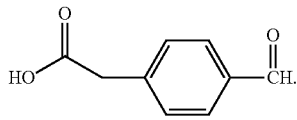

4-(formylphenyl)acetic acid methyl ester was prepared as described in *Chem. Commun.* 7:669-670 (2001). To a solution of (4-formylphenyl)acetic acid methyl ester (2.76 g, 14.4 mmol) in 40 mL of MeOH was added 1N NaOH (30 ml). The solution was stirred at room temperature for 16 hours and then the MeOH was removed in vacuo. The aqueous layer was then washed with EtOAc (40 mL), followed by wash with DCM (40 mL). The aqueous layer was then acidified to pH=1 using 1N HCl. The product was extracted using DCM washes (3×50 mL) and the organic layer washed with water (100 mL), NaCl (sat.) (100 mL), dried over MgSO₄ and then filtered. The solvent removed under reduced pressure. The crude material was sufficiently pure to use without further purification. The title compound was obtained in 78% yield (2.0 g, 11.2 mmol).

Example 7

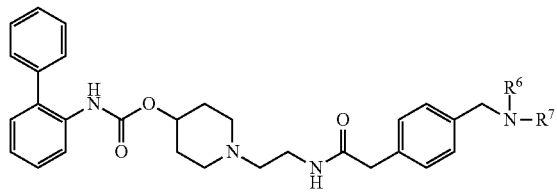

Using the procedure of Example 1, substituting 4-(formylphenyl)acetic acid (prepared as described in Preparation 16) in place of 4-carboxybenzaldehyde in Preparation 9 and using that product in place of the product of Preparation 5, and substituting the appropriate amine in the reductive amination step, the following compounds were prepared.

| # Name | —NR$^6$R$^7$ |
|---|---|
| 7-1 biphenyl-2-ylcarbamic acid 1-{2-[2-(4-methylaminomethyl-phenyl)acetylamino]ethyl} piperidin-4-yl ester. MS m/z: [M + H$^+$] calcd for C$_{30}$H$_{36}$N$_4$O$_3$, 501.28 found, 501.2. | —NH(CH$_3$) |
| 7-2 biphenyl-2-ylcarbamic acid 1-{2-[2-(4-ethylaminomethyl-phenyl)acetylamino]ethyl} piperidin-4-yl ester. MS m/z: [M + H$^+$] calcd for C$_{31}$H$_{38}$N$_4$O$_3$, 515.29; found, 515.2. | —NH(CH$_2$CH$_3$) |
| 7-3 biphenyl-2-ylcarbamic acid 1-[2-(2-{4-[(2-hydroxyethylamino) methyl]phenyl}acetylamino) ethyl]piperidin-4-yl ester. MS m/z: [M + H$^+$] calcd for C$_{31}$H$_{38}$N$_4$O$_4$, 531.29; found, 531.2. | —NH[(CH$_2$)$_2$OH] |
| 7-4 biphenyl-2-ylcarbamic acid 1-[2-(2-{4-[(2-methoxyethyl-amino)methyl]phenyl}acetyl-amino)ethyl]piperidin-4-yl ester. MS m/z: [M + H$^+$] calcd for C$_{32}$H$_{40}$N$_4$O$_4$, 545.31; found, 545.2. | 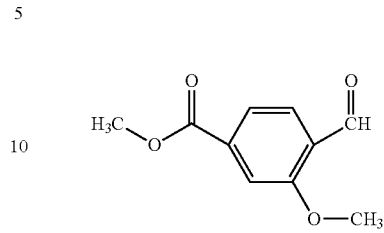 |
| 7-5 biphenyl-2-ylcarbamic acid 1-[2-(2-{4-[(carbamoylmethyl-amino)methyl]phenyl}acetyl-amino)ethyl]piperidin-4-yl ester. MS m/z: [M + H$^+$] calcd for C$_{31}$H$_{37}$N$_5$O$_4$, 544.28; found, 544.2. | |
| 7-6 biphenyl-2-ylcarbamic acid 1-(2-{2-[4-(4-dimethylcarbamoyl-piperazin-1-ylmethyl)phenyl] acetylamino}ethyl)piperidin-4-yl ester. MS m/z: [M + H$^+$] calcd for C$_{36}$H$_{46}$N$_6$O$_4$, 627.36; found, 627.4. | 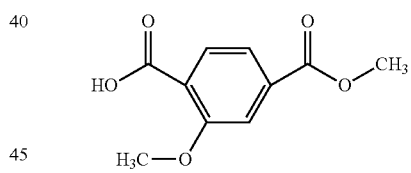 |

Preparation 17

4-Formyl-3-methoxybenzoic Acid Methyl Ester

To a stirred solution of 4-bromo-3-methoxybenzoic acid (15.0 g, 58 mmol) in DMSO (150 mL) was added NaHCO$_3$ (20.0 g, 230 mmol). This was heated to 80° C. for 18 hours. The reaction was then cooled to room temperature and the solvent removed under reduced pressure. The crude reaction mixture was then dissolved in DCM (200 mL) and washed with 1N HCl (100 mL), water (100 mL), NaCl (sat.) (100 mL), dried over MgSO$_4$ and then filtered. The solvent was removed under reduced pressure. The crude material was sufficiently pure to use without further purification. The title intermediate was obtained in 79% yield (8.9 g, 45.8 mmol).

Preparation 18

2-Methoxyterephthalic Acid 4-Methyl Ester

To a stirred solution of 4-formyl-3-methoxybenzoic acid methyl ester (5.0 g, 26 mmol; prepared as described in Preparation 17) in tert-butyl alcohol (200 mL) was added NaH$_2$PO$_4$·2H$_2$O (3.6 g, 26 mmol), water (50 mL), 2-methyl-2-butene (11 mL, 104 mmol), and finally NaClO$_2$ (7.02 g, 78 mmol). The reaction was allowed to stir at room temperature for 4 hours. The solvent was then removed under reduced pressure. The crude reaction mixture was then dissolved in DCM (200 mL) and the product was extracted with 1N NaOH (200 mL). The aqueous layer was washed with DCM (200 mL) and then neutralized with 6N HCl (~40 mL) and the product extracted with DCM (200 mL). The organic layer was then washed with water (100 mL), NaCl (sat.) (100 mL), dried over MgSO$_4$ and then filtered. The solvent was removed under reduced pressure. The crude material was sufficiently pure to use without further purification. The title intermediate was obtained in 47% yield (2.4 g, 12.3 mmol).

Preparation 19

N-{2-[4-(Biphenyl-2-ylcarbarnoyloxy)piperidin-1-yl]ethyl}-3-methoxy-N-methylterephthalamic Acid Methyl Ester

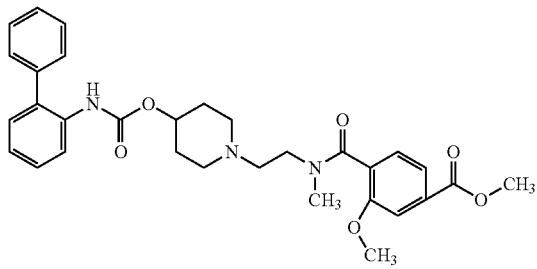 [SMILES: COC(=O)c1ccc(C(=O)N(C)CCN2CCC(OC(=O)Nc3ccccc3-c3ccccc3)CC2)c(OC)c1]

To a stirred solution of 2-methoxyterephthalic acid 4-methyl ester (450 mg, 2.1 mmol; prepared as described in Preparation 18) in DMF (10 mL) was added EDC (630 mg, 3.3 mmol), HOAt (2.4 mL, 1.18 mmol, 0.5M in DMF) and DIPEA (1.3 mL, 7.05 mmol). When the mixture was homogenous, a solution of biphenyl-2-ylcarbamic acid 1-(2-methylaminoethyl)piperidin-4-yl ester (830 mg, 2.4 mmol; prepared as described in Preparation 4) was added slowly. The reaction mixture was stirred at room temperature for 16 hours and then washed with water (100 mL), 1N HCl (100 mL), 1N NaOH (100 mL), brine (100 mL), dried over MgSO$_4$, filtered and concentrated to afford the title intermediate in 89% yield (1.04 g, 1.9 mmol). MS m/z: [M+H$^+$] calcd for C$_{31}$H$_{35}$N$_3$O$_6$, 545.6; found, 546.6.

Preparation 20

Biphenyl-2-ylcarbamic Acid 1-{2-[(4-hydroxymethyl-2-methoxybenzoyl)methylamino]ethyl}piperidin-4-yl Ester

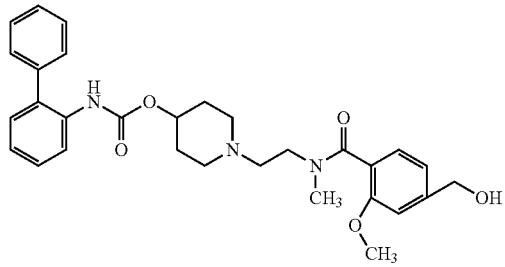 [SMILES: COc1cc(CO)ccc1C(=O)N(C)CCN1CCC(OC(=O)Nc2ccccc2-c2ccccc2)CC1]

To a stirred solution of N-{2-[4-(biphenyl-2-ylcarbamoyloxy)piperidin-1-yl]ethyl}-3-methoxy-n-methylterephthalamic acid methyl ester (1.0 g, 1.8 mmol; prepared as described in Preparation 19) in THF (100 mL) at 0° C., was added MeOH (57 µL, 1.8 mmol), followed by LiAlH$_4$ (1.8 mL, 1.8 mmol, 1.0M in THF) was added. The ice bath was removed, and the reaction mixture was stirred at room temperature for 1 hour. The reaction was quenched with 1N HCl(aq) at 0° C. until no more bubbling, and stirring was continued for 10 minutes. The solvent was removed under reduced pressure. The crude reaction mixture was taken up in DCM (100 mL) and washed with water (100 mL), NaCl (sat.) (100 mL), dried over MgSO$_4$ and then filtered. The solvent was removed under reduced pressure. The crude material was sufficiently pure to use without further purification. The title intermediate was obtained in 89% yield (831 mg, 1.6 mmol). MS m/z: [M+H$^+$] calcd for C$_{30}$H$_{35}$N$_3$O$_5$, 517.6; found, 518.6.

Preparation 21

Biphenyl-2-ylcarbamic acid 1-{2-[(4-formyl-2-methoxybenzoyl)methylamino]ethyl}piperidin-4-yl Ester

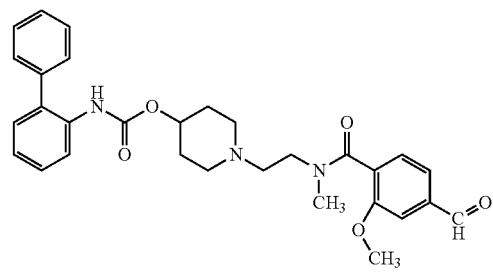 [SMILES: COc1cc(C=O)ccc1C(=O)N(C)CCN1CCC(OC(=O)Nc2ccccc2-c2ccccc2)CC1]

To a stirred solution of biphenyl-2-ylcarbamic acid 1-{2-[(4-hydroxymethyl-2-methoxybenzoyl)methylamino]ethyl}piperidin-4-yl ester (78 mg, 1.5 mmol; prepared as described in Preparation 20) in DCM (2.5 mL) at −15° C. was added DMSO (130 µL, 22.5 mmol), and DIPEA (130 µL, 7.5 mmol). To the solution was added sulfur trioxide-pyridine complex (240 mg, 15 mmol). After 30 minutes, the reaction mixture was quenched with water (~3 mL). Two layers were separated, the organic layer was dried over MgSO$_4$; filtered and the title intermediate was used directly in the next reaction.

Example 8

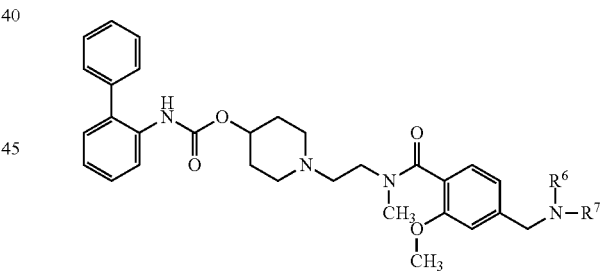

Using the procedure of Example 1, but substituting biphenyl-2-ylcarbamic acid 1-{(2-[(4-formyl-2-methoxybenzoyl)methylamino]ethyl}piperidin-4-yl ester (prepared as described in Preparation 21) in place of the product of Preparation 5, and substituting the appropriate amine in the reductive amination step, the following compounds were prepared.

| # | Name | —NR$^6$R$^7$ |
|---|---|---|
| 8-1 | biphenyl-2-ylcarbamic acid 1-{2-[(2-methoxy-4-methylaminomethylbenzoyl)methylamino]ethyl}piperidin-4-yl ester. MS m/z: [M + H$^+$] calcd for C$_{31}$H$_{38}$N$_4$O$_4$, 531.29; found, 531.2. | —NH(CH$_3$) |

-continued

| # | Name | —NR⁶R⁷ |
|---|------|--------|
| 8-2 | biphenyl-2-ylcarbamic acid 1-(2-{[2-methoxy-4-(3-oxopiperazin-1-ylmethyl)benzoyl]methylamino}ethyl)piperidin-4-yl ester. MS m/z: [M + H⁺] calcd for C₃₄H₄₁N₅O₅, 600.31; found, 600.2. | 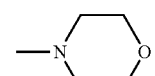 |
| 8-3 | biphenyl-2-ylcarbamic acid 1-[2-({4-[(2-hydroxyethylamino)methyl]-2-methoxybenzoyl}methylamino)ethyl]piperidin-4-yl ester. MS m/z: [M + H⁺] calcd for C₃₂H₄₀N₄O₅, 561.30; found, 561.2. | —NH[(CH₂)₂OH] |

| # | Name | —NR⁶R⁷ |
|---|------|--------|
| 9-1 | biphenyl-2-ylcarbamic acid 1-[2-(2-methoxy-4-methylaminomethylbenzoylamino)ethyl]piperidin-4-yl ester. MS m/z: [M + H⁺] calcd for C₃₀H₃₆N₄O₄, 517.27; found, 517.2. | —NH(CH₃) |
| 9-2 | biphenyl-2-ylcarbamic acid 1-{2-[2-methoxy-4-(3-oxopiperazin-1-ylmethyl)benzoylamino]ethyl}piperidin-4-yl ester. MS m/z: [M + H⁺] calcd for C₃₃H₃₉N₅O₅, 586.30; found, 586.2. | 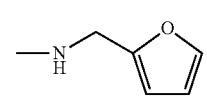 |
| 9-3 | biphenyl-2-ylcarbamic acid 1-(2-{4-[(2-hydroxyethylamino)methyl]-2-methoxy-benzoylamino}ethyl)piperidin-4-yl ester. MS m/z: [M + H⁺] calcd for C₃₁H₃₈N₄O₅, 547.28; found, 547.2. | —NH[(CH₂)₂OH] |

Example 9

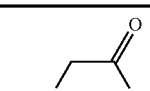

Using the procedure of Example 8, but substituting biphenyl-2-ylcarbamic acid 1-(2-aminoethyl)piperidin-4-yl ester (prepared as described in Preparation 7) in place of the product of Preparation 4 in Preparation 19 and substituting the appropriate amine in the reductive amination step, the following compounds were prepared.

Example 10

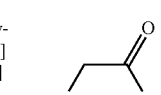

Using the procedure of Example 1, but substituting 5-formylpyridine-2-carboxylic acid in place of 4-carboxybenzaldehyde in Preparation 5, and substituting the appropriate amine in the reductive amination step, the following compounds were prepared.

| # | Name | —NR⁶R⁷ |
|---|------|--------|
| 10-1 | biphenyl-2-ylcarbamic acid 1-{2-[methyl(5-methylaminomethylpyridine-2-carbonyl)amino]ethyl}piperidin-4-yl ester. MS m/z: [M + H⁺] calcd for C₂₉H₃₅N₅O₃, 502.27; found, 502.2. | —NH(CH₃) |
| 10-2 | biphenyl-2-ylcarbamic acid 1-{2-[(5-diethylaminomethyl-pyridine-2-carbonyl)methylamino]ethyl}piperidin-4-yl ester. MS m/z: [M + H⁺] calcd for C₃₂H₄₁N₅O₃, 544.32; found, 544.2. | —N(CH₂CH₃)₂ |
| 10-3 | biphenyl-2-ylcarbamic acid 1-[2-({5-[(2-hydroxyethyl-amino)methyl]pyridine-2-carbonyl}methylamino)ethyl]piperidin-4-yl ester. MS m/z: [M + H⁺] calcd for C₃₀H₃₇N₅O₄, 532.28; found, 532.2. | —NH[(CH₂)₂OH] |
| 10-4 | biphenyl-2-ylcarbamic acid 1-{2-[methyl(5-morpholin-4-ylmethylpyridine-2-carbonyl)amino]ethyl}piperidin-4-yl ester. MS m/z: [M + H⁺] calcd for C₃₂H₃₉N₅O₄, 558.30; found, 558.2. | 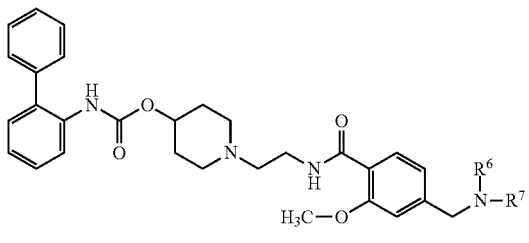 |
| 10-5 | biphenyl-2-ylcarbamic acid 1-{2-[(5-{[(furan-2-yl-methyl)amino]methyl}pyridine-2-carbonyl)methyl-amino]ethyl}piperidin-4-yl ester. MS m/z: [M + H⁺] calcd for C₃₃H₃₇N₅O₄, 568.28; found, 568.2. | 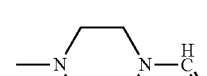 |
| 10-6 | biphenyl-2-ylcarbamic acid 1-(2-{[5-(4-formylpiperazin-1-ylmethyl)pyridine-2-carbonyl]methylamino}ethyl)piperidin-4-yl ester. MS m/z: [M + H⁺] calcd for C₃₃H₄₀N₆O₄, 585.31; found, 585.2. | |

-continued

| # | Name | —NR⁶R⁷ |
|---|---|---|
| 10-7 | biphenyl-2-ylcarbamic acid 1-{2-[(5-{[bis-(2-hydroxy-ethyl)amino]methyl}pyridine-2-carbonyl)methylamino]ethyl}piperidin-4-yl ester. MS m/z: [M + H⁺] calcd for $C_{32}H_{41}N_5O_5$, 576.31; found, 576.2. | —N[(CH$_2$)$_2$OH]$_2$ |
| 10-8 | biphenyl-2-ylcarbamic acid 1-(2-{methyl-[5-(3-oxo-piperazin-1-ylmethyl)pyridine-2-carbonyl]amino}ethyl)piperidin-4-yl ester. MS m/z: [M + H⁺] calcd for $C_{32}H_{38}N_6O_4$, 571.30; found, 571.2. | (3-oxopiperazinyl structure) |
| 10-9 | biphenyl-2-ylcarbamic acid 1-(2-{[5-(4-acetyl-[1,4]diazepan-1-ylmethyl)pyridine-2-carbonyl]methylamino}ethyl)piperidin-4-yl ester. MS m/z: [M + H⁺] calcd for $C_{35}H_{44}N_6O_4$, 613.34; found, 613.4. | (4-acetyl-diazepanyl structure) |
| 10-10 | biphenyl-2-ylcarbamic acid 1-(2-{[5-(4-acetylpiperazin-1-ylmethyl)pyridine-2-carbonyl]methylamino}ethyl)piperidin-4-yl ester. MS m/z: [M + H⁺] calcd for $C_{34}H_{42}N_6O_4$, 599.33; found, 599.2. | (4-acetylpiperazinyl structure) |
| 10-11 | biphenyl-2-ylcarbamic acid 1-(2-{[5-(4-methanesulfonyl-piperazin-1-ylmethyl)pyridine-2-carbonyl]methylamino}ethyl)piperidin-4-yl ester. MS m/z: [M + H⁺] calcd for $C_{33}H_{42}N_6O_5S$, 635.29; found, 635.2. | (4-methanesulfonyl-piperazinyl structure) |
| 10-12 | 4-[6-({2-[4-(biphenyl-2-ylcarbamoyloxy)piperidin-1-yl]ethyl}methylcarbamoyl)pyridin-3-ylmethyl]piperazine-1-carboxylic acid methyl ester. MS m/z: [M + H⁺] calcd for $C_{34}H_{42}N_6O_5$, 615.32; found, 615.2. | (methyl piperazine-1-carboxylate structure) |

Example 11

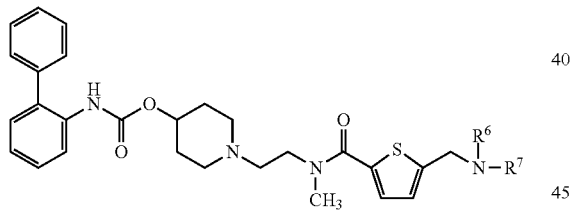

Using the procedure of Example 1, but substituting 5-formylthiophene-2-carboxylic acid in place of 4-carboxybenzaldehyde in Preparation 5, and substituting the appropriate amine in the reductive amination step, the following compounds were prepared.

| # | Name | —NR⁶R⁷ |
|---|---|---|
| 11-1 | biphenyl-2-ylcarbamic acid 1-{2-[methyl-(5-methyl-aminomethylthiophene-2-carbonyl)amino]ethyl}piperidin-4-yl ester. MS m/z: [M + H⁺] calcd for $C_{28}H_{34}N_4O_3S$, 507.24; found, 507.2. | —NH(CH$_3$) |
| 11-2 | biphenyl-2-ylcarbamic acid 1-{2-[(5-diethylaminomethyl-thiophene-2-carbonyl)methylamino]ethyl}piperidin-4-yl ester. MS m/z: [M + H⁺] calcd for $C_{31}H_{40}N_4O_3S$, 549.28; found, 549.2. | —N(CH$_2$CH$_3$)$_2$ |
| 11-3 | biphenyl-2-ylcarbamic acid 1-[2-({5-[(2-hydroxyethyl-amino)methyl]thiophene-2-carbonyl}methylamino)ethyl]piperidin-4-yl ester. MS m/z: [M + H⁺] calcd for $C_{29}H_{36}N_4O_4S$, 537.25; found, 537.2. | —NH[(CH$_2$)$_2$OH] |

| # | Name | —NR⁶R⁷ |
|---|------|--------|
| 11-4 | biphenyl-2-ylcarbamic acid 1-{2-[methyl-(5-morpholin-4-ylmethylthiophene-2-carbonyl)amino]ethyl}piperidin-4-yl ester. MS m/z: [M + H⁺] calcd for $C_{31}H_{38}N_4O_4S$, 563.26; found, 563.2. | |
| 11-5 | biphenyl-2-ylcarbamic acid 1-{2-[(5-{[(furan-2-yl-methyl)amino]methyl}thiophene-2-carbonyl)methyl-amino]ethyl}piperidin-4-yl ester. MS m/z: [M + H⁺] calcd for $C_{32}H_{36}N_4O_4S$, 573.25; found, 573.2. | |
| 11-6 | biphenyl-2-ylcarbamic acid 1-(2-{[5-(4-formylpiperazin-1-ylmethyl)thiophene-2-carbonyl]methylamino}ethyl) piperidin-4-yl ester. MS m/z: [M + H⁺] calcd for $C_{32}H_{39}N_5O_4S$, 590.27; found, 590.2. | |
| 11-7 | biphenyl-2-ylcarbamic acid 1-{2-[(5-{[bis-(2-hydroxy-ethyl)amino]methyl}thiophene-2-carbonyl)methylamino] ethyl}piperidin-4-yl ester. MS m/z: [M + H⁺] calcd for $C_{31}H_{40}N_4O_5S$, 581.27; found, 581.2. | —N[(CH₂)₂OH]₂ |
| 11-8 | biphenyl-2-yl-carbamic acid 1-(2-{methyl-[5-(3-oxo-piperazin-1-ylmethyl)thiophene-2-carbonyl]amino}ethyl) piperidin-4-yl ester. MS m/z: [M + H⁺] calcd for $C_{31}H_{37}N_5O_4S$, 576.26; found, 576.2. | |
| 11-9 | biphenyl-2-ylcarbamic acid 1-(2-{[5-(4-acetyl-[1,4] diazepan-1-ylmethyl)thiophene-2-carbonyl}methyl-amino}ethyl)piperidin-4-yl ester. MS m/z: [M + H⁺] calcd for $C_{34}H_{43}N_5O_4S$, 618.30; found, 618.2. | |
| 11-10 | 4-[5-({2-[4-(biphenyl-2-ylcarbamoyloxy)piperidin-1-yl] ethyl}methylcarbamoyl)thiophen-2-ylmethyl]piperazine-1-carboxylic acid methyl ester. MS m/z: [M + H⁺] calcd for $C_{33}H_{41}N_5O_5S$, 620.28; found, 620.2. | |
| 11-11 | biphenyl-2-ylcarbamic acid 1-(2-{[5-(1,1-dioxo-1λ⁶-thio-morpholin-4-ylmethyl)thiophene-2-carbonyl]methyl-amino}ethyl)piperidin-4-yl ester. MS m/z: [M + H⁺] calcd for $C_{31}H_{38}N_4O_5S_2$, 611.23; found, 611.2. | |
| 11-12 | biphenyl-2-ylcarbamic acid 1-(2-{[5-(4-acetylpiperazin-1-ylmethyl)thiophene-2-carbonyl]methylamino}ethyl) piperidin-4-yl ester. MS m/z: [M + H⁺] calcd for $C_{33}H_{41}N_5O_4S$, 604.29; found, 604.2. | |
| 11-13 | biphenyl-2-ylcarbamic acid 1-(2-{[5-(4-methanesulfonyl-piperazin-1-ylmethyl)thiophene-2-carbonyl]methyl-amino}ethyl)piperidin-4-yl ester. MS m/z: [M + H⁺] calcd for $C_{32}H_{41}N_5O_5S_2$, 640.26; found, 640.2. | |

Example 12

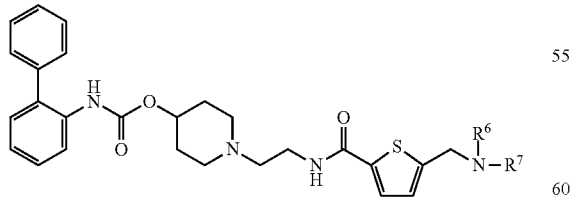

Using the procedure of Example 1, substituting 5-formylthiophene-2-carboxylic acid in place of 4-carboxybenzaldehyde in Preparation 9 and using that product in place of the product of Preparation 5, and substituting the appropriate amine in the reductive amination step, the following compounds were prepared.

| # | Name | —NR⁶R⁷ |
|---|------|--------|
| 12-1 | biphenyl-2-ylcarbamic acid 1-{2-[(5-methylaminomethyl thiophene-2-carbonyl)amino]ethyl}piperidin-4-yl ester. MS m/z: [M + H⁺] calcd for $C_{27}H_{32}N_4O_3S$, 493.22; found, 493.2. | —NH(CH₃) |
| 12-2 | biphenyl-2-ylcarbamic acid 1-[2-({5-[(2-hydroxyethyl amino)methyl]thiophene-2-carbonyl}amino)ethyl] piperidin-4-yl ester. MS m/z; [M + H⁺] calcd for $C_{28}H_{34}N_4O_4S$, 523.23; found, 523.2. | —NH[(CH₂)₂OH] |

Example 13

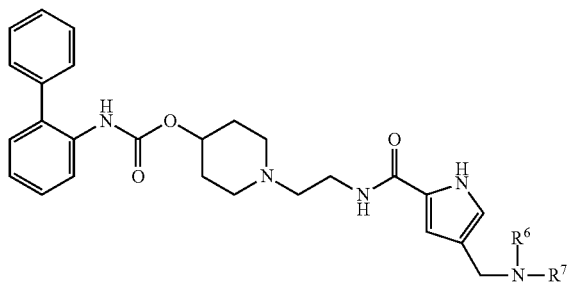

Using the procedure of Example 1, substituting 4-formylpyrrole-2-carboxylic acid in place of 4-carboxybenzaldehyde in Preparation 9 and using that product in place of the product of Preparation 5, and substituting the appropriate amine in the reductive amination step, Compound 13-1 (R⁶=H, R⁷=—CH₃) was prepared: biphenyl-2-ylcarbamic acid 1-{2-[methyl(4-methylamino methyl-1H-pyrrole-2-carbonyl)amino]ethyl}piperidin-4-yl ester. MS m/z: [M+H⁺] calcd for $C_{28}H_{35}N_5O_3$, 490.27; found, 490.2.

Example 14

| # | Name | —NR⁶R⁷ |
|---|------|--------|
| 14-1 | biphenyl-2-ylcarbamic acid 1-{2-[methyl-(5-methylaminomethyl-1H-pyrrole-2-carbonyl)amino] ethyl}piperidin-4-yl ester. MS m/z: [M + H⁺] calcd for $C_{28}H_{35}N_5O_3$, 490.27; found, 490.2. | —NH(CH₃) |
| 14-2 | biphenyl-2-ylcarbamic acid 1-(2-{[5-(4-acetylpiperazin-1-ylmethyl)-1H-pyrrole-2-carbonyl]methyl-amino}ethyl)piperidin-4-yl ester. MS m/z: [M + H⁺] calcd for $C_{33}H_{42}N_6O_4$, 587.33; found, 587.2. | ![piperazine structure] |
| 14-3 | biphenyl-2-ylcarbamic acid 1-[2-({5-[(2-hydroxyethylamino) methyl]-1H-pyrrole-2-carbonyl} methylamino)ethyl]piperidin-4-yl ester. MS m/z: [M + H⁺] calcd for $C_{29}H_{37}N_5O_4$, 520.28; found, 520.2. | —NH[(CH₂)₂OH] |

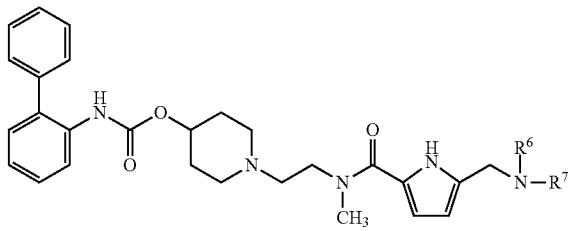

Using the procedure of Example 1, but substituting 5-formylpyrrole-2-carboxylic acid in place of 4-carboxybenzaldehyde in Preparation 5, and substituting the appropriate amine in the reductive amination step, the following compounds were prepared.

Example 15

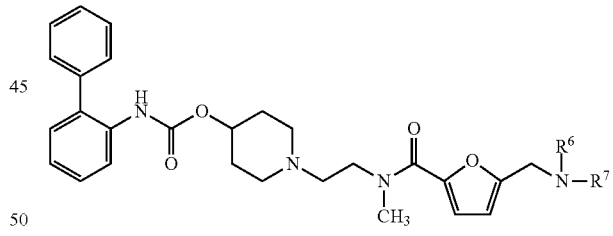

Using the procedure of Example 1, but substituting 5-formylfuran-2-carboxylic acid in place of 4-carboxybenzaldehyde in Preparation 5, and substituting the appropriate amine in the reductive amination step, the following compounds were prepared.

| # | Name | —NR⁶R⁷ |
|---|------|--------|
| 15-1 | biphenyl-2-ylcarbamic acid 1-{2-[methyl(5-methylamino-methylfuran-2-carbonyl)amino]ethyl}piperidin-4-yl ester. MS m/z: [M + H⁺] calcd for $C_{28}H_{34}N_4O_4$, 491.26; found, 491.6. | —NH(CH₃) |

| # | Name | —NR⁶R⁷ |
|---|---|---|
| 15-2 | biphenyl-2-ylcarbamic acid 1-{2-[(5-diethylaminomethyl-furan-2-carbonyl)methylamino]ethyl}piperidin-4-yl ester. MS m/z: [M + H⁺] calcd for $C_{31}H_{40}N_4O_4$, 533.31; found, 533.2. | —N(CH₂CH₃)₂ |
| 15-3 | biphenyl-2-ylcarbamic acid 1-[2-({5-[(2-hydroxyethyl-amino)methyl]furan-2-carbonyl}methylamino)ethyl]piperidin-4-yl ester. MS m/z: [M + H⁺] calcd for $C_{29}H_{36}N_4O_5$, 521.27; found, 521.2. | —NH[(CH₂)₂OH] |
| 15-4 | biphenyl-2-ylcarbamic acid 1-{2-[methyl(5-morpholin-4-ylmethylfuran-2-carbonyl)amino]ethyl}piperidin-4-yl ester. MS m/z: [M + H⁺] calcd for $C_{31}H_{38}N_4O_5$, 547.28; found, 547.2. | morpholinyl structure |
| 15-5 | biphenyl-2-ylcarbamic acid 1-{2-[(5-{[(furan-2-yl-methyl)amino]methyl}furan-2-carbonyl)methylamino]ethyl}piperidin-4-yl ester. MS m/z: [M + H⁺] calcd for $C_{32}H_{36}N_4O_5$, 557.27; found, 557.2. | —NH-CH₂-(furan-2-yl) |
| 15-6 | biphenyl-2-ylcarbamic acid 1-(2-{[5-(4-formylpiperazin-1-ylmethyl)furan-2-carbonyl]methylamino}ethyl)piperidin-4-yl ester. MS m/z: [M + H⁺] calcd for $C_{32}H_{39}N_5O_5$, 574.30; found, 574.2. | 4-formylpiperazinyl structure |
| 15-7 | biphenyl-2-ylcarbamic acid 1-{2-[(5-{[bis-(2-hydroxy-ethyl)amino]methyl}furan-2-carbonyl)methylamino]ethyl}piperidin-4-yl ester. MS m/z: [M + H⁺] calcd for $C_{31}H_{40}N_4O_6$, 565.29; found, 565.2. | —N[(CH₂)₂OH]₂ |
| 15-8 | biphenyl-2-yl-carbamic acid 1-(2-{methyl-[5-(3-oxo-piperazin-1-ylmethyl)furan-2-carbonyl]amino}ethyl)piperidin-4-yl ester. MS m/z: [M + H⁺] calcd for $C_{31}H_{37}N_5O_5$, 560.28; found, 560.2. | 3-oxopiperazinyl structure |
| 15-9 | biphenyl-2-ylcarbamic acid 1-(2-{[5-(4-acetyl[1,4]diazepan-1-ylmethyl)furan-2-carbonyl]ethylamino}ethyl)piperidin-4-yl ester. MS m/z: [M + H⁺] calcd for $C_{34}H_{43}N_5O_5$, 602.33; found, 602.4. | 4-acetyl-1,4-diazepanyl structure |
| 15-10 | 4-[5-({2-[4-(biphenyl-2-ylcarbamoyloxy)piperidin-1-yl]ethyl}methylcarbamoyl)furan-2-ylmethyl]piperazine-1-carboxylic acid methyl ester. MS m/z: [M + H⁺] calcd for $C_{33}H_{41}N_5O_6$, 604.31; found, 604.2. | 4-methoxycarbonylpiperazinyl structure |
| 15-11 | biphenyl-2-ylcarbamic acid 1-(2-{[5-(1,1-dioxo-1λ⁶-thiomorpholin-4-ylmethyl)furan-2-carbonyl]methyl-amino}ethyl)piperidin-4-yl ester. MS m/z: [M + H⁺] calcd for $C_{31}H_{38}N_4O_6S$, 595.25; found, 595.2. | 1,1-dioxothiomorpholinyl structure |
| 15-12 | biphenyl-2-ylcarbamic acid 1-(2-{[5-(4-acetylpiperazin-1-ylmethyl)furan-2-carbonyl]methylamino}ethyl)piperidin-4-yl ester. MS m/z: [M + H⁺] calcd for $C_{33}H_{41}N_5O_5$, 588.31; found, 588.2. | 4-acetylpiperazinyl structure |
| 15-13 | biphenyl-2-ylcarbamic acid 1-(2-{[5-(4-methanesulfonyl-piperazin-1-ylmethyl)furan-2-carbonyl]methylamino}ethyl)piperidin-4-yl ester. MS m/z: [M + H⁺] calcd for $C_{32}H_{41}N_5O_6S$, 624.28; found, 624.2. | 4-methanesulfonylpiperazinyl structure |

Example 16

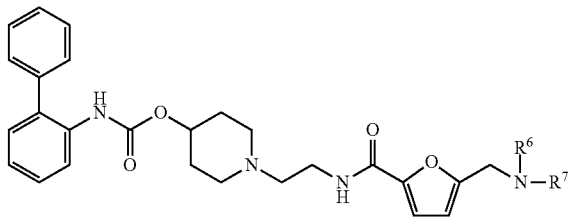

Using the procedure of Example 1, substituting 5-formyl-furan-2-carboxylic acid in place of 4-carboxybenzaldehyde in Preparation 9 and using that product in place of the product of Preparation 5, and substituting the appropriate amine in the reductive amination step, the following compounds were prepared.

| # | Name | —NR$^6$R$^7$ |
|---|---|---|
| 16-1 | biphenyl-2-yl-carbamic acid 1-{2-[(5-aminomethylfuran-2-carbonyl)amino]ethyl}piperidin-4-yl ester. MS m/z: [M + H$^+$] calcd for C$_{26}$H$_{30}$N$_4$O$_4$, 463.23. | —NH$_2$ |
| 16-2 | biphenyl-2-yl-carbamic acid 1-{2-[(5-methylamino methylfuran-2-carbonyl)amino]ethyl}piperidin-4-yl ester. MS m/z: [M + H$^+$] calcd for C$_{27}$H$_{32}$N$_4$O$_4$, 477.24; found, 477.2. | —NH(CH$_3$) |
| 16-3 | biphenyl-2-ylcarbamic acid 1-[2-({5-[(2-hydroxyethyl amino)methyl]furan-2-carbonyl}amino)ethyl]piperidin-4-yl ester. MS m/z: [M + H$^+$] calcd for C$_{28}$H$_{34}$N$_4$O$_5$, 507.25; found, 507.2. | —NH[(CH$_2$)$_2$OH] |

Assay 1

Radioligand Binding Assay

Membrane Preparation from Cells Expressing hM$_1$, hM$_2$, hM$_3$ and hM$_4$ Muscarinic Receptor Subtypes CHO cell lines stably expressing cloned human hM$_1$, hM$_2$, hM$_3$ and hM$_4$ muscarinic receptor subtypes, respectively, were grown to near confluency in medium consisting of HAM's F-12 supplemented with 10% FBS and 250 µg/mL Geneticin. The cells were grown in a 5% CO$_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared hM$_5$ receptor membranes were purchased directly from Perkin Elmer and stored at −80° C. until use.

Radioligand Binding Assay on Muscarinic Receptor Subtypes hM$_1$, hM$_2$, hM$_3$, hM$_4$ and hM$_5$ Radioligand binding assays were performed in 96-well microtiter plates in a total assay volume of 100 µL. CHO cell membranes stably expressing either the hM$_1$, hM$_2$, hM$_3$, hM4 or hM$_5$ muscarinic subtype were diluted in assay buffer to the following specific target protein concentrations (µg/well): 10 µg for hM$_1$, 10-15 µg for hM$_2$, 10-20 µg for hM$_3$, 10-20 µg for hM$_4$, and 10-12 µg for hM$_5$. The membranes were briefly homogenized using a Polytron tissue disruptor (10 seconds) prior to assay plate addition. Saturation binding studies for determining K$_D$ values of the radioligand were performed using L-[N-methyl-$^3$H] scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of K$_i$ values of test compounds were performed with [$^3$H]-NMS at 1 nM and eleven different test compound concentrations. The test compounds were initially dissolved to a concentration of 400 µM in dilution buffer and then serially diluted 5× with dilution buffer to final concentrations ranging from 10 µM to 100 µM. The addition order and volumes to the assay plates were as follows: 25 µL radioligand, 25 µL diluted test compound, and 50 µL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. K$_i$ values for test compounds were calculated from observed IC$_{50}$ values and the K$_D$ value of the radioligand using the Cheng-Prusoff equation (Cheng Y; Prusoff W. H. *Biochemical Pharmacology* 22(23):3099-108 (1973)). K$_i$ values were converted to pK$_i$ values to determine the geometric mean and 95% confidence intervals. These summary statistics were then converted back to K$_i$ values for data reporting. In this assay, a lower K$_i$ value indicates that the test compound has a higher binding affinity for the receptor tested. Exemplary compounds of the invention that were tested in this or a similar assay, typically were found to have a $K_i$ value of less than about 10 nM for the $M_3$ muscarinic receptor subtype.

Assay 2

Muscarinic Receptor Functional Potency Assays

Blockade of Agonist-Mediated Inhibition of cAMP Accumulation

In this assay, the functional potency of a test compound is determined by measuring the ability of the test compound to block oxotremorine-inhibition of forskolin-mediated cAMP accumulation in CHO-K1 cells expressing the $hM_2$ receptor. cAMP assays are performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells are rinsed once with dPBS and lifted with Trypsin-EDTA solution (0.05% trypsin/0.53 mM EDTA) as described in the Cell Culture and Membrane Preparation section above. The detached cells are washed twice by centrifugation at 650×g for five minutes in 50 mLs dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of $1.6 \times 10^6$-$2.8 \times 10^6$ cells/mL.

The test compound is initially dissolved to a concentration of 400 µM in dilution buffer (dPBS supplemented with 1 mg/mL BSA (0.1%)), and then serially diluted with dilution buffer to final molar concentrations ranging from 100 µM to 0.1 nM. Oxotremorine is diluted in a similar manner. To measure oxotremorine inhibition of adenylyl cyclase (AC) activity, 25 µL forskolin (25 µM final concentration diluted in dPBS), 25 µL diluted oxotremorine, and 50 µL it cells are added to agonist assay wells. To measure the ability of a test compound to block oxotremorine-inhibited AC activity, 25 µL forskolin and oxotremorine (25 µM and 5 µM final concentrations, respectively, diluted in dPBS) 25 µL diluted test compound, and 50 µL, cells are added to remaining assay wells.

Reactions are incubated for 10 minutes at 37° C. and stopped by addition of 100 µL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively. The $K_i$ values are converted to $pK_i$ values to determine the geometric mean and 95% confidence intervals. These summary statistics are then converted back to $K_i$ values for data reporting. In this assay, a lower $K_i$ value indicates that the test compound has a higher functional activity at the receptor tested. Compounds of the invention are expected to have a $K_i$ value of less than about 10 nM for blockade of oxotremorine-inhibition of forskolin-mediated cAMP accumulation in CHO-K1 cells expressing the $hM_2$ receptor, when tested in this or a similar assay.

Blockade of Agonist-Mediated [$^{35}$S]GTPγS Binding

In a second functional assay, the functional potency of test compounds can be determined by measuring the ability of the compounds to block oxotremorine-stimulated [$^{35}$S]GTPγS binding in CHO-K1 cells expressing the $hM_2$ receptor. At the time of use, frozen membranes are thawed and then diluted in assay buffer with a final target tissue concentration of 5-10 µg protein per well. The membranes are briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine is determined in each experiment. To determine the ability of a test compound to inhibit oxotremorine-stimulated [$^{35}$S]GTPγS binding, the following is added to each well of 96 well plates: 25 µL, of assay buffer with [$^{35}$S]GTPγS (0.4 nM), 25 µL of oxotremorine($EC_{90}$) and GDP (3 µM), 25 µL of diluted test compound and 25 µL CHO cell membranes expressing the $hM_2$ receptor. The assay plates are then incubated at 37° C. for 60 minutes. The assay plates are filtered over 1% BSA-pretreated GF/B filters using a PerkinElmer 96-well harvester. The plates are rinsed with ice-cold wash buffer for 3×3 seconds and then air or vacuum dried. Microscint-20 scintillation liquid (50 µL) is added to each well, and each plate is sealed and radioactivity counted on a topcounter (PerkinElmer). Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $IC_{50}$ values of the concentration-response curve for the test compound and the oxotremorine concentration in the assay as the $K_D$ and [L], ligand concentration, respectively. In this assay, a lower $K_i$ value indicates that the test compound has a higher functional activity at the receptor tested. Compounds of the invention are expected to have a $K_i$ value of less than about 10 nM for blockade of oxotremorine-stimulated [$^{35}$S] GTPγS binding in CHO-K1 cells expressing the $hM_2$ receptor, when tested in this or a similar assay.

Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C(PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIP, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium. For FLIPR calcium stimulation assays, CHO cells stably expressing the $hM_1$, $hM_3$ and $cM_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 μL/well of FLIPR buffer. The cells are then incubated with 50 μL/well of 4 μM FLUO-4AM (a 2× solution was made) for 40 minutes at 37° C., 5% carbon dioxide. Following the dye incubation period, cells are washed two times with FLIPR buffer, leaving a final volume of 50 μL/well.

To determine antagonist potency, the dose-dependent stimulation of intracellular $Ca^{2+}$ release for oxotremorine is first determined so that antagonist potency can later be measured against oxotremorine stimulation at an $EC_{90}$ concentration. Cells are first incubated with compound dilution buffer for 20 minutes, followed by agonist addition, which is performed by the FLIPR. An $EC_{90}$ value for oxotremorine is generated according to the method detailed in the FLIPR measurement and data reduction section below, in conjunction with the formula $EC_F=((F/100-F)\ \hat{}\ 1/H)*EC_{50}$. An oxotremorine concentration of $3\times EC_F$ is prepared in stimulation plates such that an $EC_{90}$ concentration of oxotremorine is added to each well in the antagonist inhibition assay plates. The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change. The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine $EC_{50}$ value as the $K_D$ and the oxotremorine $EC_{90}$ for the ligand concentration according to the Cheng-Prusoff equation (Cheng & Prusoff, 1973). In this assay, a lower $K_i$ value indicates that the test compound has a higher functional activity at the receptor tested. Compounds of the invention are expected to have a $K_i$ value of less than about 10 nM for blockade of agonist-mediated calcium release in CHO cells stably expressing the $hM_3$ receptor, when tested in this or a similar assay.

Assay 3

Determination of Duration of Bronchoprotection in Guinea Pig Model of Acetylcholine-Induced Bronchoconstriction This in vivo assay is used to assess the bronchoprotective effects of test compounds exhibiting muscarinic receptor antagonist activity. Groups of six male guinea pigs (Duncan-Hartley (HsdPoc:DH) Harlan, Madison, Wis.) weighing between 250 and 350 g are individually identified by cage cards. Throughout the study animals are allowed access to food and water ad libitum. Test compounds are administered via inhalation over 10 minutes in a whole-body exposure dosing chamber (R&S Molds, San Carlos, Calif.). The dosing chambers are arranged so that an aerosol was simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This is measured gravimetrically by comparing pre- and post-nebulization weights of the filled nebulizer.

The bronchoprotective effects of test compounds administered via inhalation are evaluated using whole body plethysmography at 1.5, 24, 48 and 72 hours post-dose. Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck was made. Then, the jugular vein is isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea is then dissected free and cannulated with a 14G teflon tube (#NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are complete, the animal is placed into a plethysmograph (#PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways do not collapse and that the animal does not suffer from hyperventilation. Once it is determined that baseline values are within the range 0.3-0.9 mL/cm $H_2O$ for compliance and within the range 0.1-0.199 cm $H_2O$/mL per second for resistance, the pulmonary evaluation is initiated. A Buxco pulmonary measurement computer progam enables the collection and derivation of pulmonary values. Starting this program initiates the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (#TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with ACh. ACh (0.1 mg/mL) is infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. If resistance or compliance has not returned to baseline values at 3 minutes following each ACh dose, the guinea pig's lungs are inflated 3 times with 4 mL of air from a 10 mL calibration syringe. Recorded pulmonary parameters includes respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one or both of the following ways:

(a) Pulmonary resistance ($R_L$, cm $H_2O$/mL per second) is calculated from the ratio of "change in pressure" to "the change in flow." The $R_L$ response to ACh (60 µg/min, 1H) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' are fitted with a four parameter logistic equation using GraphPad Prism, version 3.00 for Windows (GraphPad Software, San Diego, Calif.) to estimate bronchoprotective $ID_{50}$ (dose required to inhibit the ACh (60 µg/min) bronchoconstrictor response by 50%). The equation used is as follows:

$$Y = \text{Min} + (\text{Max}-\text{Min})/(1+10^{((\log ID50-X)*Hillslope)})$$

where X is the logarithm of dose, Y is the response (% Inhibition of ACh induced increase in $R_L$). Y starts at MM and approaches asymptotically to Max with a sigmoidal shape.

(b) The quantity $PD_2$, which is defined as the amount of ACh or histamine needed to cause a doubling of the baseline pulmonary resistance, is calculated using the pulmonary resistance values derived from the flow and the pressure over a range of ACh or histamine challenges using the following equation (which is derived from a equation used to calculate $PC_{20}$ values described in American Thoracic Society. Guidelines for methacholine and exercise challenge testing—1999. *Am J Respir Crit. Care Med.* 161: 309-329 (2000)):

$$PD_2 = \text{antilog}\left[\log C_1 + \frac{(\log C_2 - \log C_1)(2R_0 - R_1)}{R_2 - R_1}\right]$$

where: $C_1$ is the concentration of ACh or histamine preceding $C_2$; $C_2$ is the concentration of ACh or histamine resulting in at least a 2-fold increase in pulmonary resistance ($R_L$); $R_0$ is the baseline $R_L$ value; $R_1$ is the $R_L$ value after $C_1$; and $R_2$ is the $R_L$ value after $C_2$. An efficacious dose is defined as a dose that limits the bronchrestriction response to a 50 µg/mL dose of ACh to a doubling of the baseline pulmonary resistance ($PD_{2(50)}$).

Statistical analysis of the data is performed using a two-tailed Students t-test. A P-value <0.05 is considered significant. Generally, test compounds having a $PD_{2(50)}$ less than about 200 µg/mL for ACh-induced bronchoconstriction at 1.5 hours post-dose in this assay are preferred. Compounds of the invention are expected to have a $PD_{2(50)}$ of less than about 200 µg/mL for ACh-induced bronchoconstriction at 1.5 hours post-dose, when tested in this or a similar assay.

Assay 4

Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (1H) over a 10 minute time period in a pie shaped dosing chamber (R&S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PART Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, SC) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1996).

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The following equation is used:

$$Y = \text{Min} + (\text{Max}-\text{Min})/(1+10^{((\log ID50-X)*Hillslope)})$$

where X is the logarithm of dose, Y is the response (% inhibition of salivation). Y starts at Min and approaches asymptotically to Max with a sigmoidal shape. The ratio of the anti-sialagogue $ID_{50}$ to bronchoprotective $ID_{50}$ is used to compute the apparent lung-selectivity index of the test compound. Generally, compounds having an apparent lung-selectivity index greater than about 5 are preferred. Compounds of the invention are expected to have an apparent lung-selectivity index greater than 5, when tested in this or a similar assay.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g are used in these studies. Under isoflurane anesthesia (to effect), animals are instrumented with common carotid artery and jugular vein catheters (PE-50 tubing). The catheters are exteriorized utilizing a subcutaneous tunnel to the subscapular area. All surgical incisions are sutured with 4-0 Ethicon Silk and the catheters locked with heparin (1000 units/mL). Each animal is administered saline (3 mL, SC) at the end of surgery as well as buprenorphine (0.05 mg/kg, IM). Animals are allowed to recover on a heating pad before being returned to their holding rooms. Approximately 18 to 20 hours following surgery, the animals are weighed and the carotid artery catheter on each animal is connected to a transducer for recording arterial pressure. Arterial pressure and heart rate are recorded using a Biopac MP-100 Acquisition System. Animals are allowed to acclimate and stabilize for a period of 20 minutes.

Each animal is challenged with MCh (0.3 mg/kg, IV) administered through the jugular venous line and the cardiovascular response is monitored for 10 minutes. The animals are then placed into the whole body dosing chamber, which is connected to a nebulizer containing the test compound or vehicle solution. The solution is nebulized for 10 minutes using a gas mixture of breathable air and 5% carbon dioxide with a flow rate of 3 liters/minute. The animals are then removed from the whole body chamber and returned to their respective cages. At 1.5 and 24 hours post-dosing, the animals are re-challenged with MCh (0.3 mg/kg, IV) and the hemodynamic response is determined. Thereafter, the animals are euthanized with sodium pentobarbital (150 mg/kg, IV). MCh produces a decrease in mean arterial pressure (MAP) and decrease in heart rate (bradycardia). The peak decrease, from baseline, in MAP (depressor responses) is measured for each MCh challenge (before and after IH dosing). The effects of treatment on the MCh responses are expressed as % inhibition (mean+/−SEM) of the control depressor responses. Two-way ANOVA with the appropriate post-hoc test is used to test the effects of treatment and pre-treatment time. The depressor responses to MCh are expected to be relatively unchanged at 1.5 and 24 hours after inhalation dosing with vehicle. The ratio of the anti-depressor $ID_{50}$ to bronchoprotective $ID_{50}$ is used to compute apparent lung-selectivity of the test compound. Generally, compounds having an apparent lung-selectivity index greater than 5 are preferred. It is expected that the compounds of the invention will exhibit an apparent lung-selectivity index greater than 5, as measured in this or a similar assay.

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula I:

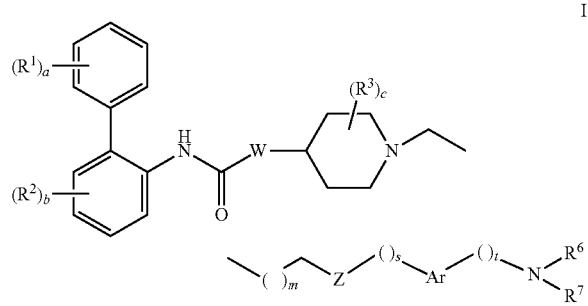

I wherein:
a is 0 or 1;
$R^1$ is -halo;
b is 0 or 1;
$R^2$ is -halo;
W is —O—;
c is 0;
m is 0 or 1;
Z is selected from —C(O)N($R^4$)— and —N($R^4$)C(O)—, where $R^4$ is selected from —H, —$C_{1-5}$alkyl, and —$C_{3-5}$cycloalkyl;
s is 0, 1 or 2;
Ar is a $C_{3-5}$heteroarylene group selected from pyridylene, thienylene, pyrrolylene, and furylene;
t is 0, 1 or 2;
$R^6$ is selected from —H, —$C_{1-5}$alkyl, and —$X^6R^{6a}$; where $X^6$ is —$C_{1-5}$alkylene and $R^{6a}$ is selected from —OH, —$C_{1-5}$alkoxy and -heteroaryl; and
$R^7$ is selected from —H, —$C_{1-5}$alkyl, —$C_{3-6}$cycloalkyl, and —$X^7R^{7a}$; where $X^7$ is selected from —$C_{1-5}$alkylene, —C(O)—, —$C_{1-5}$alkylene-C(O)—, —S($O_2$)—, —$C_{1-5}$alkylene-S($O_2$)—, and —S($O_2$)—$C_{1-5}$alkylene; and $R^{7a}$ is selected from —OH, —$C_{1-5}$alkyl, —$C_{3-6}$cycloalkyl, —$C_{1-5}$alkoxy, heteroaryl, —$NR^{7b}R^{7c}$, where $R^{7b}$ and $R^{7c}$ are independently —H or —$C_{1-5}$alkyl, and aryl optionally substituted with 1-2-$C_{1-5}$alkyl or halo groups;
wherein each alkyl and alkoxy group in $R^6$, $R^{6a}$, $R^7$, and $R^{7a-c}$ is optionally substituted with 1 to 5 fluoro substituents;
or a pharmaceutically acceptable salt or stereoisomer thereof.

2. The compound of claim 1, wherein a and b each represent 0.

3. The compound of claim 1, wherein m is 0 and t is 1.

4. The compound of claim 1, wherein Z is selected from —NHC(O)—, —N($CH_3$)C(O)—, and —C(O)NH—.

5. The compound of claim 1, wherein Ar is selected from 2,5-pyridylene, 2,5-thienylene, 2,4-pyrrolylene, 2,5-pyrrolylene, and 2,5-furylene.

6. The compound of claim 1, wherein a and b are 0; and Z is selected from —NHC(O)—, —N($CH_3$)C(O)—, and —C(O)NH—.

7. The compound of claim 1, wherein $R^6$ is —H and $R^7$ is selected from —H, —$C_{1-5}$alkyl, —$C_{3-6}$cycloalkyl, —$C_{1-5}$alkylene-OH, —$C_{1-5}$alkylene-$C_{3-6}$cycloalkyl, —$C_{1-5}$alkylene-$C_{1-5}$alkoxy, —$C_{1-5}$alkyleneheteroaryl, —C(O)—$C_{1-5}$alkyl, —C(O)—$C_{3-6}$cycloalkyl, —C(O)-heteroaryl, —$C_{1-5}$alkylene-C(O)—$NR^{7b}R^{7c}$, —S($O_2$)—$C_{1-5}$alkyl, —S($O_2$)-heteroaryl, —S($O_2$)-aryl, and —S($O_2$)—$C_{1-5}$alkylene-$NR^{7b}R^{7c}$; where the aryl is optionally substituted with 1-2-$C_{1-5}$alkyl or halo groups, and wherein each alkyl and alkoxy group in $R^7$ and $R^{7b-c}$ is optionally substituted with 1 to 5 fluoro substituents.

8. The compound of claim 1, wherein $R^6$ is —$C_{1-5}$alkyl and $R^7$ is selected from —$C_{1-5}$alkylene-OH, —$C_{1-5}$alkyleneheteroaryl, —$C_{1-5}$alkylene-C(O)OH, and —$C_{1-5}$alkylene-S($O_2$)—$C_{1-5}$alkyl; and wherein each alkyl group in $R^7$ is optionally substituted with 1 to 5 fluoro substituents.

9. The compound of claim 1, wherein $R^6$ and $R^7$ are different —$C_{1-5}$alkyl groups.

10. The compound of claim 1, wherein $R^6$ and $R^7$ are the same, and are selected from: —$C_{1-5}$alkyl, —$C_{1-5}$alkylene-OH, and —$C_{1-5}$alkylene-$C_{1-5}$alkoxy.

11. The compound of claim 1, selected from:
biphenyl-2-ylcarbamic acid 1-{2-[methyl(5-methylaminomethylpyridine-2-carbonyl)amino]ethyl}piperidin-4-yl ester;
biphenyl-2-ylcarbamic acid 1-{2-[(5-diethylaminomethylpyridine-2-carbonyl)methylamino]ethyl}piperidin-4-yl ester;

biphenyl-2-ylcarbamic acid 1-[2-({5-[(2-hydroxyethylamino)methyl]pyridine-2-carbonyl]methylamino)ethyl}piperidin-4-yl ester;

biphenyl-2-ylcarbamic acid 1-{2-[(5-{[(furan-2-ylmethyl)amino]methyl}pyridine-2-carbonyl)methylamino]ethyl}piperidin-4-yl ester;

biphenyl-2-ylcarbamic acid 1-{2-[(5-{[bis-(2-hydroxyethyl)amino]methyl}pyridine-2-carbonyl)methylamino]ethyl}piperidin-4-yl ester;

biphenyl-2-ylcarbamic acid 1-{2-[methyl-(5-methylaminomethylthiophene-2-carbonyl)amino]ethyl}piperidin-4-yl ester;

biphenyl-2-ylcarbamic acid 1-{2-[(5-diethylaminomethylthiophene-2-carbonyl)methylamino]ethyl}piperidin-4-yl ester;

biphenyl-2-ylcarbamic acid 1-[2-({5-[(2-hydroxyethylamino)methyl]thiophene-2-carbonyl}methylamino)ethyl]piperidin-4-yl ester;

biphenyl-2-ylcarbamic acid 1-{2-[(5-{[(furan-2-ylmethyl)amino]methyl}thiophene-2-carbonyl)methylamino]ethyl}piperidin-4-yl ester;

biphenyl-2-ylcarbamic acid 1-{2-[(5-{[bis-(2-hydroxyethyl)amino]methyl}thiophene-2-carbonyl)methylamino]ethyl}piperidin-4-yl ester;

biphenyl-2-ylcarbamic acid 1-{2-[(5-methylaminomethylthiophene-2-carbonyl)amino]ethyl}piperidin-4-yl ester;

biphenyl-2-ylcarbamic acid 1-[2-({5-[(2-hydroxyethylamino)methyl]thiophene-2-carbonyl}amino)ethyl]piperidin-4-yl ester;

biphenyl-2-ylcarbamic acid 1-{2-[methyl(4-methylaminomethyl-1H-pyrrole-2-carbonyl)amino]ethyl}piperidin-4-yl ester;

biphenyl-2-ylcarbamic acid 1-{2-[methyl-(5-methylaminomethyl-1H-pyrrole-2-carbonyl)amino]ethyl}piperidin-4-yl ester;

biphenyl-2-ylcarbamic acid 1-{2-[methyl(5-methylaminomethylfuran-2-carbonyl)amino]ethyl}piperidin-4-yl ester;

biphenyl-2-ylcarbamic acid 1-{2-[(5-diethylaminomethylfuran-2-carbonyl)methylamino]ethyl}piperidin-4-yl ester;

biphenyl-2-ylcarbamic acid 1-[2-({5-[(2-hydroxyethylamino)methyl]furan-2-carbonyl]methylamino)ethyl}piperidin-4-yl ester;

biphenyl-2-ylcarbamic acid 1-{2-[(5-{[(furan-2-ylmethyl)amino]methyl}furan-2-carbonyl)methylamino]ethyl}piperidin-4-yl ester;

biphenyl-2-ylcarbamic acid 1-{2-[(5-{[bis-(2-hydroxyethyl)amino]methyl}furan-2-carbonyl)methylamino]ethyl}piperidin-4-yl ester;

biphenyl-2-yl-carbamic acid 1-{2-[(5-aminomethylfuran-2-carbonyl)amino]ethyl}piperidin-4-yl ester;

biphenyl-2-yl-carbamic acid 1-{2-[(5-methylaminomethylfuran-2-carbonyl)amino]ethyl}piperidin-4-yl ester; and biphenyl-2-ylcarbamic acid 1-[2-({5-[(2-hydroxyethylamino)methyl]furan-2-carbonyl}amino)ethyl]piperidin-4-yl ester;

or a pharmaceutically acceptable salt thereof.

12. A pharmaceutical composition comprising a pharmaceutically acceptable carrier and the compound of claim 1.

13. The compound of claim 1 prepared by the process comprising:

(a) reacting a compound of formula II:

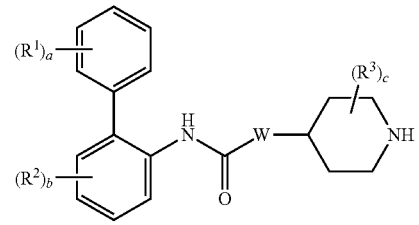

II or a salt thereof, with a compound of formula III:

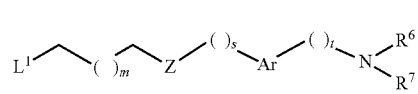

III wherein $L^1$ represents a leaving group; or (b) coupling a compound of formula IVa:

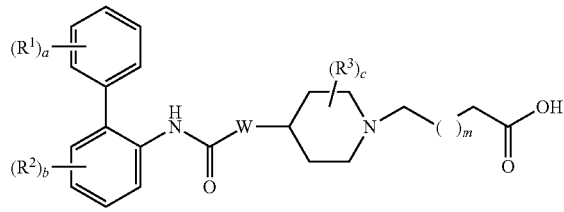

IVa or a reactive derivative thereof, with a compound of formula Va:

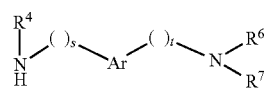

Va or coupling a compound of formula IVb:

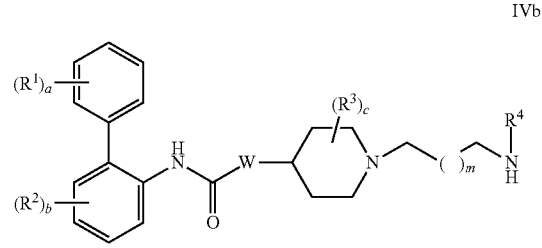

IVb with a compound of formula Vb:

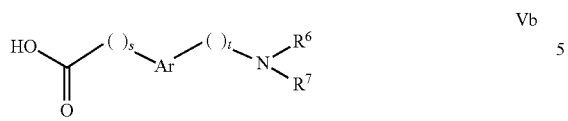

or a reactive derivative thereof; or
(c) reacting a compound of formula VI:

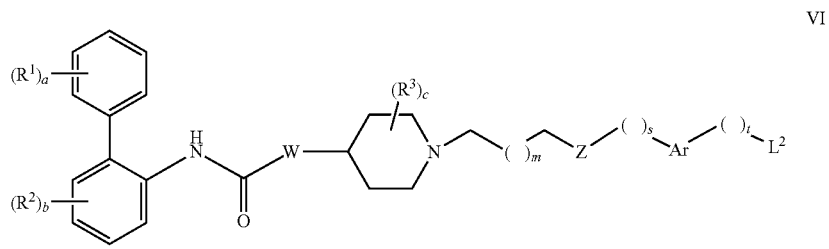

wherein $L^2$ represents a leaving group, with a compound of formula VII:

or
(d) reacting a compound of formula II with a compound of formula VIII:

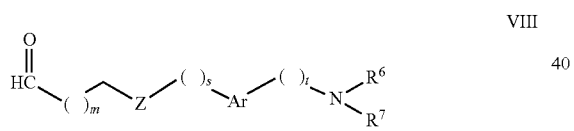

in the presence of a reducing agent; or
(e) reacting a compound of formula IX:

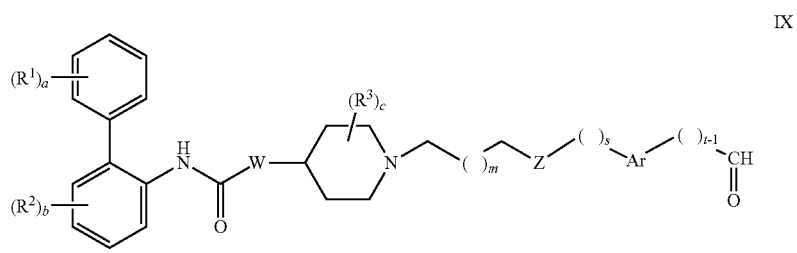

with a compound of formula VII in the presence of a reducing agent; and then
(f) removing any protecting groups that may be present to provide a compound of formula I.

14. The compound of claim 13, prepared by the process which further comprises forming a pharmaceutically acceptable salt of the compound of formula I.

* * * * *